United States Patent [19]
Rajput et al.

[11] Patent Number: 5,580,559
[45] Date of Patent: Dec. 3, 1996

[54] HYBRID PLASMINOGEN ACTIVATOR

[75] Inventors: Bhanu Rajput, College Park, Md.; Bhabatosh Chaudhuri, Münchenstein, Switzerland; Fredericus A. M. Asselbergs, Riehen, Switzerland; Bernd Meyhack, Magden, Switzerland; Jutta Heim, Ramlinsburg, Switzerland; Jan van Oostrum, Flüh, Switzerland; Sefik Alkan, Riehen, Switzerland

[73] Assignee: Ciba-Geigy Corporation, Tarrytown, N.Y.

[21] Appl. No.: 311,848

[22] Filed: Sep. 23, 1994

Related U.S. Application Data

[60] Continuation of Ser. No. 49,469, Apr. 19, 1993, abandoned, which is a division of Ser. No. 808,936, Dec. 13, 1991, Pat. No. 5,242,819, which is a continuation of Ser. No. 361,015, Jun. 2, 1989, abandoned, which is a continuation-in-part of Ser. No. 125,039, Nov. 23, 1987, abandoned.

[30] Foreign Application Priority Data

| Dec. 5, 1986 | [GB] | United Kingdom | 8629153 |
| Jan. 20, 1987 | [GB] | United Kingdom | 8701160 |
| Apr. 23, 1987 | [GB] | United Kingdom | 8709656 |
| Jul. 6, 1987 | [GB] | United Kingdom | 8715890 |

[51] Int. Cl.$^6$ .......................... A61K 38/49; C12N 9/48; C12N 9/72; C12N 9/64
[52] U.S. Cl. ...................... 424/94.63; 424/94.64; 435/212; 435/215; 435/226
[58] Field of Search ................. 424/94.63, 94.64; 435/172.3, 212, 215, 226

[56] References Cited

U.S. PATENT DOCUMENTS

| 4,916,071 | 4/1990 | Hung et al. | 435/212 |
| 5,204,255 | 4/1993 | Tagawa et al. | 435/215 |

FOREIGN PATENT DOCUMENTS

| 155387 | 9/1985 | European Pat. Off. |
| 207589 | 2/1986 | European Pat. Off. |
| 178105 | 4/1986 | European Pat. Off. |
| 196920 | 10/1986 | European Pat. Off. |
| 234051 | 2/1987 | European Pat. Off. |
| 213794 | 3/1987 | European Pat. Off. |
| 227462 | 7/1987 | European Pat. Off. |
| 231883 | 8/1987 | European Pat. Off. |
| 241209 | 10/1987 | European Pat. Off. |
| 241208 | 10/1987 | European Pat. Off. |
| 86/01538 | 3/1986 | WIPO |
| 87/03906 | 7/1987 | WIPO |
| 87/04722 | 8/1987 | WIPO |

OTHER PUBLICATIONS de Vries et al., "Artificial Exon Shuffling: Construction of Hybrid cDNAs Containing Domains of Tissue–Type Plasminogen Activator (t–PA) and Urokinase (u–PA)", *Thrombosis and Haemostasis*, 58: Abstract No 1141:314 (1987).
Friezner–Degen et al., "The Human Tissue Plasminogen Activator Gene", *J. Biol. Chem.* 261 (15):6972–6981 (1986).
Gheysen et al., "Characterization of a Recombinant Fusion Protein of the Finger Domain of Tissue–type Plasminogen Activator with a Truncated Single Chain Urokinase–type Plasminogen Activator", *J. Biol. Chem.*, 262(24): 11779–11784 (1987).
Holmes et al., "Cloning and Expression of the Gene for Pro–urokinase in *Escherichia coli*", *Biotechnology*, 3:923–929 (1985).
Ichinose et al., "Localization of the Binding Site of Tissue–Type Plasminogen Activator to Fibrin", *J. Clin. Invest.*, 78:163–169 (1986).
Kagitani et al., "Expression of E. coli of finger–domain lacking tissue–type plasminogen activator with high fibrin affinity", *FEBS LETTERS*, 189(1): 145–149 (1985).
Lee et al., "Construction and Expression of Hybrid Plasminogen Activators Prepared from Tissue–Plasminogen Activator (t–PA) and Urokinase (u–PA) Genes", *Thrombosis and Haemostasis*, 58: Abstract No. 1140:313 (1987).
Novokhatny et al., "Domains in Human Plasminogen", *J. Mol. Biol.*, 179:215–232 (1984).
Ny et al., "The structure of the human tissue–type plasminogen activator gene: Correlation of intron and exon structures to functional and structural domains", *Proc. Natl. Acad. Sci, USA*, 81: 5355–5359 (1984).
Penninca et al., "Cloning and expression of human tissue–type plasminogen activator cDNA in *E. coli*", *Nature*, 301: 214–221 (1983).
Piérard et al., "Mutant and Chimeric Recombinant Plasminogen Activators", *J. Biol. Chem.*, 262(24): 11771–11778 (1987).
Riccio et al., "The human urokinase–plasminogen activator gene and its promoter", *Nucleic Acids Research*, 13(8): 2759–2771 (1985).
Robbins et al., "Covalent molecular weight–92,000 hybrid plasminogen activator derived from human plasmin amino–terminal and urokinase carboxyl–terminal domains.", *Chemical Abstracts*, 105: 322 #20872a (1986).
Ryan et al., "Photoaffinity labeling of functionally different lysine–binding sites in human plasminogen and plasmin", *Biochimica et Biophysica. Acta.*, 830: 187–194 (1985).
Trexler et al., "Residues of Cys–1 and Cys–79 are not Essential for Refolding of Reduced–Denatured Kringle 4 Fragment of Human Plasminogen", *Biochimica et Biophysica. Acta.*, 787: 275–280 (1984).
Váli et al., "The Fibrin–binding Site of Human Plasminogen", *J. Biol. Chem.*, 259: 13690–13694 (1984).
van Zonneveld et al., "Autonomous functions of structural domains on human tissue–type plasminogen activator", *Proc. Natl. Acad. Sci, USA*, 83: 4670–4674 (1986).

*Primary Examiner*—Dian C. Jacobson
*Attorney, Agent, or Firm*—James Scott Elmer

[57] ABSTRACT

Novel single-chain hybrid plasminogen activators having an amino acid sequence composed of at least two subsequences corresponding in amino acid identity and number to subsequences of human t-PA and of human u-PA, and mutants thereof in which at least one of the N-glycosylation sites is modified such that glycosylation cannot take place at these sites exhibit valuable pharmacological properties. The hybrid plasminogen activators are produced by recombinant DNA technology.

5 Claims, 38 Drawing Sheets

```
  1 AGGGCTGGAGAGAAACCTCTGCGAGGAAGGGAAGGAGCAAGCCGTGAATTTAAGGA

MET ASP ALA MET LYS ARG GLY LEU CYS CYS VAL        -25
 60 CGCTGTGAAGCAATC ATG GAT GCA ATG AAG AGA GGG CTC TGC TGT GTG

LEU LEU LEU CYS GLY ALA VAL PHE VAL SER PRO SER GLN GLU ILE   -10
108 CTG CTA CTG TGT GGA GCA GTC TTC GTT TCG CCC AGC CAG GAA ATC

HIS ALA ARG PHE ARG ARG GLY ALA ARG SER TYR GLN VAL ILE CYS     6
153 CAT GCC CGA TTC AGA AGA GGA GCC AGA TCT TAC CAA GTG ATC TGC

ARG ASP GLU LYS THR GLN MET ILE TYR GLN HIS GLN SER TRP        21
198 AGA GAT GAA AAA ACG CAG ATG ATA TAC CAG CAA CAT CAG TCA TGG

LEU ARG PRO VAL LEU ARG SER ASN ARG VAL GLU TYR CYS TRP CYS    36
243 CTG CGC CCT GTG CTC AGA AGC AAC CGG GTG GAA TAT TGC TGG TGC

ASN SER GLY ARG ALA GLN CYS HIS SER VAL PRO VAL LYS SER CYS    51
288 AAC AGT GGC AGG GCA CAG TGC CAC TCA GTG CCT GTC AAA AGT TGC

SER GLU PRO ARG CYS PHE ASN GLY GLY THR CYS GLN GLN ALA LEU    66
333 AGC GAG CCA AGG TGT TTC AAC GGG GGC ACC TGC CAG CAG GCC CTG
```

FIG. 1A

| | | | | | | | | | | | | | | | |
|---|---|---|---|---|---|---|---|---|---|---|---|---|---|---|---|
| 378 | TYR TAC | PHE TTC | SER TCA | ASP GAT | PHE TTC | VAL GTG | CYS TGC | GLN CAG | CYS TGC | PRO CCC | GLU GAA | GLY GGA | PHE TTT | ALA GCT | GLY GGG | 81 |
| 423 | LYS AAG | CYS TGC | CYS TGT | GLU GAA | ILE ATA | ASP GAT | THR ACC | ARG AGG | ALA GCC | THR ACG | CYS TGC | TYR TAC | GLU GAG | ASP GAC | GLN CAG | 96 |
| 468 | GLY GGC | ILE ATC | SER AGC | TYR TAC | ARG AGG | GLY GGC | THR ACG | TRP TGG | SER AGC | THR ACA | ALA GCG | GLU GAG | SER AGT | GLY GGC | ALA GCC | 111 |
| 513 | GLU GAG | CYS TGC | THR ACC | ASN AAC | TRP TGG | ASN AAC | SER AGC | SER AGC | ALA GCG | LEU TTG | ALA GCC | GLN CAG | LYS AAG | PRO CCC | TYR TAC | 126 |
| 558 | SER AGC | GLY GGG | ARG CGG | ARG AGG | PRO CCA | ASP GAC | ALA GCC | ILE ATC | ARG AGG | LEU CTG | GLY GGC | LEU CTG | GLY GGG | ASN AAC | HIS CAC | 141 |
| 603 | ASN AAC | TYR TAC | CYS TGC | ARG AGA | ASN AAC | PRO CCA | ASP GAT | ARG CGA | ASP GAC | SER TCA | LYS AAG | PRO CCC | TRP TGG | CYS TGC | TYR TAC | 156 |
| 648 | VAL GTC | PHE TTT | LYS AAG | ALA GCG | GLY GGG | LYS AAG | TYR TAC | SER AGC | SER TCA | GLU GAG | PHE TTC | CYS TGC | SER AGC | THR ACC | PRO CCT | 171 |
| 693 | ALA GCC | CYS TGC | SER TCT | GLU GAG | GLY GGA | ASN AAC | SER AGT | ASP GAC | CYS TGC | TYR TAC | PHE TTT | GLY GGG | ASN AAT | GLY GGG | SER TCA | 186 |

FIG. 1B

```
     ALA TYR ARG GLY THR HIS SER LEU THR GLU SER GLY ALA SER CYS   201
 738 GCC TAC CGT GGC ACG CAC AGC CTC ACC GAG TCG GGT GCC TCC TGC

LEU PRO TRP ASN SER MET ILE LEU ILE GLY LYS VAL TYR THR ALA   216
 783 CTC CCG TGG AAT TCC ATG ATC CTG ATA GGC AAG GTT TAC ACA GCA

GLN ASN PRO SER ALA GLN ALA LEU GLY LEU GLY LYS HIS ASN TYR   231
 828 CAG AAC CCC AGT GCC CAG GCA CTG GGC CTG GGC AAA CAT AAT TAC

CYS ARG ASN PRO ASP GLY ASP ALA LYS PRO TRP CYS HIS VAL LEU   246
 873 TGC CGG AAT CCT GAT GGG GAT GCC AAG CCC TGG TGC CAC GTG CTG

LYS ASN ARG ARG LEU THR TRP GLU TYR CYS ASP VAL PRO SER CYS   261
 918 AAG AAC CGC AGG CTG ACG TGG GAG TAC TGT GAT GTG CCC TCC TGC

SER THR CYS GLY LEU ARG GLN TYR SER GLN PRO GLN PHE ARG ILE   276
 963 TCC ACC TGC GGC CTG AGA CAG TAC AGC CAG CCT CAG TTT CGC ATC

LYS GLY GLY LEU PHE ALA ASP ILE ALA SER HIS PRO TRP GLN ALA   291
1008 AAA GGA GGG CTC TTC GCC GAC ATC GCC TCC CAC CCC TGG CAG GCT

ALA ILE PHE ALA LYS HIS ARG ARG SER PRO GLY GLU ARG PHE LEU   306
1053 GCC ATC TTT GCC AAG CAC AGG AGG TCG CCC GGA GAG CGG TTC CTG

CYS GLY GLY ILE LEU ILE SER SER CYS TRP ILE LEU SER ALA ALA   321
1098 TGC GGG GGC ATA CTC ATC AGC TCC TGC TGG ATT CTC TCT GCC GCC
```

FIG. 1C

| | | | | | | | | | | | | | | | |
|---|---|---|---|---|---|---|---|---|---|---|---|---|---|---|---|
| 1143 | HIS CAC | CYS TGC | PHE TTC | GLN CAG | GLU GAG | ARG AGG | PHE TTT | PRO CCG | HIS CAC | HIS CAC | LEU CTG | THR ACG | VAL GTG | ILE ATC | 336 |
| 1188 | LEU TTG | GLY GGC | ARG AGA | THR ACA | TYR TAC | ARG CGG | VAL GTG | VAL GTC | PRO CCT | GLY GGC | GLU GAG | GLU GAG | GLU GAG | LYS AAA | 351 |
| 1233 | PHE TTT | GLU GAA | VAL GTC | GLU GAA | LYS AAA | TYR TAC | ILE ATT | VAL GTC | HIS CAT | LYS AAG | GLU GAA | PHE TTC | ASP GAT | ASP GAT | 366 |
| 1278 | THR ACT | TYR TAC | ASP GAC | ASN AAT | ASP GAC | ILE ATT | ALA GCG | LEU CTG | LEU CTG | GLN CAG | LEU CTG | LYS AAA | SER TCG | ASP GAT | SER TCG | 381 |
| 1323 | SER TCC | ARG CGC | CYS TGT | ALA GCC | GLN CAG | GLU GAG | SER AGC | SER AGC | VAL GTG | VAL GTC | ARG CGC | THR ACT | VAL GTG | CYS TGC | LEU CTT | 396 |
| 1368 | PRO CCC | PRO CCG | ALA GCG | ASP GAC | LEU CTG | GLN CAG | LEU CTG | PRO CCG | ASP GAC | TRP TGG | THR ACG | GLU GAG | CYS TGT | GLU GAG | LEU CTC | 411 |
| 1413 | SER TCC | GLY GGC | TYR TAC | LYS AAG | HIS CAT | GLU GAG | ALA GCC | LEU TTG | SER TCT | PRO CCT | PHE TTC | TYR TAT | SER TCG | GLU GAG | | 426 |
| 1458 | ARG CGG | LEU CTG | LYS AAG | GLU GAG | ALA GCT | HIS CAT | VAL GTC | ARG AGA | LEU CTG | TYR TAC | PRO CCA | SER TCC | SER AGC | ARG CGC | CYS TGC | 441 |

FIG. 1D

```
           THR SER GLN HIS LEU LEU ASN ARG THR VAL ASP ASN MET LEU   456
     1503  ACA TCA CAA CAT TTA CTT AAC AGA ACA GTC GAC AAC ATG CTG

CYS ALA GLY ASP THR ARG SER GLY GLY PRO GLN ALA ASN LEU HIS   471
     1548  TGT GCT GGA GAC ACT CGG AGC GGC GGG CCC CAG GCA AAC TTG CAC

ASP ALA CYS GLN GLY ASP SER GLY GLY PRO LEU VAL CYS LEU ASN   486
     1593  GAC GCC TGC CAG GGC GAT TCG GGA GGC CCC CTG GTG TGT CTG AAC

ASP GLY ARG MET THR LEU VAL GLY ILE ILE SER TRP GLY LEU GLY   501
     1638  GAT GGC CGC ATG ACT TTG GTG GGC ATC ATC AGC TGG GGC CTG GGC

CYS GLY GLN LYS ASP VAL PRO GLY VAL TYR THR LYS VAL THR ASN   516
     1683  TGT GGA CAG AAG GAT GTC CCG GGT GTG TAC ACT AAG GTT ACC AAC

TYR LEU ASP TRP ILE ARG ASP ASN MET ARG PRO                   527
     1728  TAC CTA GAC TGG ATT CGT GAC AAC ATG CGA CCG TGA CCAGGAACACC
```

FIG.1E

```
1775  CGACTCCTCAAAAGCAAATGAGATCCCGCCCTCTCTTCTTCAGAAGACACTGCAAAGGC
1834  GCAGTGCTTCTCTACAGACTTCTCCAGACCCACCACCCGCAGAAGCCGGGACGAGACCC
1893  TACAGGAGAGGGAAGAGTGCATTTCCCAGATACTTCCCATTTGGAAGTTTTCAGGAC
1952  TTGGTCTGATTTCAGGATACTCTGTCAGATGGGAAGACATGAATGCACACTAGCCCTCTC
2011  CAGGAATGCCCTCCCTGGGCCAGAAAGTGGCCATGCCCACCCTGTTTTACGCTAAAGCC
2070  CAACCTCCTGACCCTGTCACCGTGAGCAGCTTTGGAAACAGGACCACAAAATGAAAGCA
2129  TGTCTCAATAGTAAAAGATACAAGA
```

FIG. 1F

```
1    CCCGGGCTCCGGGCTGCGGGTCTCCTGCCGCAGCCACCGAGCCGCCGTCTAGCCGCCCGA

MET ARG ALA LEU LEU ALA ARG LEU LEU LEU CYS VAL    -9
60   CCTCGCCACC  ATG AGA GCC CTG CTG GCG CGC CTG CTG CTT CTC TGC GTC

LEU VAL VAL SER ASP SER LYS GLY SER ASN GLU LEU HIS GLN VAL     7
106  CTG GTC GTG AGC GAC TCC AAA GGC AGC AAT GAA CTT CAT CAA GTT

PRO SER ASN CYS ASP CYS LEU ASN GLY GLY THR CYS VAL SER ASN    22
151  CCA TCG AAC TGT GAC TGT CTA AAT GGA GGA ACA TGT GTG TCC AAC

LYS TYR PHE SER ASN ILE HIS TRP CYS ASN CYS PRO LYS LYS PHE    37
196  AAG TAC TTC TCC AAC ATT CAC TGG TGC AAC TGC CCA AAG AAA TTC

GLY GLY GLN HIS CYS GLU ILE ASP LYS SER LYS THR CYS TYR GLU    52
241  GGA GGG CAG CAC TGT GAA ATA GAT AAG TCA AAA ACC TGC TAT GAG

GLY ASN GLY HIS PHE TYR ARG GLY LYS ALA SER THR ASP THR MET    67
286  GGG AAT GGT CAC TTT TAC CGA GGA AAG GCC AGC ACT GAC ACC ATG

GLY ARG PRO CYS LEU PRO TRP ASN SER ALA THR VAL LEU GLN GLN    82
331  GGC CGG CCC TGC CTG CCC TGG AAC TCT GCC ACT GTC CTT CAG CAA

THR TYR HIS ALA HIS ARG SER ASP ALA LEU GLN LEU GLY LEU GLY    97
376  ACG TAC CAT GCC CAC AGA TCT GAT GCT CTT CAG CTG GGC CTG GGG
```

FIG.3A

```
         LYS HIS ASN TYR CYS ARG ASN PRO ASP ASN ARG ARG ARG PRO TRP   112
    421  AAA CAT AAT TAC TGC AGG AAC CCA GAC AAC CGG AGG CGA CCC TGG

CYS TYR VAL GLN VAL GLY LEU LYS PRO LEU VAL GLN GLU CYS MET   127
    466  TGC TAT GTG CAG GTG GGC CTA AAG CCG CTT GTC CAA GAG TGC ATG

VAL HIS ASP CYS ALA ASP GLY LYS LYS PRO SER SER PRO PRO GLU   142
    511  GTG CAT GAC TGC GCA GAT GGA AAA AAG CCC TCC TCT CCT CCA GAA

GLU LEU LYS PHE GLN CYS GLY GLN LYS THR LEU ARG PRO ARG PHE   157
    556  GAA TTA AAA TTT CAG TGT GGC CAA AAG ACT CTG AGG CCC CGC TTT

LYS ILE ILE GLY GLU PHE THR THR ILE GLU ASN GLN PRO TRP       172
    601  AAG ATT ATT GGG GGA GAA TTC ACC ACC ATC GAG AAC CAG CCC TGG

PHE ALA ALA ILE TYR ARG ARG HIS ARG GLY GLY SER VAL THR TYR   187
    646  TTT GCG GCC ATC TAC AGG AGG CAC CGG GGG TCT GTC ACC TAC

VAL CYS GLY GLY SER LEU ILE SER PRO CYS TRP VAL ILE SER ALA   202
    691  GTG TGT GGA GGC AGC CTC ATC AGC CCT TGC TGG GTG ATC AGC GCC

THR HIS CYS PHE ILE ASP TYR PRO LYS LYS GLU ASP TYR ILE VAL   217
    736  ACA CAC TGC TTC ATT GAT TAC CCA AAG AAG GAG GAC TAC ATC GTC
```

FIG. 3B

```
     TYR LEU GLY ARG SER ARG LEU ASN SER ASN THR GLN GLY GLU MET  232
781  TAC CTC GGT CGC TCA AGG CTT AAC TCC AAC ACG CAA GGG GAG ATG

LYS PHE GLU VAL GLU ASN LEU ILE LEU HIS LYS ASP TYR SER ALA  247
826  AAG TTT GAG GTG GAA AAC CTC ATC CTA CAC AAG GAC TAC AGC GCT

ASP THR LEU ALA HIS HIS ASN ASP ILE ALA LEU LEU LYS ILE ARG  262
871  GAC ACG CTT GCT CAC CAC AAC GAC ATT GCC TTG CTG AAG ATC CGT

SER LYS GLU GLY ARG CYS ALA GLN PRO SER ARG THR ILE GLN THR  277
916  TCC AAG GAG GGC AGG TGT GCG CAG CCA TCC CGG ACT ATA CAG ACC

ILE CYS LEU PRO SER MET TYR ASN ASP PRO GLN PHE GLY THR SER  292
961  ATC TGC CTG CCC TCG ATG TAT AAC GAT CCC CAG TTT GGC ACA AGC

CYS GLU ILE THR GLY PHE GLY LYS GLU ASN SER THR ASP TYR LEU  307
1006 TGT GAG ATC ACT GGC TTT GGA AAA GAG AAT TCT ACC GAC TAT CTC

TYR PRO GLU GLN LEU LYS MET THR VAL VAL LYS LEU ILE SER HIS  322
1051 TAT CCG GAG CAG CTG AAA ATG ACT GTT GTG AAG CTG ATT TCC CAC

ARG GLU CYS GLN GLN PRO HIS TYR TYR GLY SER GLU VAL THR THR  337
1096 CGG GAG TGT CAG CAG CCC CAC TAC TAC GGC TCT GAA GTC ACC ACC

LYS MET LEU CYS ALA ALA ASP PRO GLN TRP LYS THR ASP SER CYS  352
1141 AAA ATG CTA TGT GCT GCT GAC CCA CAA TGG AAA ACA GAT TCC TGC
```

```
          GLN GLY ASP SER GLY GLY PRO LEU VAL CYS SER LEU GLN GLY ARG    367
1186      CAG GGA GAC TCA GGG GGA CCC CTC GTC TGT TCC CTC CAA GGC CGC

MET THR LEU THR GLY ILE VAL SER TRP GLY ARG GLY CYS ALA LEU    382
1231      ATG ACT TTG ACT GGA ATT GTG AGC TGG GGC CGT GGA TGT GCC CTG

LYS ASP LYS PRO GLY VAL TYR THR ARG VAL SER HIS PHE LEU PRO    397
1276      AAG GAC AAG CCA GGC GTC TAC ACG AGA GTC TCA CAC TTC TTA CCC

TRP ILE ARG SER HIS THR LYS GLU GLU ASN GLY LEU ALA LEU        411
1321      TGG ATC CGC AGT CAC ACC AAG GAG GAA AAT GGC CTG GCC CTC TGA

1366      GGGTCCCCAGGGAGGAAACGGGCACCACCCGCTTTCTGCTGGTGTCATTTTGCAGTA

1426      GAGTCATCTCCATCAGCTGTAAGAAGAGACTGGGAAGATAGCTCTGCACAGATGGATTT

1486      GCCTGTGCCACCCACCAGGGTGAACGACAATAGCTTTACCCTCAGGCATAGGCCTGGTG

1546      CTGGCTGCCCCAGACCCCCTCTGGCCAGGATGGAGGGTGGTCCTGACTCAACATGTTACTG

1606      ACCAGCAACTTGTCTTTTTCTGGACTGAAGCCTGCAGGAGTTAAAAGGGCAGGCATCT

1666      CCTGTGCCATGGGTGAAGGGAGAGAGCCAGCTCCCCCGACGGTGGGCATTTGTGAGGCCCATG

1726      GTTGAGAAATGAATAATTTCCCAATTAGGAAGTGTAACAGCTGAGGTCTCTTGAGGGAGC
```

1786 TTAGCCAATGTGTGGGAGCAGCGGGTTTGGGGAGCAGAGAGACACTAACGACTTCAGGGCAGGGC

1846 TCTGATATTCCATGAATGTATCAGGAAATATATGTGTGTGTATGTTTGCACACTTGTG

1906 TGTGGGCTGTGAGTGTAAGTGTGAGTAAGAGCTGGTGTCTGATTGTTAAGTCTAAATATT

1966 TCCTTAAACTGTGTGGACTGTGATGCCACACAGAGTGGTCTTTCTGGAGAGGTTATAGGT

2026 CACTCCTGGGCCCTCTTGGGTCCCCCACGTGACAGTGCCTGGAATGTATTATTCTGCAG

2086 CATGACCTGTGTGACCAGCACTGTCTCAGTTTCACTTTCACATAGATGTCCCTTTCTTGGCC

2146 AGTTATCCCTTCCTTTAGCCTAGTTCATCCAATCCCTCACTGGGGTGAGGACCACT

2206 CCTTACACTGAATAATTTATATATTTCACTATTTTATTTATATTTTTGTAATTTAAATAAA

2266 AGTGATCAATAAAATGTGATTTTTCTG(A)n

FIG. 3E

HYBRID PLASMINOGEN ACTIVATOR

CROSS REFERENCE TO RELATED APPLICATION

This application is a continuation, of application Ser. No. 08/049,469, filed Apr. 19, 1993, now abandoned which is a divisional application of Ser. No. 07/808,936 filed on Dec. 13, 1991, now issued on Sep. 7, 1993 U.S. Pat. No. 5,242,819, which is a continuation of Ser. No. 07/361,015 filed Jun. 2, 1989, now abandoned, which is a continuation-in-part of Ser. No. 07/125,039 filed Nov. 23, 1987, now abandoned.

The invention concerns hybrid plasminogen activators, DNAs coding for such hybrid plasminogen activators, hybrid vectors containing such DNAs, hosts transformed with such hybrid vectors, processes for the preparation of such hybrid plasminogen activators, DNAs, hybrid vectors and hosts, and pharmaceutical compositions containing such hybrid plasminogen activators.

Blood clots are the main cause of morbidity and of mortality of humans in the developed world. Blood clots are composed of fibrin which is formed from its soluble precursor fibrinogen by the action of the enzyme thrombin. An array of enzymes and other substances ensure that clots normally form only when and where they are required to prevent loss of blood.

Mammalian plasma contains an enzymatic system, The fibrinolytic system, capable of dissolving blood clots. One component of the fibrinolytic system is a group of enzymes named plasminogen activators, which convert plasminogen (an inactive proenzyme form of plasmin) to the proteolytic enzyme plasmin. Plasmin then degrades the fibrin network of the clots to form soluble products. In cases where the thrombolytic capacity of the body is insufficient to remove intravascular thrombi, for example in patients suffering from thromboembolisms or post-surgical complications, it may be indispensable to use exogenously administered thrombolytic agents.

Two types of plasminogen activators (hereinafter referred to as "PAs") can be isolated from human body fluids or cells: urokinase or urokinase-type plasminogen activator (hereinafter referred to as "u-PA"), a serine protease occurring e.g. in human urine and kidney cells, and tissue-type plasminogen activator (hereinafter referred to as "t-PA") which is produced by endothelial cells and found in a number of endocrine tissues.

Both t-PA and u-PA exist in two molecular forms: a single-chain form (often designated as "sc-t-PA" and "sc-u-PA", respectively) and a two-chain (tc) form. The single-chain or pro-enzyme form is converted into the two-chain form by the action of proteolytic enzymes at well defined positions in the polypeptide sequence. The resulting two chains of the processed PA protein remain attached to each other via a sulphur bridge. The carboxyterminal fragment or B-chain mediates the enzymatic activity of the PA whereas the aminoterminal A-chain contains regulatory units such as fibrin binding sites. The specific binding of an inactive sc-PA to components of the blood clot, such as fibrin, followed by conversion to the active tc-PA by catalytic amounts of proteolytic enzymes present at that site results in an effective site-specific drug.

t-PA and u-PA are encoded by two different genes, can be distinguished immunologically and enzymatically and have a different profile of responses to inhibitors, stimulators and activators. Thus, only t-PA is strongly inhibited by the protease inhibitor from Erytrina latissima (DE-3). T-PA activity is greatly stimulated by fibrin and fibrin fragments whereas u-PA activity is insensitive to stimulation by fibrin and its fragments. Another property distinguishing the two PA enzymes is that tc-t-PA has a high affinity for fibrin and fibrin fragments, whereas tc-u-PA has no appreciable fibrin affinity.

Considering the unsatisfactory serum stability of injected tPAs, the low affinity of tc-u-PA for fibrin and that the fibrin affinity of sc-u-PA is thought to be indirect i.e. requiring an additional blood factor (cf. D. J. Binnema et al., 8th Int. Congress of Fibrinolysis, Vienna, 1986), there is a continued need for improved plasminogen activators having a high affinity to fibrin, a more favorable response to stimulators, a reduced inactivation by inhibitors and longer effective half-lives in the blood circulation.

It is therefore an object of the present invention to provide novel hybrid plasminogen activators retaining the beneficial properties of t-PA and u-PA while lacking unwanted properties of the parent enzymes.

It has surprisingly been found that, for the treatment of thrombosis and other conditions, where it is desirable to produce fibrinolysis through plasminogen activation, single-chain hybrid PA proteins exhibit superior biological properties when compared to single-chain t-PA and u-PA. More specifically, compared to native PAs lower quantities of the novel PA molecules according to the present invention are required to lyse blood clots in vivo. The single-chain hybrid PA molecules according to the invention can be produced in large quantities through recombinant DNA technology and will upon injection into patients only be converted into their two-chain form under influence of fibrin at the site of the blood clot to be lysed. Two-chain hybrid PA molecules have been described in the literature (European Patent Application No. 155,387: K. C. Robbins, 8th International Congress of Fibrinolysis, Vienna, 1986), but the more favorable single-chain forms of hybrid PA molecules cannot be produced at the protein level as disclosed in the literature cited but can only be produced in large amounts and on industrial scale by recombinant DNA technology.

Accordingly it is a further object of the present invention to provide means and methods for the production of said single-chain u-PA/t-PA hybrid proteins. Such means include DNAs coding for said u-PA/t-PA hybrid proteins, hybrid vectors containing said DNAs and hosts transformed with said hybrid vectors. There are also provided methods for the production of said single-chain u-PA/t-PA hybrid proteins, said DNAs, said hybrid vectors and said hosts. The present invention also provides a more cost-effective process for the production of two-chain hybrid PA molecules as the single-chain products of the recombinant DNAs can be cleaved in vitro by suitable proteolytic enzymes, such as plasmin. Detailed description of the invention

DETAILED DESCRIPTION OF THE INVENTION

The invention relates especially to a single-chain hybrid PA having an amino acid sequence composed of at least two subsequences corresponding in amino acid identity and number to subsequences of human t-PA and of human u-PA.

Like other serine proteases involved in the fibrinolytic and coagulation system of the blood u-PA and t-PA have large non-catalytic segments assembled in chain A attached to the catalytic region (chain B). The non-catalytic A-chain of t-PA can be subdivided into discrete domains: the "finger"

domain, "growth factor" domain and two "kringle" structures while the A-chain of u-PA is composed of a "growth factor" domain and one "kringle" [structure for reference see L. Patthy, Cell 41, 657–663 (1985)]. The catalytic site of the B-chains is formed by His, Asp, Set residues at positions 322, 371 and 478 (t-PA) and 204, 255 and 356 (u-PA), respectively, and is essential for fibrinolytic activity.

A protein domain is a structural and/or functional entity within the overall structure of the entire protein. For example, in the t-PA A-chain four domains finger-, growth factor- and two kringle domains) are aligned In series. The borders of the domains are best defined by the positions of exon-intron junctions in the corresponding DNA sequence (L. Patthy, above). However, for practical reasons the minimal size of each domain has been defined by the amino acid sequence between the first and the last cysteine residue within each domain which are likely to be involved in S—S bridge formation. Amino acids before and after these cysteine residues from adjacent domains are defined as junction sequences (J). The positions of exon-intron junctions (see above) are within these J regions.

Thus, single-chain t-PA can be represented by the following formula:

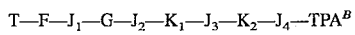

$$T—F—J_1—G—J_2—K_1—J_3—K_2—J_4—TPA^B$$

in which T represents the N-terminal part comprising amino acids 1 to 5, F is the finger domain comprising amino acids 6 to 43, G is the growth factor domain comprising amino acids 51 to 84, $K_1$ is the kringle 1 structure comprising amino acids 92 to 173, $K_2$ is the kringle 2 structure comprising amino acids 180 to 261, $TPA^B$ is the catalytic serine protease region comprising amino acids 307 to 527 and $J_1$ (amino acids 44 to 50), $J_2$ (amino acids 85 to 91), $J_3$ (amino acids 174 to 179) and $J_4$ (amino acids 262 to 306) are junction sequences joining the domain segments.

Single-chain u-PA can be represented by the following formula:

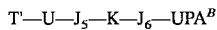

$$T'—U—J_5—K—J_6—UPA^B$$

in which T' represents the N-terminal part comprising amino acids 1 to 12, U is the growth factor domain comprising amino acids 13 to 42, K is the kringle structure comprising amino acids 50 to 131, $UPA^B$ is the catalytic serine protease region comprising amino acids 189 to 411 and $J_5$ (amino acids 43 to 49) and $J_6$ (amino acids 132 to 188) are junction sequences joining the domain segments.

The junction sequences $J_4$ and $J_6$ each include the activation (processing) site and, N-terminal thereto, a cysteine residue which is involved in a sulphur-sulphur bridge to the catalytic (B-chain) region.

It has surprisingly been found that single-chain hybrid PAs comprising the catalytic serine protease region of one PA ($TPA^B$ or $UPA^B$) attached to an amino acid sequence containing all or discrete A-chain domains of the other PA or discrete domains of both PAs exhibit valuable pharmacological properties.

Accordingly, the invention relates to a single-chain hybrid PA comprising an amino acid sequence containing all or discrete A-chain domains of human u-PA or discrete A-chain domains of human u-PA and human t-PA, linked in series to the catalytic region of human t-PA ($TPA^B$) and to a single chain hybrid PA comprising an amino acid sequence containing all or discrete A-chain domains of human t-PA or discrete A-chain domains of human t-PA and u-PA, linked in series to the catalytic region of human u-PA ($UPA^B$).

In a preferred embodiment the hybrid PAs according to the invention contain the catalytic region of human u-PA ($UPA^B$).

In particular, the invention relates to single-chain PAs comprising an amino acid sequence selected from the group consisting of an amino acid sequence containing all of the A-chain domains of human t-PA, an amino acid sequence containing discrete A-chain domains of human t-PA, such as the finger domain or a kringle, especially the kringle 2, domain of human t-PA, and an amino acid sequence containing two, three or four A-chain domains of human t-PA and/or human u-PA, especially two or three domains of human t-PA or two or three domains of human u-PA and human t-PA, such as the finger, growth factor and kringle 2 domains of human t-PA, the finger and kringle 2 domains of human t-PA or the u-PA growth factor and t-PA kringle 2 domains, which amino acid sequence is linked in series to the catalytic region of human u-PA, and to a single-chain PA comprising an amino acid sequence containing the u-PA growth factor and t-PA kringle 2 domains which amino acid sequence is linked in series to the catalytic region of human t-PA.

Preferably, the hybrid PA amino acid sequence starts with the N-terminal sequence of t-PA (T, amino acids 1 to 5) or u-PA (T', amino acids 1 to 12) or starts with any junction sequence naturally N-terminally linked to the first domain of the hybrid PA or with a fragment of such a junction sequence which fragment preferably has at least five amino acid residues.

In the hybrid PAs according to the invention the A-chain domains are connected via natural junction sequences (e.g. $J_1$, $J_2$, $J_3$, and $J_5$), fused junction sequences or hybrid junction sequences or fragments thereof. Thus, a first domain is linked to a second domain by the junction sequence naturally occurring at the C-terminus of the first domain, by the junction sequence naturally occurring at the N-terminus of the second domain, by a fused junction sequence composed of said junction sequences or by fragments thereof.

The A-chain domains of the hybrid PAs according to the invention are linked to the B-chain serine protease region ($TPA^B$ or $UPA^B$) by a junction sequence selected from the group consisting of the junction sequence $J_4$ linking the A-chain to the B-chain in human t-PA, the junction sequence $J_6$ linking the A-chain to the B-chain in human u-PA and a hybrid sequence composed of subsequences of said junction sequences wherein said junction sequence includes a processing site capable of being cleaved by plasmin and, N-terminally thereto, a cysteine residue which can participate in a sulphur-sulphur bridge to the catalytic B-chain region, the junction sequence preferably having at least fourty and up to 60 amino acid residues.

Most preferred is the junction of the domains at a position which is defined by the exon-intron junctions on the corresponding DNA. The junction of the A-chain to the B-chain is most preferably at the activation site.

In particular, the invention relates to a single chain hybrid plasminogen activator selected from the group consisting of such a hybrid plasminogen activator comprising the A-chain of u-PA or an A-chain essentially consisting of the u-PA growth factor and the t-PA kringle 2 domains linked in series to the catalytic region (B-chain) of t-PA, and a hybrid plasminogen activator comprising the A-chain of t-PA, an A-chain essentially consisting of the finger domain of t-PA, an A-chain essentially consisting of the u-PA growth factor and t-PA kringle 2 domains, an A-chain essentially consisting of the t-PA finger and kringle 2 domains or an A-chain essentially consisting of the t-PA finger, growth factor and kringle 2 domains said A-chain being linked in series to the catalytic region (B-chain) of u-PA, wherein the A-chain is linked to the B-chain via a junction sequence comprising an activation site and a cysteine residue capable of forming a sulphur-sulphur bond to the B-chain.

In particular, the invention relates likewise to a single chain hybrid plasminogen activator comprising an A-chain essentially consisting of the t-PA kringle 2 domain linked to the catalytic region (B-chain) of u-PA at the activation site.

Especially preferred is a single chain hybrid plasminogen activator selected from the group consisting of such a hybrid plasminogen activator comprising an A-chain essentially consisting of the u-PA growth factor domain and the t-PA kringle 2 domain linked in series to the catalytic region (B-chain) of t-PA, and a hybrid plasminogen activator comprising an A-chain essentially consisting of the t-PA kringle 2 domain or of the t-PA finger and kringle 2 domains linked in series to the catalytic region (B-chain) of u-PA, wherein the junction between the A-chain domain(s) and the B-chain is at the activation site.

Preferred hybrid PAs according to the invention are
UPA$^A$TPA$^B$(BC)=[uPA(1–158)-tPA(276–527)],
UPA$^A$TPA$^B$(BR)=[uPA(1–131)-tPA(263–527)],
TPA$^A$UPA$^B$(BC)=[tPA(1–275)-uPA(159–411)],
TPA$^A$UPA$^B$(BC)=[tPA(1–262)-uPA(132–411)],
TPA$^A$UPA$^B$(BR)=[tPA(1–262)-uPA(132–411)],
UK$_2$UPA$^B$(BR)=[uPA(1–44)-tPA(176–261)-uPA134–411)],
FUPA$^B$(BC)=[tPA(1–49)-tPA(262–275)-uPA(159–411)],
FUPA$^B$(BR)=[tPA(1–49)-uPA(134–411)],
FK$_2$UPA$^B$(BC)=[tPA(1–49)-tPA(176–275)-uPA(159–411)],
FK$_2$UPA$^B$(BR)=[tPA(1–49)-tPA(176–262)-uPA(132–411)],
UK$_2$TPA(BC)=[uPA(1–44)-tPA(176–527)],
K$_2$UPA$^B$(BC)=[tPA(1–3)-tPA(176–275)-uPA(159–411)],
FGK$_2$UPA$^B$(BC)=[tPA(1–86)-tPA(176–275)-uPA(156–411)] and
FGK$_2$UPA$^B$(BR)=[tPA(1–86)-tPA(176–262)-uPA(132–411)], in which UPA$^A$ is the A-chain of u-PA, TPA$^A$ is in the A-chain of t-PA, UPA$^B$ is the B-chain of u-PA, TPA$^B$ is the B-chain of t-PA, U refers to the growth factor domain of u-PA. K$_2$ refers to the kringle 2 domain of t-PA. F refers to the finger domain of t-PA. G refers to the growth factor domain of t-PA. (BC) indicates that the junction between the A-chain domain(s) and the B-chain is at the activation site and (BR) indicates that the A-chain domain(s) is (are) linked to the B-chain via the junction sequence naturally attached to the B-chain including the activation site and, N-terminally thereto, the cysteine residue which is involved in a sulphur-sulphur bridge to the B-chain. The numbers refer to the amino acid sequences taken from u-PA and t-PA, respectively. For example, UK$_2$UPAB(BR)= [uPA(1–44)-tPA(176–261)-uPA(134–411)] designates a single-chain hybrid plasminogen activator consisting of amino acids 1–44 (growth factor domain, U) of u-PA and amino acids 176–261 (kringle 2 domain, K$_2$) of t-PA linked in a linear fashion to amino acids 134–411 (B-chain UPA$^B$) of u-PA.

Especially preferred are hybrid plasminogen activators TPA$^A$UPA$^B$(BC), FUPA$^B$(BC), FGK$_2$UPA$^B$(BC) and, in particular, UK$_2$TPA$^B$(BC), FK$_2$UPA$^B$(BC) and K$_2$UPA$^B$(BC).

The invention relates furthermore to mutants of the hybrid PAs according to the invention in which at least one, preferably all, of the N-glycosylation sloes is (are) modified such that glycosylation cannot take place at this (these) site(s).

It is well established that a prerequisite for N-linked glycosylation in mammalian cells is the occurrence of the tripeptide sequence -Asn-L-Ser(or Thr)- wherein Asn is the acceptor and L can be any of the 20 genetically encoded amino acids except proline or aspartic acid which prevent glycosylation. There are three sites for N-glycosidic linkage in the t-PA molecule (the numbers refer to the position of Asn in ;he amino acid sequence of c-PA, cf. FIG. 1 of the accompanying drawings): -Asn$^{117}$-Ser-Ser- (present in kringle 1), Asn$^{184}$-Gly-Ser- (present in kringle 2), and Asn$^{448}$-Arg-Thr (present in the t-PA B-chain). The unique N-linked glycosylation site of u-PA is in the B-chain (Asn$^{302}$-Ser-Thr, cf. FIG. 3). It is obvious that hybrid PAs comprising the t-PA kringle 1, t-PA kringle 2, the B-chain of t-PA and/or the B-chain of u-PA also include the respective N-linked glycosylation sites.

In order to prevent Elycosylation at individual (one or more of the) N-Elycosylation sites the tripepride sequences recognised as signals for N-Elycosylation have to be altered. Replacement of the Asn and/or Ser (or Thr) residues in the above tripepride sequences by any other amino acid would abolish formation of glycosidic linkages at these sites. For convenience, modification of the N-glycosylation sites is not done at the protein level. Instead, it is advantageous to modify the gene coding for the hybrid PA in such a way that upon expression of said modified gene by a host a mutant hybrid PA is produced in which one or more of the N-glycosylation sites are altered in such a way that glycosylation cannot take place at these sites. It is preferred to modify all of the N-glycosylation sites occurring in the hybrid PAs according to the invention.

Especially, asparagine is substituted with valine, leucine, isoleucine, alanine or, in particular, glutamine, and serine or threonine with saline, methionine or in particular, alanine.

Especially preferred are the modified hybrid PAs FUPA$^B$(Gln302)(BC)=[tPA(1–19)-tPA(262–275)-uPA(159–301, Gln, 303–411)].
FK$_2$(Ala186)UPA$^B$(Gln302)(BC)=[tPA(1–49)-tPA(176–185, Ala, 187–275)-uPA(159–301, Gln, 303–411)], UK$_2$(Ala186)TPAB(Ala450)(BC)=[tPA(1–44)-tPA(176–185, Ala, 187–449, Ala, 451–527)], K$_2$(Ala186)UPA$^B$(Gln302)(BC)=[tPA(I-3)-tPA(176–185, Ala, 187–275)-uPA(159–301, Gln, 303–411(],
FK$_2$UPA$^B$(Ala186)UPA$^B$(Gln302)(BC)- (tPA(1–86)-tPA [176–185, Ala, 187–275)-uPA(159–301, Gln, 303–411)], and furthermore FK$_2$UPA$^B$(Gln302)(BC)=[tPA(1–49)-tPA(176–275)-uPA(159–301, Gln, 303–411)], K$_2$UPA$^B$(Gln302)(BC)-[tPA(1-3)-tPA(176–275)-uPA(159–301, Gln, 303–411)], UK$_2$TPA$^B$(Ala450)(BC)-[uPA(1–44)-tPA(176–449, Ala, 451–527)], and FGK$_2$UPA$^B$(Gln302)(BC)=[tPA(1–86)-tPA(176–275)-uPA(159–301, Gln, 303–411)].

The hybrid PAs and mutants thereof according to the invention can be prepared by recombinant DNA technique comprising, for example, culturing a transformed host expressing the hybrid PA protein or mutant thereof under conditions which allow expression thereof and isolating the hybrid PA protein and mutant hybrid PA protein, respectively. More specifically, the desired compounds are manufactured by a) preparing a DNA coding for a hybrid PA protein or a mutant thereof or chemically synthesizing such a DNA, b) incorporating the DNA into an appropriate expression vector, c) transferring the obtained hybrid vector into a recipient host, d) selecting the transformed host from untransformed hosts, e.g. by culturing under conditions under which only the transformed host survives, e) culturing the transformed host under conditions which allow expression of the hybrid PA protein, and f) isolating the hybrid PA protein or mutant thereof.

The steps involved in the preparation of the hybrid PA proteins by recombiant DNA technique will be discussed in more detail hereinbelow.

DNAs coding for hybrid PA proteins

The invention relates to DNAs having a sequence coding for a hybrid PA which is composed of at least two subsequences corresponding in amino acid identity and number to subsequences of human u-PA and human t-PA, or coding for a mutant thereof. In particular, the invention relates to DNAs having a sequence coding for any of the hybrid PA proteins and mutants thereof mentioned hereinbefore as being preferred.

Preferably the DNAs according to the invention have flanking sequences at their termini. In particular, these flanking sequences include suitable restriction sites which allow integration of the DNAs into suitable vectors.

Furthermore, the DNAs according to the invention include the signal sequence of u-PA or t-PA attached to the first codon of the mature hybrid PA coding sequence. When expressed in yeast cells the DNAs according to the invention may alternatively include a yeast signal sequence, such as the signal sequence naturally linked to the yeast promoter used, especially the PHO5 or invertase signal sequence.

Preferably, the nucleotide sequences of the DNA subsequences are identical to nucleotide sequences found in u-PA cDNA and t-PA cDNA, respectively. However, due to the degeneracy of the genetic code the nucleotide sequences may differ provided that the resulting amino acid subsequences remain unchanged. In KiNAs coding for a mutant hybrid PA at least one codon encoding an amino acid essential for N-glycosylation of the hybrid PA protein is replaced by another codon encoding a different amino acid which abolishes the recognition site for N-glycosylation.

The nucleotide sequences of u-PA cDNA and t-PA cDNA are known [cf. W. E. Holmes et. al., Biotechnology 3, 923–929 (1985); D. Pennica et al., Nature 301, 214–221 (t983)]. Furthermore, the complete nucleotide sequences of the genomic u-PA and t-PA genes including all introns and exons have been established [cf. A. Riccio et al., Nucl. Acids Res. 13, 2759–2771 (985): S. J. Friezner-Degen et al., J. Biol. Chem. 261, 6972–6985 (1986)].

Knowing the cDNA and genomic DNA sequences of u-PA and t-PA the DNAs according to the invention can be made by methods known in the art. The methods for making these DNAs include chemically synthesizing the DNAs or preparing fragments coding for polynucleotide subsequences of u-PA cDNA and t-PA cDNA and regulating them in the predetermined order optionally including one or more, such as two or three, mutation steps.

The DNAs coding for mutant hybrid PAs according to the invention can be manufactured by methods known in the art. The methods for the manufacture of these DNA include excising a portion of the DNA comprising the codon for the undesired amino acid residue from the parental hybrid PA gene and replacing it with a DNA segment wherein said codon has been substituted with a deoxyribonucleotide triplet coding for the desired amino acid residue, or accomplishing the deoxyribonucleotide substitution by means of site-directed mutagenesis.

The chemical synthesis of DNA is well-known in the art and makes use of conventional techniques. Appropriate techniques have been compiled by S. A. Narang [Tetrahedron 3–9, 3 (1983)]. In particular, the methods described in European Patent Application No. 146,785 may be used and are herein incorporated by reference.

Another approach for the synthesis of the DNAs according to the invention consists in excising suitable restriction fragments coding for polynucleotide subsequences of u-PA and t-PA from u-PA cDNA and t-PA cDNA (or genomic u-PA DNA or t-PA DNA) and using these fragments for the preparation of the whole hybrid PA structural gene. Two strategies can be applied. With either strategy care has to be taken that the fusion of the fragments occurs at sites between the domains in order to keep the latter intact. The first strategy makes use of suitable restriction sites. When an appropriate restriction site is available at the predetermined junction site(s) in both the u-PA and t-PA DNAs the DNAs are digested with the corresponding restriction endonuclease and the fragments are joined by blunt-end or staggered-end ligation (depending on the restriction endonuclease chosen). Alternatively, useful restriction sites can be introduced by, for example, site-directed mutagenesis [cf. M. J. Zoller et al., Methods Enzymol 100, 468 (1983)] taking care that the mutated DNA does not result in an altered amino acid sequence. Especially preferred natural or artificially introduced restriction sites are those which separate the DNAs coding for the A- and B-chains or DNAs coding for the discrete domains contained in the A-chains- In this way, hybrid DNAs can be produced which code for hybrid PAs having the desired junction between the A-chain domains and the catalytic serine protease region. The second strategy emanates from the hypothesis that domain borders are best defined by the position of the exon-intron junctions in the genomic DNAs [cf. L. Patthy, Cell 41, 657–663 (1985)], i.e. positions in the cDNAs where introns had been spliced. Since these positions rarely coincide with restriction sites, a scheme is adopted which can be followed for any new construction: in a first step convenient restriction fragments that code for the specific domain(s) but also contain additional DNA sequences beyond the anticipated fusion point (up to several hundred base pairs) are ligated and subcloned in bacteriophage m13. In a second step the excess DNA sequences are looped out by in vitro mutagenesis (Zoller et al., supra). This procedure allows precise in frame fusions at any predetermined nucleotide position and is therefore preferred.

For the preparation of mutant hybrid PAs, excision of a portion of the mature hybrid DNA may be effected by using restriction enzymes. A prerequisite of this method is the availability of appropriate restriction sites in the vicinity of the codon to be altered. A small restriction fragment containing the codon for an undesired amino acid is removed by endonuclease cleavage. A corresponding double stranded DNA sequence is prepared, for example by means of chemical synthesis, in which triplets coding for the desired amino acid are used. The DNA fragment is ligated in the proper orientation to the remaining large fragment to yield a double stranded DNA sequence coding for a mutant hybrid. For convenience and in order to facilitate handling of the hybrid gene the latter is advantageously contained in a greater DNA segment provided with appropriate linkers which allow insertion and cloning of the segment in a cloning vector.

in a preferred embodiment of the present invention the preparation of DNAs coding for a mutant hybrid PA is effected by site-directed mutagenesis. This method is an in vitro mutagenesis procedure by which a defined site within a region of cloned DNA can be altered [cf. the review articles of M. J. Zoller and M. Smith, Methods Enzymol.

100, 468 (1983); D. Botstein and D. Shortle, Science 229, 1193 (1985)]. Mutagenesis can either be effected on the complete hybrid PA gene or on functional parts thereof containing the codon for the undesired amino acid(s). After mutagenesis, the mutated functional part is linked to the other parts of the hybrid PA to yield the mutant hybrid PA.

The method of mutating the hybrid PA gene or functional part thereof is characterized in that the single-stranded gene or a single-stranded DNA comprising the PA gene or part thereof is hybridized to an oligodeoxy-ribonucleotide primer which is complementary to the region of the hybrid gene to be mutated except for mismatch(es) that direct(s) the mutation, the hybridized oligodeoxyribonucleotide is used as a primer to initiate the synthesis of the complementary DNA strand, the resulting (partially) double-stranded DNA is transformed into a recipient microorganism strain, the microorganism strain is cultivated and transformants containing DNA with the modified (mutant) hybrid PA gene are selected.

Hybrid vectors concanine hybrid PA DNA

The invention relates to hybrid vectors comprising a DNA coding for a hybrid PA which is composed of at least two subsequences corresponding in amino acid identity and number to subsequences of human u-PA and human t-PA, or coding for a mutant thereof, and to processes for the preparation thereof.

The vector is selected depending on the host cells envisaged for transformation. In principle, all vectors which replicate and express the desired polypeptide gene according to the invention in the chosen host are suitable. Examples of suitable hosts are eukaryotes, which are devoid of or poor in restriction enzymes or modification enzymes, such as yeasts, for example *Saccharmoyces cerevisiae*, for example *S. cerevisiae* GRF18, and furthermore mammalian cells, in particular established human or animal cell lines, e.g. myeloma cells, human embryonic lung fibroblasts L-132, COS cells, LTK cells, human malignant melanoma Bowes cells, HeLa cells, SV-40 virus transformed kidney cells of African green monkey COS-7 or chinese hamster ovary (CHO) cells and variants thereof. The above mammalian cells and strains of *Saccharmoyces cerevisiae*, for example *S. cerevisiae* GRF18, are preferred as the host microorganism.

a. Vectors for use in yeast

Vectors which are suitable for replication and expression in yeast contain a yeast replication origin and a selective genetic marker for yeast. Hybrid vectors which contain a yeast replication origin, for example chromosomal autonomously replicating segment (ars), are retained extrachromosomally within the yeast cell after the transformation and are replicated autonomously. Furthermore, hybrid vectors which contain sequences homologous to the yeast 2μ plasmid DNA can be used. Such hybrid vectors will get integrated by recombination into 2 μ plasmids already existing within the cell, or replicate autonomously. 2 μ sequences are particularly suitable for plasmids with a high transformation frequency and permit high copy numbers.

Suitable marker genes for yeast are, in particular, those which impart antibiotic resistance to the host or in the case of auxotrophic yeast mutants, genes which complement host lesions. Corresponding genes impart, for example, resistance towards the antibiotic G418 or provide for prototrophy in an auxotrophic yeast mutant, for example the URA3, LEU2, HIS3 or TRP1 gene. Yeast hybrid vectors furthermore preferably contain a replication origin and a marker gene for a bacterial host, in particular *E. coli,* so that the construction and cloning of the hybrid vectors and their intermediates can take place in a bacterial host.

Expression control sequences which are suitable for expression in yeast are, for example, those of well expressed yeast genes. Thus, the promoters of the TRP1 gene, the ADHI or ADHII gene, acid phosphatase (PM03 or PH05) genes, isocytochrome gene or a promoter of the glycolysis genes, such as the promoter of the enolase, glyceraldehyde-3-phosphate dehydrogenase (GAPDM), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomeras, phosphoglucose isomerase, invertase and glucokinase genes, can be used. Preferred vectors of the present invention contain promoters with transcriptional control, e.g. the promotecs of the PHO5 and ADH II genes, which can be turned on or off by variation of the growth conditions. For example, the PHO5 promoter can be repressed or derepressed solely by increasing or decreasing the concentration of inorganic phosphate in the medium.

Preferably, the yeast hybrid vectors according to the present invention comprise also the 3' flanking sequence of a yeast gene which contains the proper signals for transcription termination and polyadenylation. Suitable 3' flanking sequences are for example those of the gene naturally linked to the promoter used, such as the 3' flanking sequence of the yeast PHO5 gene.

b. Vectors for use in mammalian cells vectors for replication and expression in mammalian cells are frequently provided with DNA from viral origin, e.g. from simian virus 40 (SV 40), Rous sarcoma virus (RSV), adenovirus 2, bovine papilloma virus (BPV), papovavirus BK mutant (BKV), or mouse or human cytomegalovirus (MCMV and HCMV, respectively).

Expression control sequences which are suitable for use in mammalian cells include, inter alia, the early and late promoters of SV40, the major late promoter of adenovirus, the promoter of the murine metallothionein gene and the enhancer-promoter region of the mouse or human cytomegalovirus major immediate-early gene, the human immunoglobulin enhancer-promoter region, the human a globin promoter optionally combined with the SV40 enhancer and promoters derived from the heat shock genes Suitable marker genes for mammalian cells are, for example, the neo and ble genes from transposon Tn5 which confer resistance to the antibiotic G418 and to bleomycin-type antibiotics, respectively, the *E. coli* gene for hygromycin-B resistance, the dihydrofolate ceductase gene (dhfr) from mammalian cells or *E. coli* which changes the phenotype of DHFR$^-$ cells into DHFR$^+$ cells and/or confer resistance to methotrexate, and the thymidine kinase gene of herpes simplex virus which makes TK$^-$ cells phenotypically TK$^+$ cells.

Preferably, the hybrid vectors for mammalian cells contain the 3' untranslated region of a mammalian gene containing signals for proper transcription termination and polyadenylation, such as, for example, the 3' flanking region of the B-globin gene. Advantageously, the regions flanking the polypeptide coding region include one or more native introns having the appropriate splicing signals at their termini. Such additions are deemed necessary as cDNAs and prokaryotic DNAs such as the above selection genes, generally lack such transcription and processing signals.

Preferably, such vectors contain an origin of replication and an anti biotic resistance gene for propagation in *E. coli.*

A mammalian origin of replication may be provided either by including in the construction of the vector a eukarvotic origin, such as derived from SV40 or from another viral source, or may be provided by the host cell chromosome upon integration of the vector into the host cell chromosome.

The preferred hybrid vectors for use in mammalian cells comprise the hybrid PA or mutant hybrid PA cDNA operably flanked on the upstream side by the murine cytomegalovirus major immediate-early gene enhancer promoter and on the downstream side by the 3' end of the rabbit beta globin gene, which includes the second intron with its appropriate splicing signals and a polyadenylation sequence. Further they contain the sequences encoding the neomycin resistance gene from transposon Tn5 or optionally from Tn9 or the sequences encoding hygromycin phosphotransferase flanked on its upstream side sequentially by the early promoter from SV40 virus which also includes the SV40 origin of replication and the natural promoter of the Tn5 neogene, and on its downstream side by a segment of the SV40 early gene including the small t-antigen splicing and polyadenylation signals. The whole construct is cloned into a fragment of E. coli plasmid pBR322, which includes the plasmid origin of replication, the ampicillin resistance gene, but lacks so-called poison-sequences inhibiting SV40-mode DNA replication in mammalian cells. Optionally, a gene encoding dihydrofolate reductase (DHFR) is included in the vector, preferentially the modular DHFR gene described by R. J. Kaufman et al. [Mol. Cell. Biol. 2, 1304–1319 (1982)] is used. This modular DHFR gene consists of, sequentially, the major late promoter of adenovirus type 2, a fragment of a immunoglobulin gene, the coding portion of a murine DHFR cDNA and the SV40 early polyadenylation site.

The novel preferred hybrid vectors for use in mammalian cells constitute a progress in the art. They are superior compared to the hitherto known vectors in that they contain the strong expression signals for the cloned cDNA located in the mouse cytomegalovirus immediate-early promoter/enhancer and in the beta-globin splicing/polyadenylation sequences in an environment which allows high-level expression in an extremely wide variety of vertebrate cell types. More specifically, the vectors can be used (a) to express cDNAs transiently in normal, i.e. not SV40-transformed, tissue culture cell lines, but (b) even better at higher copy number in primate cells expressing SV40 T-antigen, thus allowing the vector to replicate via its SV40 origin of replication, but also (c) to express such cloned cDNA stably in normal tissue culture cell lines, where the vector can integrate into the host cell chromosome and (d) even better, because of the higher copy number, when the vector is introduced into SV40 T-antigen producing primate cell lines, where the vector can replicate episomally.

The enhancer-promoter region of MCMV comprises, for example, a DNA starting at nucleotides −835 to −443 and ending at nucleotide +50 (counted from the mRNA start) of the 5' region of the MCMV major immediate-early gene. The preferred enhancer-promoter region of MCMV comprises nucleotides −542 to +50.

The 3' flanking region of rabbit B-globin gene consists of the second half of the rabbit beta-globin gene [P. Dierks et al., Proc. Natl. Acad. Sci. USA 78, 1411–1415 (1981); A. van Ooyen et al., Science 206, 337–344 (1979)] starting in the second exon, preferably at the BamHI site, thus including the second intron with the signals for splicing at its flanking sequences, and terminating behind the polyadenylation signals, preferably of the BglII site located 1.2 kb behind the above BamHI site.

The SV40 origin of replication is contained, for example, in the HindIII-SphI fragment of the vital DNA [nucleotides 5171 to 128, origin=position 1; Tooze J. (ed.) DNA Tumor Viruses, Part. 2, 2nd Edition, Cold Spring Harbor Laboratory, Cold Spring Harbor N.Y. 1982]. The preferred embodiment is, however, the HindIII-HpaII fragment (nucleotides 5171 to 346), which in addition to the origin of replication also contains the viral early enhancer/promoter useful to promote transcription of the selection gene of the vector.

The neomycin gene is cloned behind a promoter active in tissue culture cells, preferably the SV40 early promoter as located on the HpaII-HindIII fragment mentioned above. The coding sequences of the neomycin gene are contained, for example, on a BglII-SmaI fragment from transposon Tn5 [E. Beck et el., Gene 19, 327–336 (1982); P Southern et al J. Mol. Appl. Genet. ! , 327–341 (1982); F. Colbère-Garapin et al., J. Mol. Biol. 150, 1–14 (1981)]. It is preferred to equip the neomycin gene with a second promoter allowing also transcription in E. coli . For example, the natural promoter of the Tn5 neomycin gene contained preferably on a HindIII-BglII fragment can be placed behind the eukaryotic promoter in front of the neo coding sequences (Southern et al., supra) or further upstream in front of the eukaryotic promoter (Colbère-Garapin et al., supra). To be expressed in tissue culture cells the bacterial neogene must be followed by a polyadenylation signal, preferably a portion of the SV40 t antigen gene also containing splicing signals. The coding sequence of the neomycin phosphotransferase, especially the BglII-SmaI part of the Tn5 fragment mentioned above, can also be replaced by the coding sequence of the hygromycin B phosphotransferase preferentially in the form of the BamHI fragment of plasmid pLG89 [L. Gritz et el., Gene 25, 179–188 (1983)], which can be most conveniently inserted into pSVd [Luedin et el., EMBO-J. 6, 109–114 (1987)], a derivative of pSV2911neo in which a BglII linker is introduced at the SmaI site in the vector.

Another preferred selection gene uses the coding sequence for the enzyme dihydrofolate reductase, such as in $pSv_2dhfr$ (ATCC 37145), which allows not only selection of transformed cell lines but also amplification of the plasmid associated DNA sequence, frequently with a proportional increase of production of the plasmid-encoded proteins according to the invention.

The fragment derived from E. coli plasmid pBR322 includes the pBR322 origin of replication and the ampicillin resistance gene. The fragment is preferably taken from a pBR322 derivative, such as pSVOd [P. Mellon et el., Cell 2–7,279–288 (1981)] in which the so-called poison sequence which would inhibit the SV40 T antigen-driven replication of the vector, is removed.

In a preferred embodiment, the present invention relates to hybrid vectors capable of replication and phenotypical selection in a eukaryotic host strain comprising a promoter and a DNA encoding a hybrid PA or mutant hybrid PA, said DNA being positioned together with transcription start and termination signals as well as translation start and stop signals in said hybrid vector under the control of said promoter such that in a transformed host it is expressed to produce the protein.

The hybrid vectors according to the invention are prepared by methods known in the art, for example by linking the DNA segments containing the promoter, the hybrid PA or mutant hybrid PA coding region, the 3' flanking sequence and the vector DNA.

Various techniques may be used to link DNA segments in vitro. Blunt ends (fully base-paired DNA duplexes) produced by certain restriction endonucleases may be directly ligated with T4 DNA ligase. More usually, DNA segments are linked through their single-stranded cohesive ends and covalently closed by a DNA ligase, e.g. T4 DNA ligase. Such single stranded "cohesive termini" may be formed by cleaving DNA with another class of endonucleases which produce staggered ends (the two strands of the DNA duplex are cleaved at different points at a distance of a few nucleotides). Single strands can also be formed by the addition of nucleotides to blunt ends or staggered ends using terminal transferase ("homopolymeric tailing") or by simply chewing back one strand of a blunt-ended DNA segment with a suitable exonuclease, such as λ exo-nuclease. A further approach to the production of staggered ends consists in ligating to the blunt-ended DNA segment a chemically synthesized linker DNA which contains a recognition site for a staggered-end forming endonuclease and digesting the resulting DNA with the respective endo-nuclease. The components of the hybrid vectors according to the invention are linked together in a predetermined order to assure proper function.

Hosts transformed with hybrid vectors containing hybrid PA DNA

Another aspect of the present invention involves eukaryotic host organisms transformed with hybrid vectors comprising a DNA coding for a hybrid PA which is composed of at least two subsequences corresponding in amino acid identity and number to subsequences of human u-PA and human t-PA or coding for a mutant thereof, and mutants of said host, and processes for the preparation thereof.

Examples of suitable eukaryotic hosts are those specified above, especially strains of yeast and mammalian cells. Mutants of transformed host organisms include especially mutants which are poor in hybrid PA or mutant hybrid PA degrading proteases and give higher yields in hybrid PA and mutant hybrid PA, respectively.

The process for the preparation of the transformed eukaryotic hosts comprises transforming or transfecting an eukaryotic host with an expression vector comprising a DNA of the invention regulated by an expression control sequence.

The transformation of the eukaryotic host cells is accomplished by methods known in the art. For example, the transformation of yeast with the hybrid vectors may be accomplished according to the method described by Hinnen et al [Proc. Natl. Acad. Sci. USA 75, 1919(1978)]. This method can be divided into three steps:

(1) Removal of the yeast cell wall or parts thereof.

(2) Treatment of the "naked" yeast cells (spheroplasts) with the transforming DNA in the presence of PEG (polyethyleneglycol) and $Ca^{2+}$ ions.

(3) Regeneration of the cell wall and selection of the transformed cells in a solid layer of agar.

Preferred methods:

ad (1): The yeast cell wall is removed enzymatically using various preparations of glucosidases, such as snail gut juices (e.g. Glusulase® or Helicase®) or enzyme mixtures obtained from microorganisms (e.g. Zymolyase®) in osmotically stabilized solutions (e.g. 1M sorbitol).

ad (2): The yeast spheroplasts aggregate in the presence of PEG and local fusions of the cytoplasmic membranes are induced. The generation of "fusion-like" conditions is crucial and many transformed yeast cells become diploid or even triploid during the process of transformation. Procedures which allow selection of fused spheroplasts can be used to enrich for transformants, i.e. transformed cells can easily be screened for among preselected fusion products.

ad (3): Since yeast cells without cell wall do not divide the cell wall has to be regenerated. This regeneration is conveniently done by embedding the spheroplasts into agar. For example, molten agar (about 50° C.) is mixed with the spheroplasts. Upon cooling the solution to yeast growth temperatures (about 30° C.), a solid layer is obtained. This agar layer is to prevent rapid diffusion and loss of essential macromolecules from the spheroplasts and thereby facilitates regeneration of the cell wall. However, cell wall regeneration may also be obtained (although at lower efficiency) by plating the spheroplasts onto the surface of preformed agar layers.

Preferably, the regeneration agar is prepared in a way to allow regeneration and selection of transformed cells at the same time. Since yeast genes coding for enzymes of amino acid biosynthetic pathways are generally used as selective markers (supra), the regeneration is preferably performed in yeast minimal medium agar. If very high efficiencies of regeneration are required the following two step procedure is advantageous: (1) regeneration of the cell wall in a rich complex medium, and (2) selection of the transformed cells by replica plating the cell layer onto selective agar plates.

The introduction of hybrid vectors into mammalin cells is done by transfection in the presence of helper compounds, e.g. diethylaminoethyldextran, dimethyl sulfoxide, glycerol, polyethylene glycol or the like, or as co-precipitates of vector DNA and calcium phosphate. Further suitable methods include direct microinjection of vector DNA into the cell nucleus and electroporation, i.e. introduction of DNA by a short electric pulse increasing the permeability of cell membranes. The subsequent selection of transfected cells can be done using a selection marker which is either covalently integrated into the expression vector or added as a separate entity. The selection markers include genes which confer resistance to antibiotics or genes which complement a genetic lesion of the host cell (supra).

One preferred selection system makes use of cells lacking dihydrofolate reductase ($DHRF^-$), e.g. CHO cells, which absolutely require thymidine, glycine and purines for growth unless an exogenous DHFR gene is supplied. On introduction of a vector containing the hybrid PA gene and additionally a DHFR gene into suitable $DHFR^-$ cells, e.g. CHO cells, transformed cells are selected by increasing the concentration of the anti-folate drug methotrexate in the medium.

Particularly preferred is a selection method wherein suitable mammalian cells, e.g. CHO cells, are treated with co-precipitates of vector DNA containing the hybrid PA gene and a gene coding for antibiotics resistance, e.g. resistance to G-418, and calcium phosphate. The transformed cells are selected by culturing in the presence of the corresponding antibiotics, e.g. G-418, and/or by screening for hybrid PA expression.

The transformed host organisms according to the invention can be improved in the production of hybrid PAs or mutant hybrid PAs by mutation and selection applying methods known in the art. The mutation can be effected, for example, by U.V. irradiation or suitable chemical agents. Especially preferred is the production of protease-deficient mutants, especially yeast mutants, in order to avoid proteolytic degradation of the produced hybrid PA and mutant hybrid PA, respectively.

Cultivation of transformed host cells

The invention concerns furthermore a method for the production of single-chain hybrid PAs having an amino acid sequence composed of at least two subsequences corresponding in amino acid identity and number to subsequences of human t-PA and of human u-PA, or mutants thereof, comprising culturing under appropriate nutrient conditions a transformed eukaryotic host containing a DNA sequence coding for said hybrid PA or mutant hybrid PA and isolating said hybrid PA or mutant thereof.

The transformed host cells are cultured by methods known in the art in a liquid medium containing assimilable sources of carbon, nitrogen and inorganic salts.

Various sources of carbon can be used for culture of the transformed yeast cells according to the invention. Examples of preferred sources of carbon are assimilable carbohydrates, such as glucose, maltose, mannitol or lactose, or an acetate, which can be used either by itself or in suitable mixtures. Examples of suitable sources of nitrogen are amino acids, such as casaminoacids, peptides and proteins and their degradation products, such as tryprone, peptone or meat extracts, yeast extracts, malt extract and also ammonium salts, for example ammonium chloride, sulfate or nitrate, which can be used either by themselves or in suitable mixtures. Inorganic salts which can also be used are, for example, sulfates, chlorides, phosphates and carbonates of sodium, potassium, magnesium and calcium.

The medium furthermore contains, for example, growth-promoting substances, such as trace elements, for example iron, zinc, manganese and the like, and preferably substances which exert a selection pressure and prevent the growth of cells which have lost the expression plasmid.

Thus, for example, if a yeast strain which is auxotrophic in, for example, an essential amino acid, is used as the host microorganism, the plasmid preferably contains a gene coding for an enzyme which complements the host defect. Cultivation of the yeast strain is performed in a minimal medium deficient in said amino acid.

Culturing is effected by processes which are known in the art. The culture conditions, such as temperature, pH value of the medium and fermentation time, are chosen such that a maximum title of the PA proteins of the invention is obtained. Thus, the yeast strain is preferably cultured under aerobic conditions by submerged culture with shaking or stirring at a temperature of about 20° to 40° C., preferably about 30° C., and a pH value of 5 to 8, preferably at about pH 7, for about 4 to 30 hours. Preferably until maximum yields of the proteins of the invention are reached.

Mammalian cells are Brown under tissue culture conditions using commercially available media optionally supplemented with growth promoting substances and/or mammal sera. The cells are grown either attached to a solid support, e.g. a microcarrier or porous glass fibers, or free-floating in appropriate culture vessels. The culture medium is selected in such a way that selection pressure is exerted and only those cells survive which still contain the hybrid vector DNA including the genetic marker. Thus, for example, an antibiotic is added to the medium when the hybrid vector includes the corresponding antibiotic resistance gene.

When the cell density has reached a sufficient value culturing is interrupted and the protein isolated. When using mammalian cells the hybrid PA or mutant hybrid PA protein is usually secreted into the medium. The medium containing the product is separated from the cells which can be provided with fresh medium and used for continuous production. When yeast cells are used the protein can also accumulate within the cells, especially in the periplasmatic space. In the latter case the first step for the recovery of the PA protein consists in liberating the protein from the cell interior. In most procedures the cell wall is first removed by enzymatic digestion of the cell wall with glucosidases (supra). Alternatively, the cell wall is removed by treatment with chemical agents, i.e. thiol reagents or EDTA, which give rise to cell wall damages permitting the produced hybrid PA or mutant thereof to be released. The resulting mixture is enriched for hybrid PA or for the mutant thereof by conventional means, such as removal of most of the non-proteinaceous material by treatment with polyethyleneimine, precipitation of the proteins using ammonium sulphate, gel electrophoresis, dialysis, chromatography, for example, ion exchange chromatography, size-exclusion chromatography, HPLC or reverse phase HPLC, molcular sizing on a suitable Sephadex® column, or the like. The final purification of the pre-purified product is achieved, for example, by means of affinity chromatography, for example antibody affinity chromatography, especially monoclonal antibody affinity chromatography using monoclonal anti-t-PA or anti-u-PA antibodies fixed on an insoluble matrix by methods known in the art, or, in the case of hybrid PAs containing the catalytic B-chain of t-PA, DE-3 affinity chromatography (DE-3 is a protease Inhibitor isolated from Erytrina latissima), and the like.

Hybridoma cell lines producing monoclonal antibodies directed to specific domains of t-PA or u-PA and said monoclonal antibodies are also objects of the invention.

For the convenient preparation of the one-chain form of the hybrid PA or mutant hybrid PA which is substantially free of the two-chain form, a procease inhibitor, such as aprotinin (Trasylol®) or basic pancreatic trypsin inhibitor, is advantageously included during the purification procedure in order to inhibit traces of proteases which may be present in :he culture medium and which may cause (partial) conversion of the one-chain form into the two-chain form. The final purification is then achieved by chromatography on a column containing a selective affinity reagent.

5. Pharmaceutical compositions

The novel single-chain hybrid PA proteins and mutants thereof obtainable according to the present invention, exhibit valuable pharmacological properties. They can be used in analogy to known plasminogen activators in humans for the prevention or treatment of thrombosis or other conditions where it is desired to produce local fibrinolytic or proteolytic activity via the mechanism of plasminogen activation, such as arteriosclerosis, myocardial and cerebral infarction, venous thrombosis, thromboembolism, post-surgical thrombosis, thrombophlebitis and diabetic vasculopathies.

It has surprisingly been found that the novel hybrid PA proteins and mutants thereof according to the present invention combine the beneficial properties of natural t-PA and u-PA. Thus, the novel hybrid PA proteins and mutants thereof are fibrinolytically active. The unique fibin directed properties, i.e. the ability to activate plasminogen preferentially in the presence of fibrin, are retained. Furthermore, the novel proteins have a prolonged in vivo stability as compared to authentic t-PA.

The invention relates also to pharmaceutical compositions that comprise a therapeutically effective amount of the active ingredient (hybrid PA or mutant thereof) together with organic or inorganic, solid or liquid pharmaceutically acceptable carriers that are suitable for parenteral, i.e. intramuscular, subcutaneous or intraperitoneal, administration and that do not deleteriously interact with the active ingredients.

There are suitable infusion solutions, preferably aqueous solutions or suspensions, it being possible to prepare these before use, for example from lyophilised preparations that contain the active ingredient alone or together with a carrier, such as mannitol, lactose, glucose, albumin and the like. The pharmaceutical compositions are sterilized and, if desired, mixed with adjuncts, for example preservatives, stabilisers, emulsifiers, solubilisers, buffers and/or salts for regulating the osmotic pressure. Sterilization can be achieved by sterile filtration through filters of small pore size (0.45 μm diameter or smaller) after which the composition can be lyophilised, if desired. Antibiotics may also be added in order to assist in preserving sterility.

The pharmaceutical compositions according to the present invention are dispensed in unit dosage forms, for example ampoules, comprising 1 to 2000 mg of a pharmaceutically acceptable carrier per unit dosage and about 1 to 200 mg, preferably about 5 to 100 mg, of the active ingredient per unit dosage.

Depending upon the type of the disease and the age and the condition of the patient, the daily dose to be administered for the treatment of a patient weighing approximately 70 kg is in the range from 3 to 100 mg, preferably from 5 to 50 mg, per 24 hours. In the case of myocardial infarction preferably a dose of about 30 to 80 mg is administered within 60 to 120 minutes, preferably in three aliquots and within about 90 minutes. The total amount of hybrid PA or mutant hybrid PA can also be administered as bolus injection.

The invention also provides a method for producing a pharmaceutical composition characterised in that a biologically active protein according to the present invention is admixed with a pharmaceutically acceptable carrier.

The use of the new proteins for the prophylactic and therapeutic treatment of the human body is also an object of the present invention.

The invention concerns especially the DNAs, the hybrid vectors, the transformed host strains, the hybrid PA proteins, the mutant hybrid PA proteins, the hybridoma cell lines, the monoclonal antibodies, and the processes for the preparation thereof as described in the Examples.

BRIEF DESCRIPTION OF THE DRAWINGS

In the following experimental part various embodiments of the present invention are described with reference to the accompanying drawings in which:

FIGS. 1A–1F and FIGS. 3A–3E illustrate the nucleotide sequences and deduced amino acid sequences of human t-PA eDNA and human u-PA cDNA, respectively. The first amino acids of the mature proteins are underlined.

FIG. 17 schematically depicts the construction of u-PA expression plasmid pBR3a.

FIG. 23 shows the construction of a gene coding for a hybrid PA comprising the A-chain domains of t-PA and the B-chain of u-PA.

FIG. 24 shows the construction of a gene coding for a hybrid PA comprising the A-chain domains of u-PA and the B-chain of t-PA.

FIG. 25 shows the construction of a gene coding for a hybrid PA comprising the u-PA growth factor domain, the kringle 2 domain of t-PA and the B-chain of t-PA.

FIG. 26 shows the construction of a gene coding for a hybrid PA comprising the u-PA growth factor domain, the kringle 2 domain of t-PA and the B-chain of u-PA.

Symbols used in the accompanying figures have the following meanings:

| | |
|---|---|
| AMP, Amp$^R$ | ampicillin resistance gene (beta-lactamase) |
| TET, Tet$^R$ | tetracyclin resistance gene |
| NEO | Tn5 neomycin phosphotransferase |
| TN5PR | bacterial promoter of transposon TN5 |
| HPH | hygromycin phosphotransferase |
| pBRori | origin of replication of plasmid pBR322 |
| POIS | 'poison-sequence', pBR322 sequence which is inhibitory to SV40 replication |
| SV40ori | origin of replication of SV40, coincides with early and late promoters. |
| SV40enh,SV40E | 72 bp enhancer, part of SV40 early promoter |
| HCMVE | enhancer of human cytomegalovirus (HCMV) major immediate early gene |
| MCMVP | promoter/mRNA start site of mouse cytomegalovirus (MCMV) major immediate early gene |
| RSV | Rous sarcoma virus LTR (promoter) |
| CAP | position of 5' m7Gp 'cap' of eukaryotic mRNA |
| polyA | polyadenylation site of mRNA |
| SPLD | splice donor site, 5' end of intron |
| SPLA | splice acceptor site, 3' end of intron |
| BAP | bacterial alkaline phosphatase |
| CIP | calf intestinal phosphatase |
| (BamH1/Bgl2) | Sau3a site resulting from coligating a BamHI and a BglII site |
| ScaI(del) | mutated ScaI site |
| x < y | restriction enzyme site x located clockwise from y |
| p | promoter |
| inv.SS | invertase signal sequence |
| t | transcription terminator |
| L | linker DNA |
| DHFR | dihydrofolate reductase |
| mtPA | Bowes melanoma t-PA |

EXPERIMENTAL PART

Example 1: Introduction of a ScaI site at the junction between the kringle structures and the enzyme domain in human t-PA cDNA One approach used to construct chimeric or hybrid molecules containing domains of both t-PA and u-PA consists in preparing desired restriction fragments derived from the respective clones, reassembling them in solution, then cloning the resulting constructs. After cloning the structure of the chimetic molecules is verified by restriction mapping and DNA sequence analysis.

Figures 2A, 2B:
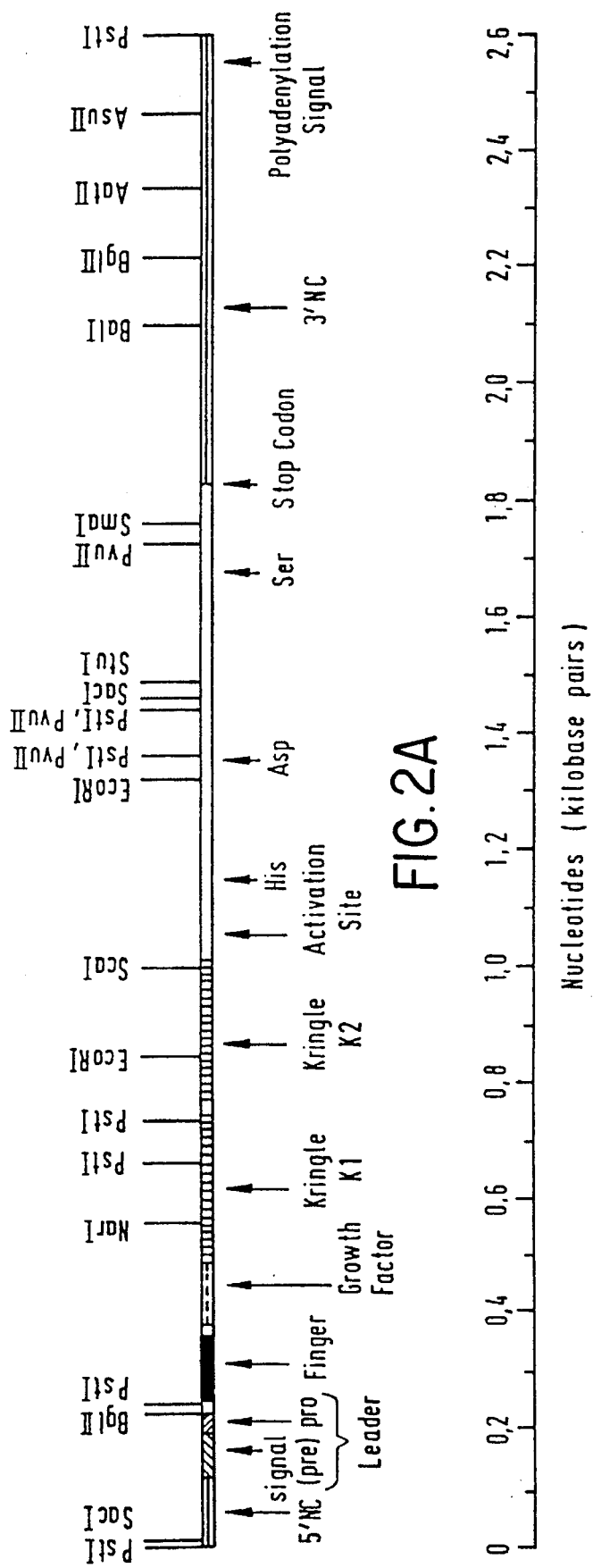
FIGS. 2A–2B and FIGS. 4A–4B are restriction endonuclease maps of human t-PA cDNA and human u-PA cDNA, respectively.
Figure 5:
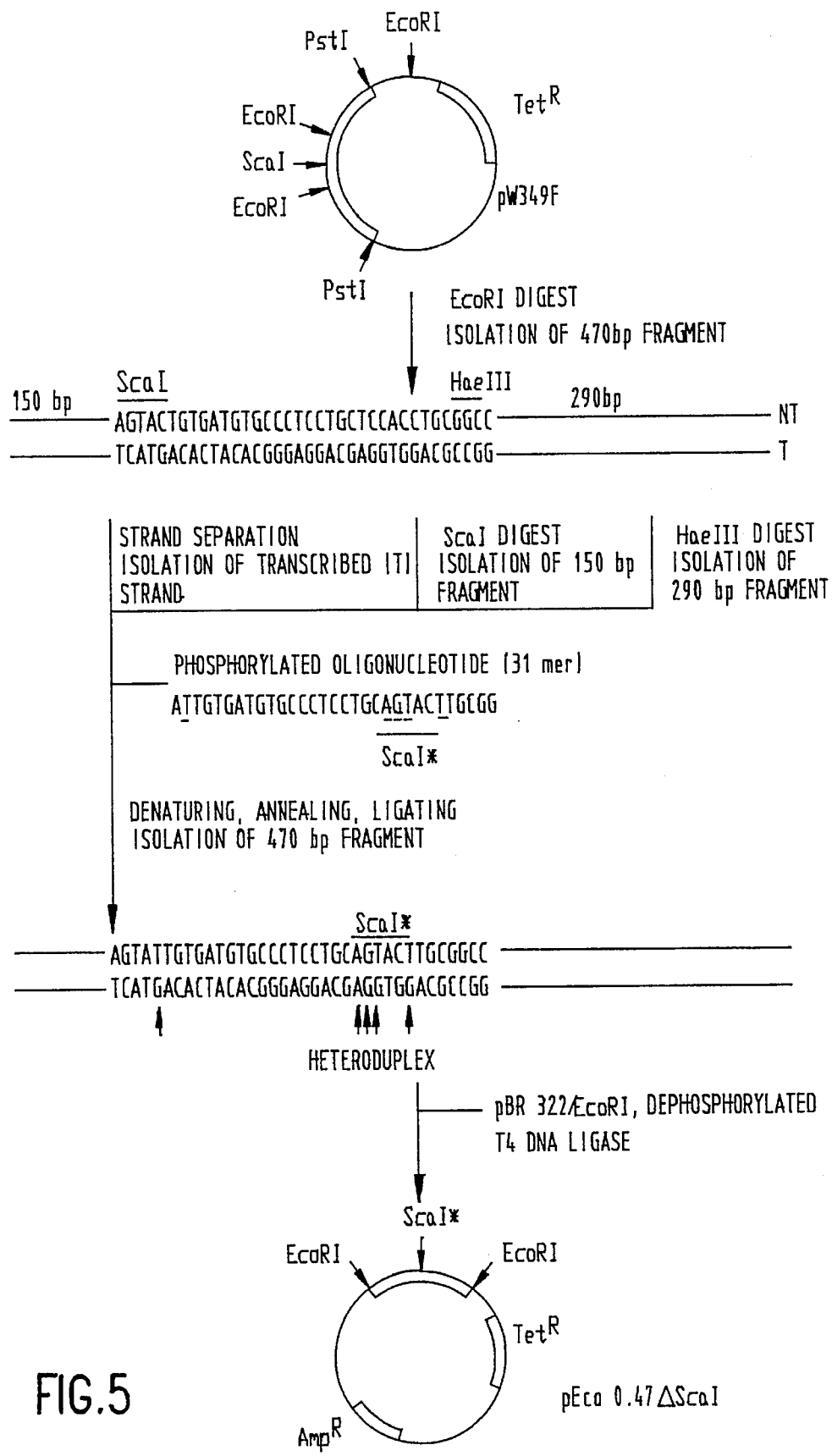
FIG. 5 schematically illustrates the technique used to construct plasmid pEcoO·47ΔScaI.

To obtain the hybrid molecules both t-PA and u-PA cDNAs are cleaved at the junctions between the respective kringle structures and enzyme domains. This is accomplished with u-PA by performing a partial digest with the restriction endonuclease MstI, which separates the non-catalytic domain from the enzyme domain and associated sequences at its 3'end. No comparably useful potential cleavage site is present in t-PA, and one is accordingly Introduced as described below:

Construction of plasmid pEco0.47ΔScaI (see FIG. 5) In this construct, the unique ScaI site (AGTACI) at nucleotide position 940-945 of the t-PA cDNA is destroyed (AGTACT→AGTATT) and another ScaI site introduced at nucleotide positions 963-968 (TCCACC→AGTACT) at the 3'end of kringle 2 (cf. FIGS. 1 and 2). The coding of none of the amino acids is affected by these changes.

All restriction digests are carried out according to the manufacturer's (New England Biolabs, Bethesda Research Labs) instructions and the resulting digests are analyzed by electrophoresis on 3.5% polyacryl amide gel. The gel is stained with ethidium bromide (1.0 μg/ml) and visualized with ultraviolet light. The appropriate band is excised and electroeluted in 0.5×TBE (1×TBE=90 mM Tris-borate, pH 8.3, 2.5 mM EDTA). The electroeluted material is applied to Elutiped column (Schleicher and Schuell), the bound DNA eluted in high salt and precipitated by the addition of ethanol. The pellet is washed with ethanol, dried and dissolved in water.

Plasmid pW349F (European Patent Application No. 143, 081) containing human t-PA cDNA (synthesized from mRNA isolated from HeLaS3 cells and cloned into the PstI site of plasmid pBR322) is digested with EcoRI and the 470 base pair (bp) fragment (cf. FIG. 2) is isolated. The 150 bp EcoRI, ScaI and the 290 bp EcoRI, HaeIII fragments are obtained by digesting the 470 bp EcoRI fragment with ScaI and HaeIII, respectively. The two strands of the 470 bp EcoRI fragment are separated by denaturing the DNA in DMSO buffer (30% DMSO, 1 mM EDTA, 0.5% xylene cyanole, 0.05% bromphenol blue) and electrophoresing on a 5% polyacrylamide gel in 0.5×TBE at 8 volts per centimeter [Maniatis et al., Molecular Cloning, A Laboratory Manual, Cold Spring Harbor Laboratory; 1982]. The separated strands are recovered by electroelution followed by ethanol precipitation. A 3i-mer deoxyoligonucleotide (incorporating the 5 desired nucleotide changes, cf. FIG. 5) is synthesized using the phosphotriester method. Fifty moles of the 31-met are $^{32}$P-labelled at the 5'end in a 20 μl reaction containing 1×kinase buffer (10×kinase buffer=0.5 M Tris·HCl, pH 7.5, 0.1 M MgCl$_2$, 50 mM DTT, 1 mM spermidine, 1 mM EDTA), 30 μCi [α$^{32}$P]ATP (Amersham, p18 3000 Ci/mmol) and 10 units T$_4$ polynucleotide kinase (Bethesda Research Labs.). The reaction is incubated at 37° C. for 30 minutes followed by the addition of 1 μl of 10 mM ATP, 10 units T$_4$ kinase and a further 30 minute incubation at 37° C. The reaction is terminated by heating at 68° C. for 10 min. The labelled 31-met, whose sequence is that of the non transcribed strand, is used as the probe in a dot blot analysis [performed according to Zoller and Smith, Nucl. Acids Res., 10, 6487–6500 (1982); except that prehybridization and hybridization are done at 50° C. and washing at 60° C.] to determine which of the two strands hybridizes to it, i.e. represents the transcribed strand. The four DNAs are mixed together in a 20 μl annealing reaction which consists of 0.3 μmoles of the transcribed strand, 2 μmoles each of the 150 bp EcoRI, ScaI and 290 bp EcoRI, HaeIII fragments, 25 μmoles of the phosphorylated 31-mer and 1×annealing buffer (5×annealing buffer=0.5 M NaCl, 32.5 AM Tris·HCl pH 7.5, 40 mM MgCl$_2$ and 5 mM B-mercaptoethanol). The mixture is incubated at 100° C. for 3 min, 30° C. for 30 min, 4° C. for 30 min and then on ice for 10 min following which 400 units of T$_4$ DNA ligase (New England Biolabs) are added and the reaction incubated at 12.5° C. overnight. The 470 bp annealed fragment is recovered from a 3.5% polyacrylamide gel as described above and ligated to EcoRI digested and dephosphorylated pBR322 DNA (New England Biolabs) in 50 AM Tris·HCl pH 7.5, 10 mM MgCl$_2$, 10 mM DTT, 1 mM ATP, 1 mM spermidine, 0.1 mg/ml bovine serum albumin by overnight incubation at 12° C. The ligation mix is used to transform competent E. coli strain HB101 (Maniacis et al., supra). Ampicillin-resistant colonies are selected on L-agar containing 50 μg/ml ampicillin and colonies containing the 470 bp fragment are identified by colony hybridization using the 31-Aer as the probe [D. Woods, Focus 6, 1–3 (1984)]. Plasmid DNA is isolated from several positively hybridizing colonies on a small scale [Holmes et al., Analyt. BiocheA. 114, 193–197 (1981)]and the generation of the new 5caI site is verified by combined EcoRI, ScaI digestion. To ensure purity, plasmid DNA from the positive colonies is used for a second round of transformation of *E. coli* HB101. Large scale plasmid preparation is made from one such second generation positive colony [Katz et al., J. Bacteriol. 114, 577–591 (1973); Bio-chemistry 16, 1677–1683 (1977)] and the destruction of the original ScaI site and the generation of the new ScaI site are verified by DNA sequence analysis using the method of Maxam and Gilbert [Methods Enzym. 65, 499–560 (1980) 3. This plasmid is designated pEco0.47ΔScaI.

Figure 6:
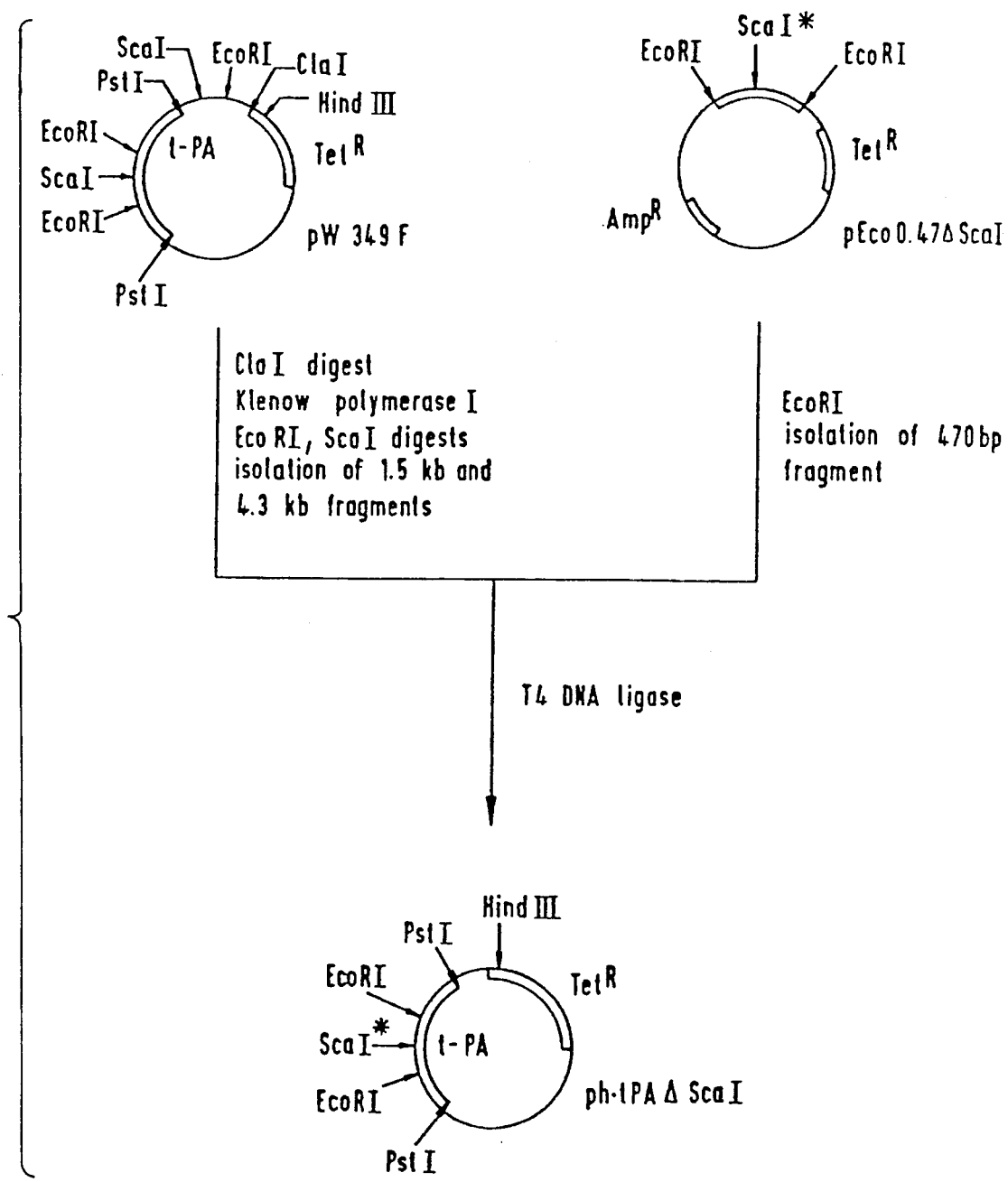
FIG. 6 schematically illustrates the construction of plasmid ph-tPAΔScaI containing a mutated t-PA cDNA.

B) Reconstruction of human t-PA with mutant ScaI site (see FIG. 6)

In this construct the 470 bp EcoRI fragment present on the wild type human t-PA is exchanged for the 470 bp EcoRI fragment containing the mutant ScaI site. Plasmid pW349F containing human t-PA cDNA (see above) is digested with ClaI and the resulting sticky ends are made blunt by the addition of 50 μm each of dCTP, dGTP and 10 units of DNA polymerase I, Klenow fragment (Boehringer, Mannhelm). The reaction is incubated at room temperature for 30 min followed by phenol and ether extraction and ethanol precipitation. The pellet is dissolved in water, digested with EcoRI and ScaI, and 1.5 kb EcoRI, ScaI and 4.3 kb ClaI (blunt ended), EcoRI fragments are isolated. These two fragments are mixed with the 470 bp fragment recovered from plasmid pEco0.47ΔScaI after EcoRI digestion and ligated as described above at 12° C. overnight. Competent *E. coli* HB101 cells are transformed with the ligation mix and tetracycline resistant colonies selected on L-agar containing 12.5 μg/ml tetracycline. Colonies containing the 470 bp mutant fragment are identified by colony hybridization using the previously described 31-mer as the probe. DNA from minilysates of several of the positively hybridizing colonies is prepared and the exact nature of the construct is verified by performing appropriate restriction digests. One such plasmid with the desired changes is termed ph-tPAΔScaI.

Figure 7:
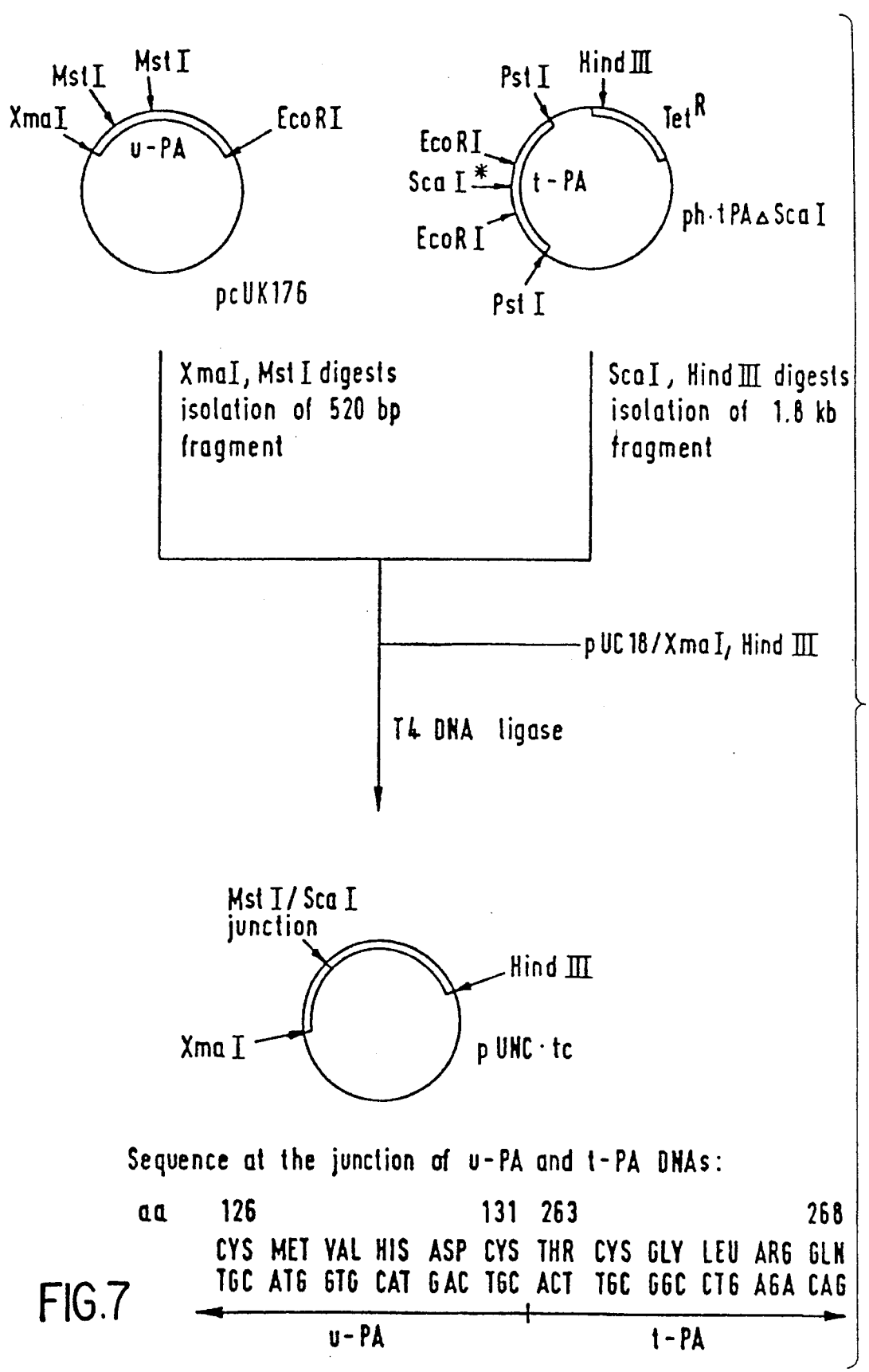
FIG. 7 schematically illustrates the construction of plasmid pUXC·tc containing a cDNA Insert comprising the A-chain domains of u-PA and the B-chain of t-PA.

Example 2: Construction of a u-PA/t-PA hybrid molecule: plasmid pUNC-tc (see FIG. 7)

Figures 4A, 4B:
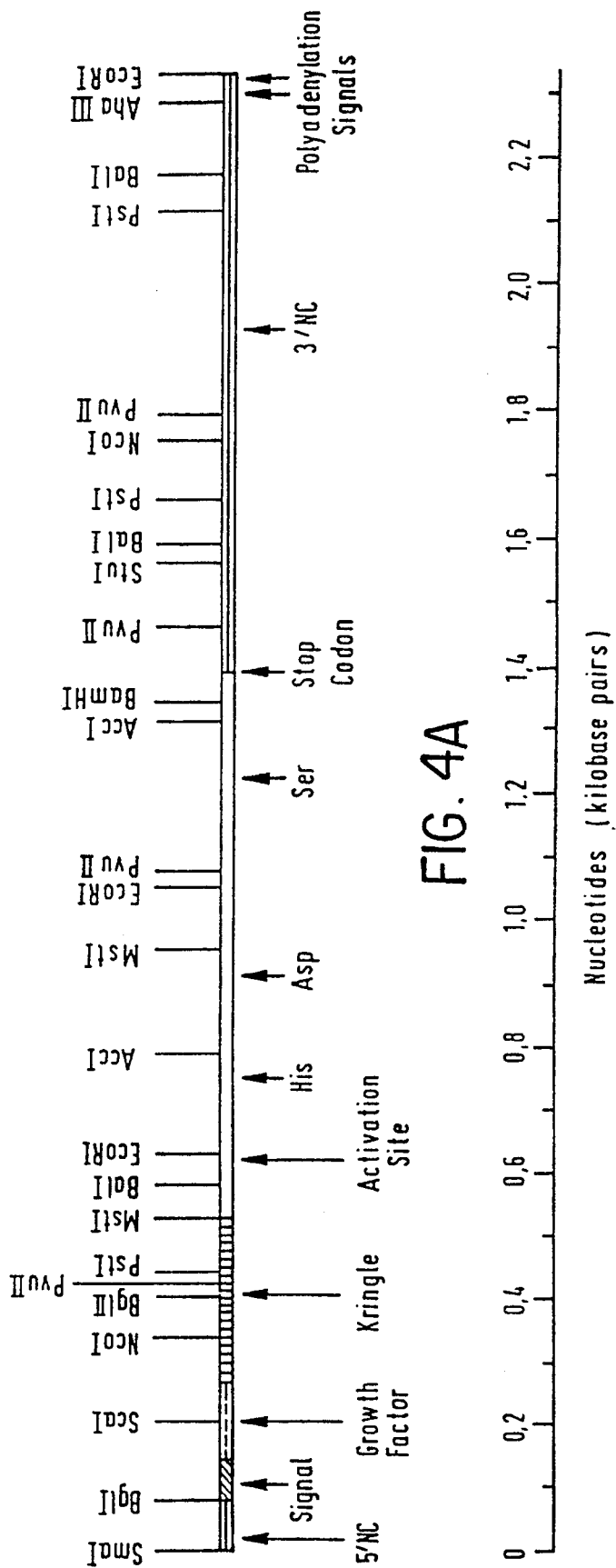

This construct is a hybrid between the noncatalytic region of u-PA containing the 5' noncoding region, signal, growth factor and the kringle sequences) and the catalytic or enzyme domain of human t-PA. Urokinase cDNA is prepared from mRNA obtained from human Hep3 cells [cf. T. Maniatis et al., Molecular Cloning (1982), p. 188–246]. A 1.3 kb SmaI-BamHI fragment and a 1 kb BamHI-EcoRI fragment of the u-PA cDNA is cloned into the SmaI, EcoRI sites of pUN211 B. Nilsson et al., Nucl. Acids Res. 11, 8019–8030 (1983)] to yield plasmid pcUK176. The restriction endonuclease map of the human u-PA cDNA insert is shown in FIG. 4. The nucleotide sequence and deduced amino acid sequence of the u-PA insert is given in FIG. 3.

Plasmid pcUK176 is digested with XmaI (cf. FIG. 4: XmaI is an isoschizomer of SmaI) and MstI and the 521 bp fragment is isolated. Restriction enzyme MstI recognizes the DNA sequence TGC⁑GCA (arrows indicate site of cleavage) and produces blunt ends upon digestion; this enzyme therefore cuts u-PA cDNA at nucleotides 520–525, i.e., right after the last cysteine residue (amino acid 131) comprising the kringle [Holmes et al., Biotechnology 3, 923–929 (1985)], and thus cleanly separates the coding sequences for noncatalytic and catalytic regions. Plasmid ph-tPAΔScaI is digested with ScaI and HindIII (Hind III is present in the vector) and the 1.8 kb fragment recovered. Restriction enzyme ScaI recognizes the DNA sequence AGT⁑ACT (arrows indicate site of cleavage) and also yields blunt ends upon digestion. ScaI will cut ph-tPAaScaI DNA after the serene residue 262 [1 amino acid past the last cysteine of kringle 2; Pennica et al., Nature 301, 214–221 (1983)], hence separating the noncatalytic and the catalytic domains.

The two fragments are mixed and ligated to XmaI, HindIII cleaved pUC18 vector DNA. After transformation of *E. coli* HB101, colinies having the correct insert are identified by colony hybridization using the 2.0 kb BglII fragment of human tPA (cf. FIG. 2) as the probe [the probe is labelled by the random priming method: Feinberg et al., Analyt. Biochem. 132, 6–13 (1983)]. The DNA sequence at the junction of ligation of the u-PA and t-PA fragments is verified by DNA sequence analysis. One correct clone is designated pUNC-tc.

Figure 8:
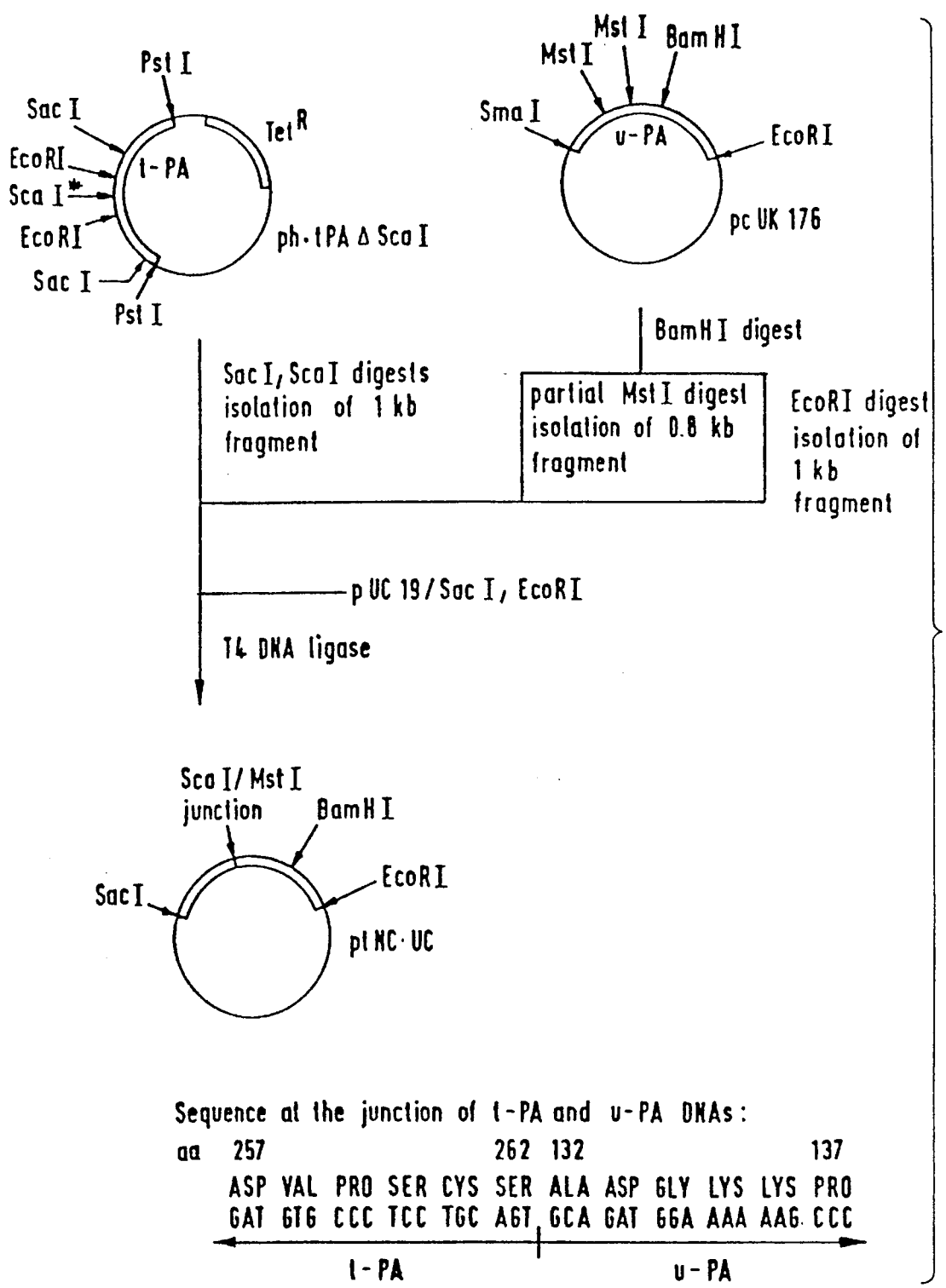
FIG. 8 schematically depicts the construction of plasmid ptNC-UC containing a cDNA insert comprising the A-chain domains of t-PA and the B-chain of u-PA.

Example 3: Construction of a t-PA/u-PA hybrid molecule: plasmid ptNC·UC (cf, FIG. 8)

This construct is just the reverse of pUNC-tc in that the noncatalytic region of ph-tPAΔScaI (containing 5' noncoding region, leader, finger, growth factor, kringle 1 and kringle 2 domains) is fused to the catalytic domain of human u-PA. Plasmid ph-tPAΔScaI is digested with SacI and ScaI (cf. FIG. 8) and an about 1.0 kb fragment is isolated. Plasmid pcUK176 is first digested with BamHI and then partially cleaved with MstI and the about 800 bp fragment recovered. Next, the BamHI digest is cut with EcoRI and the about 1.0 kb fragment is isolated. These three fragments are mixed with pUC19 vector digested with SacI, EcoRI and ligated. *E. coli* HB101 is transformed with the ligation mix and colonies having the correct insert are identified by colony hybridization using the same 2.0 kb BglII probe as described above. DNA sequence at the junction of t-PA and u-PA DNA is verified by DNA sequence analysis. One correct clone is termed ptNC/NC·UC.

Example 4: Construction of an expression vector for use in mammalian cells

A) Conversion of the HgiAI site in t-PA cDNA to a HindIII site

Figure 9:
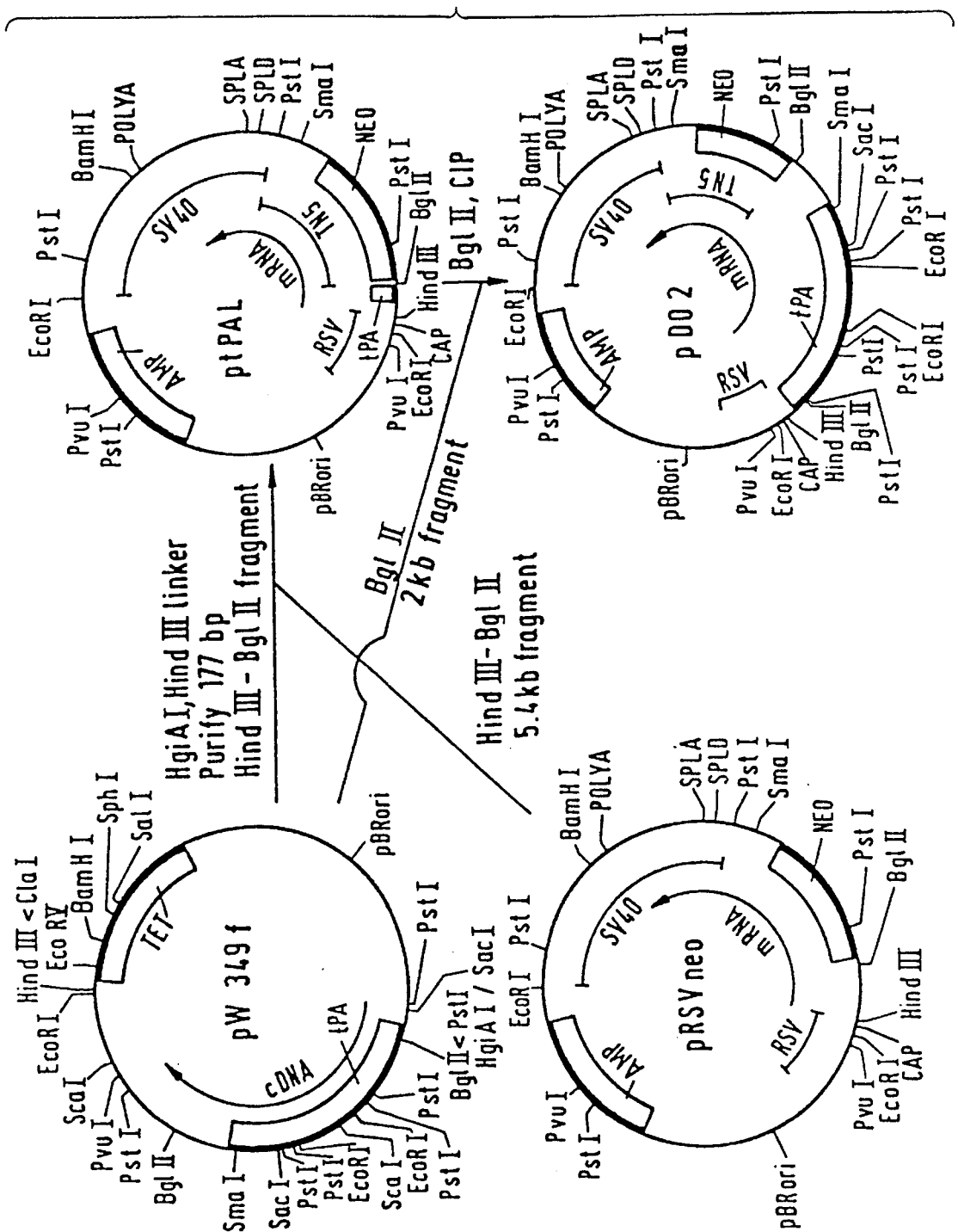
FIG. 9 schematically depicts the construction of plasmid pDO2.

This is achieved in five steps (FIG. 9).

Plasmid pW349F (European Patent Application No. 143, 081) is partially cleaved with the restriction enzyme HgiAI by incubation of 20 μg/ml DNA for 1 h at 37° C. with 12 U/ml of the enzyme in the buffer recommended by the manufacturer (Bethesda Research Laboratories) except that it is supplemented with 10 μg/ml ethidium bromide to suppress secondary cutting of the plasmid. Linearized plasmid DNA is then applied to a 0.8% agarose gel in TBE buffer (TBE: 89 mM Tris-borate pH 8.9 containing 1 mM EDTA), electrophoretically eluted in the same buffer, twice extracted with phenol, twice with chloroform and finally precipitated with alcohol at −20° C. after addition of 0.1 vol. of 3 M sodium acetate ph 5.2. Pelleted DNA is dissolved at 0.2 mg/ml in TE (TE: 10 mM Tris-HCl pH 7.2 with 0.1 mM EDTA).

63 μl of linearized DNA is then incubated for 30 min. at 37° C. with 15 U of T4 DNA polymerase in ligase buffer [33 mM Tris-acetate (pH 7.9), 66 mM potassium acetate, 10 mM magnesium acetate, 0.5 mM dithiothreitol and 0.1 mg/ml bovine serum albumin] followed by heating 10 min. at 60° C. to inactivate the enzyme. The purpose of this incubation is to use the exonucleolytic activity of the T4 polymerase to remove the protruding four nucleotides left after digestion with HgiAI to obtain blunt-ended DNA molecules.

In order to ligate HindIII linkers (CAAGCTTG) to the blunt-ended DNA 6 μl (300 rig) kinased linkers are added to the above solution with 4 μl 10 mM ATP and 3 μl T4 DNA ligase (New England Biolabs, 400 u/μl) followed by a 16 h incubation at 16° C. The ligation is terminated by heating the mixture 10 min. at 68° C., after which the DNA is digested with HindIII and BglII, i.e. 15 μl (135 U) HindIII is added with 1.5 μl 4 M NaCl, 0.2 μl 1 M MgCl$_2$ and 11 μl 1 mg/ml bovine serum albumin, incubated at 37° C. for 1 h followed by addition of 40 U BglII followed by another 1 h incubation at 37° C. The resulting 177 base pair fragment is purified on a 6% polyacrylamide gel run in TBE, eluted in TNE (TNE: 10 mM Tris-HCl pH 8.8 containing 100 mM NaCl and 1 mM EDTA), absorbed to DEAE cellulose (Whatman DE52), eluted with 1 M NaCl in TNE, diluted with 4 volumes of water, precipitated at −20° C. after addition of 2.5 volumes of ethanol and finally dissolved in 17 μl TE (TE: 10 mM Tris-HCl pH 8.0 containing 1 mM EDTA).

Plasmid pRSVneo is a derivative of plasmid pSV2neo [P. J. Southern and P. Berg, J. Mol. Appl. Genet. 1, 327–341 (1982)] in which the SV40 -derived PvuII-HindIII fragment has been replaced with a PvuII-HindIII fragment containing the LTR promoter from Rous sarcoma virus in the same manner as pRSVcat was constructed from pSV2cat [C. M. Gorman et el., Proc. Natl. Aced. Sci. USA 79, 6777–6781 (1982)]. 5 μg of this plasmid is cut in a 50 μl volume with 24 U BglII according to the manufacturer's instructions. After a 1 h incubation at 37° C. 40 U HindIII are added and the incubation continued for 1.5 hour after which the large 5.4 kb fragment is purified as described above.

17 μl of the purified 177 bp fragment are ligated for 18 hours at 16° C. to 2 μl (20 ng) of the pRSVneo fragment using 0.25 μl (100 U) T4 ligase in a total volume 22 μl ligase buffer, after which the plasmid DNA is used to transform *E. coli* according to D. Hanahan [J. Mol. Biol. 166, 557–580 {1983}]. From the resultant ampicillin-resistant strains one is selected containing a plasmid designated ptPAL with the 177 bp HindIII-BglII fragment as evidenced by restriction analysis. 0.1 μg of this plasmid is cut in 60 μl with 16 U BglII as recommended by the manufacturer for 1.5 h at 37° C. To this solution is then added 20 U calf intestinal alkaline phosphatase (Boehringer Mannheim) and the incubation continued for 30 min. after which the DNA is extracted twice with phenol, twice with chloroform and precipitated after adding 0.1 volume 3.0 M sodium acetate pH 5.2 and 0.6 volume of isopropanol, dissolved in TE, further purified by agarose gel electrophoresis as described above, twice extracted with phenol, twice with chloroform, precipitated at −20° C. after addition of 2.5 volumes ethanol and 0.1 vol. 3 M sodium acetate pH 5.2 and finally dissolved in 30 μl TE. The 2.1 kb tPA BglII fragment is then cut out of 5 μg pW349F in a 25 μl reaction using 20 U BglII for 2 h at 37° C., purified on a 0.8% agarose gel, electrophoretically eluted as described above, twice extracted with phenol-, twice with chloroform, precipitated at −20° C. after addition of 2.5 volumes ethanol and 0.1 vol. 3 M sodium acetate pH 5.2 and dissolved at a concentration of 8 ng/pl in TE. 1 μl of the t-PA fragment is then ligated in a 10 μl reaction to 7.5 ng BglII cut vector DNA using 100 U T4 ligase (Biolabs) for 17 h at 16° C. and subsequently transformed into *E. coli*. One of the resultant clones, designated pD02, contains the t-PA BglII fragment inserted in such a way that the plasmid contains a continuous open reading frame for human t-PA.

B) Combination of the t-PA cDNA with the beta globin fragment

Figure 10:
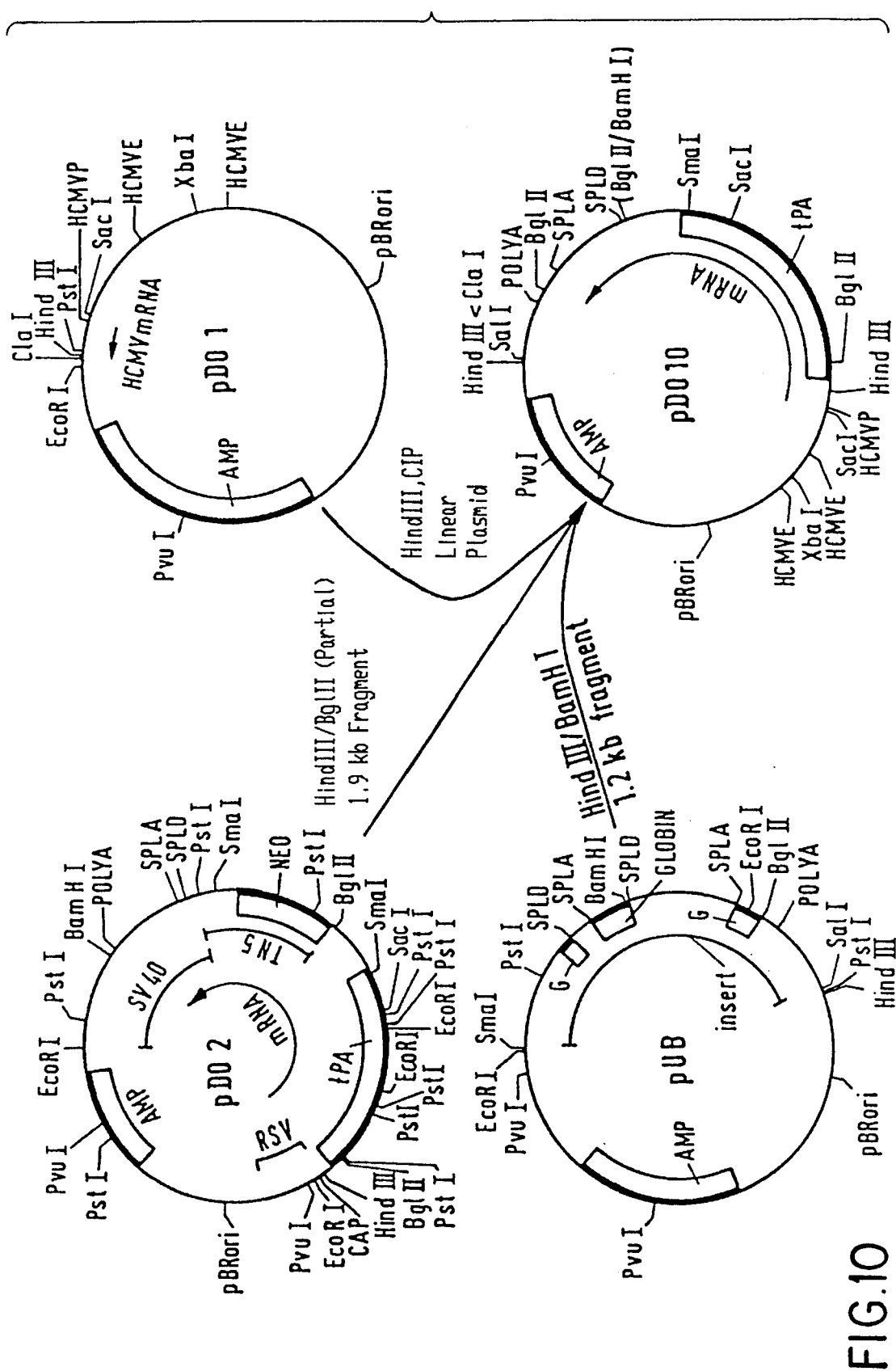
FIG. 10 schematically illustrates the construction of plasmid pDO10 containing the t-PA cDNA combined with a beta globin fragment.

Plasmid pDO10 (FIG. 10) is constructed by coligating three DNA fragments: (i) a 2.1 kb fragment starting with a HindIII site and terminating with a BglII site containing the whole t-PA coding sequence is isolated from an agarose gel on which is loaded 10 μg of pD02 DNA cut partially with BglII and completely with HindIII. (ii) pUB is a plasmid containing the rabbit beta globin gene [A. Van Ooven et al., Science 206, 337 (1979)]subcloned as a BglII partial digest into the BamHI site of plasmid pUC9 [J. Vieira and J. Messing, Gene 1–9, 259–268 (1982); ibid. 19, 269–276 (1982)]. From this plasmid a 1.2 kb BamHI-HindIII fragment containing the second intron and the polyadenylation site is excised and purified by agarose gel electrophoresis. (iii) Vector pDO1 is built up, in anticlockwise order from the HindIII site (FIG. 10) of the HindIII-AccI fragment of pBR322 which includes the origin of replication, a 0.3 kb fragment containing the enhancer of human cytomegalovirus (HCMV) terminating in a synthetic XbaI site followed by a second copy of this enhancer attached to the homologous promoter terminating at a synthetic HindIII site. This vector DNA is cut with HindIII and the 6.3 kb linear plasmid is purified by agarose gel electrophoresis.

Figure 11:
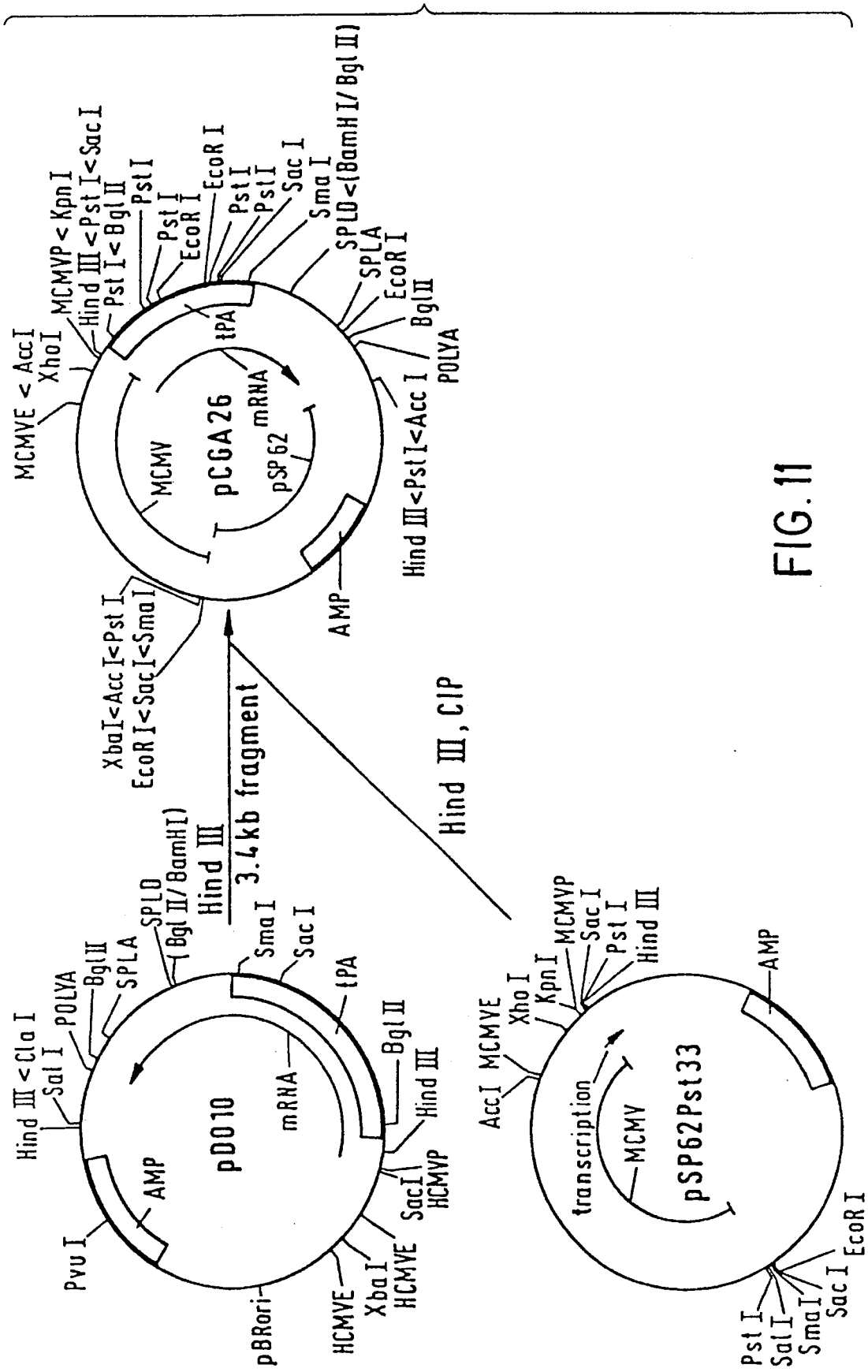
FIG. 11 schematically illustrates the construction of plasmid pCGA26 containing the t-PAc DNA under control of the MCMV IE promoter and a beta globin fragment.

C) Inserting the tPA/globin combination into pSP62Pst33 (see FIG. 11)

pSP62Pst33 (FIG. 11) is a plasmid containing a 2.1 kb PstI fragment of the mouse cytomegalovirus (MCMV) DNA, which includes the vital immediate early (IE) promoter, inserted into the PstI site of plasmid pSP62 (Boehringer Mannheim) as indicated in the figure. Into the HindIII site of pSP62Pst33 is inserted the HindIII fragment from pDO10. A plasmid, pCGA26, is selected in which the t-PA coding sequence is inserted such that it can be transcribed in "sense" orientation from the MCMV IE promoter.

Figure 12:
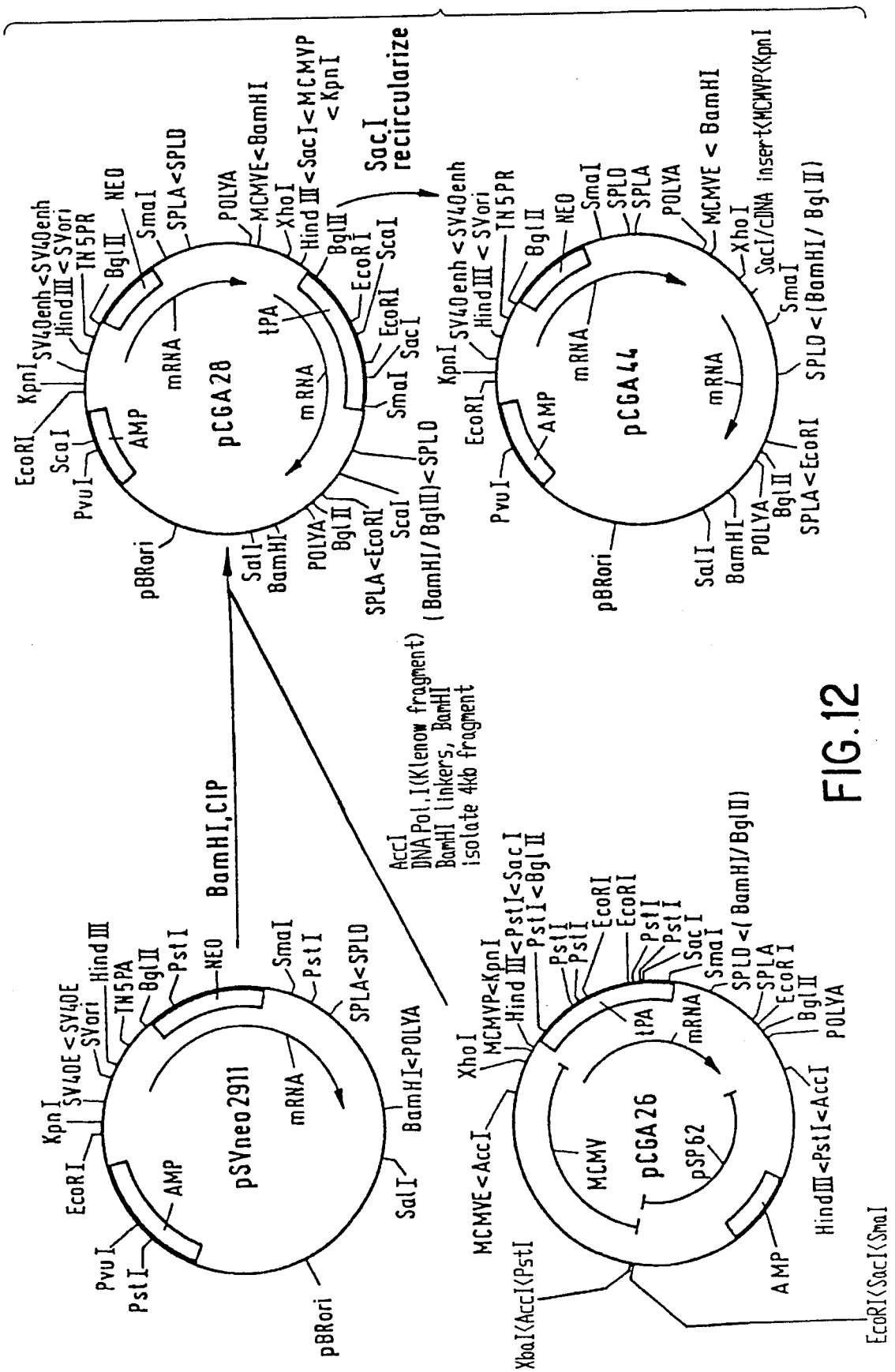
FIG. 12 schematically illustrates the construction of t-PA expression plasmid pCGA28 and of universal expression plasmid pCGA44, both plasmids including the neomycin resistance gene.

D) Inserting the MCMV/tPA/globin unit into pFASV2911neo (see FIG. 12)

Plasmid pSV2911neo [F. Asselbergs et al., J. Mol. Biol. 189, 401–411 (1986)] contains the neomycin (neo) phosphotransferase gene from transposon IN5 in an SV40 expression cassette (FIG. 12). Thus it confers resistance to neomycin and kanamvcin when introduced into mammalian tissue culture cells. pSV2911neo DNA is prepared for cloning by cutting with BamHI, treating with calf intestinal alkaline phosphatase, two extractions with phenol, two with chloroform, precipitation with alcohol and finally dissolved in TE. Plasmid pCGA26 is cut with restriction enzyme AccI, which cuts the sequence GT/ACAC at position 345 in the MCMV enhancer/promoter region [K. Doersch-Haessler et al., Proc. Natl. Acad. Sci. USA 82, 8325–8329 (1985)} and the sequence GT/CGAC (can also be cut with SalI) behind the globin part. The two base overhangs resulting after cutting are filled in with *E. coli* (large fragment) DNA polymerase I, the now blunt ends are ligated to BamHI linkers (CGGATCCG) and these cut with BamHI enzyme. The 3.8 kb fragment carrying the MCMV/tPA/globin unit now with BamHI ends is purified via an agarose gel and then ligated to the pSv2911neo DNA prepared as described above to yield expression plasmid pCGA28.

E) Expression vectors derived from pCGA28 pCGA42 is a derivative of pCGA28 in which the neo coding sequence (between the BglII site and SmaI site) is replaced by the coding sequence of a hygromycin resistance gene. This is achieved (see FIG. 13) by cutting plasmid pSV2911neo at its unique SmaI site, ligating a BglII linker (CAGATCTG) to the DNA followed by cutting with BglII. The resulting large DNA fragment consisting of the vector minus the neo coding sequence is purified on an agarose gel and ligated to the small BamHI fragment from plasmid pLG89 [L. Gritz et el., Gene 2–5, 179–188 (1983)] equally purified on an agarose gel, leading to plasmids pCGA25c and pCGA25d, which contain the hygromycin phosphotransferase gene in the sense and antisense orientation, respectively. When transfected into CHO DUKXB1 cells on standard conditions (see Example 16), pCGA25C gives 60 colonies/μg DNA resistant to 0.2 μg/ml hygromycin B, a concentration which kills CHO cells containing a plasmid not encoding hygromycin resistance, for example pCGA28. In pCGA25c the sequences encoding hygromycin-B resistance are located such that in *E. coli* they are transcribed from the Tn5 promoter (which in transposon Tn5 transcribes the kanamycin resistance gene). Thus, a 2.5 ml culture of Luria broth [LB] containing 40 mg/l hygromycin-B inoculated with 0.05 ml of an overnight, i.e. saturated culture of *E. coli* DH1 bacteria (grown under 50 mg/l ampicillin selection) reaches after 3 h aerated culture at 37° C. an at least 10 times higher bacterial density, then when bacteria with plasmids not containing a hygromycin gene functional in *E. coli* , such as pCGA25d, pCGA28 or pAT153 ! A.J. Twigg et al., Nature 283, 216–218 (1980)], are tested. The functionality of the hygromycin-B resistance gene both in animal tissue culture cells and in *E. coli* greatly facilitates the use of plasmid pCGA25c and its derivatives. Plasmid pCGA42 is then constructed by inserting the BamHI fragment from pCGA28 containing the MCMV/t-PA/beta-globin cassette into pCGA25C. Its use is to transfer t-PA expressing gene into cells which cannot be transformed to geneticin resistance or which are already geneticin resistant. Also pCGA42 is capable of expressing its hygromycin gene in *E. coli* , allowing pCGA42 containing *E. coli* DH1 to grow to densities a least 10 times higher than, for example, pCGA28 containing *E. coli*, when tested as described above.

Figure 13:
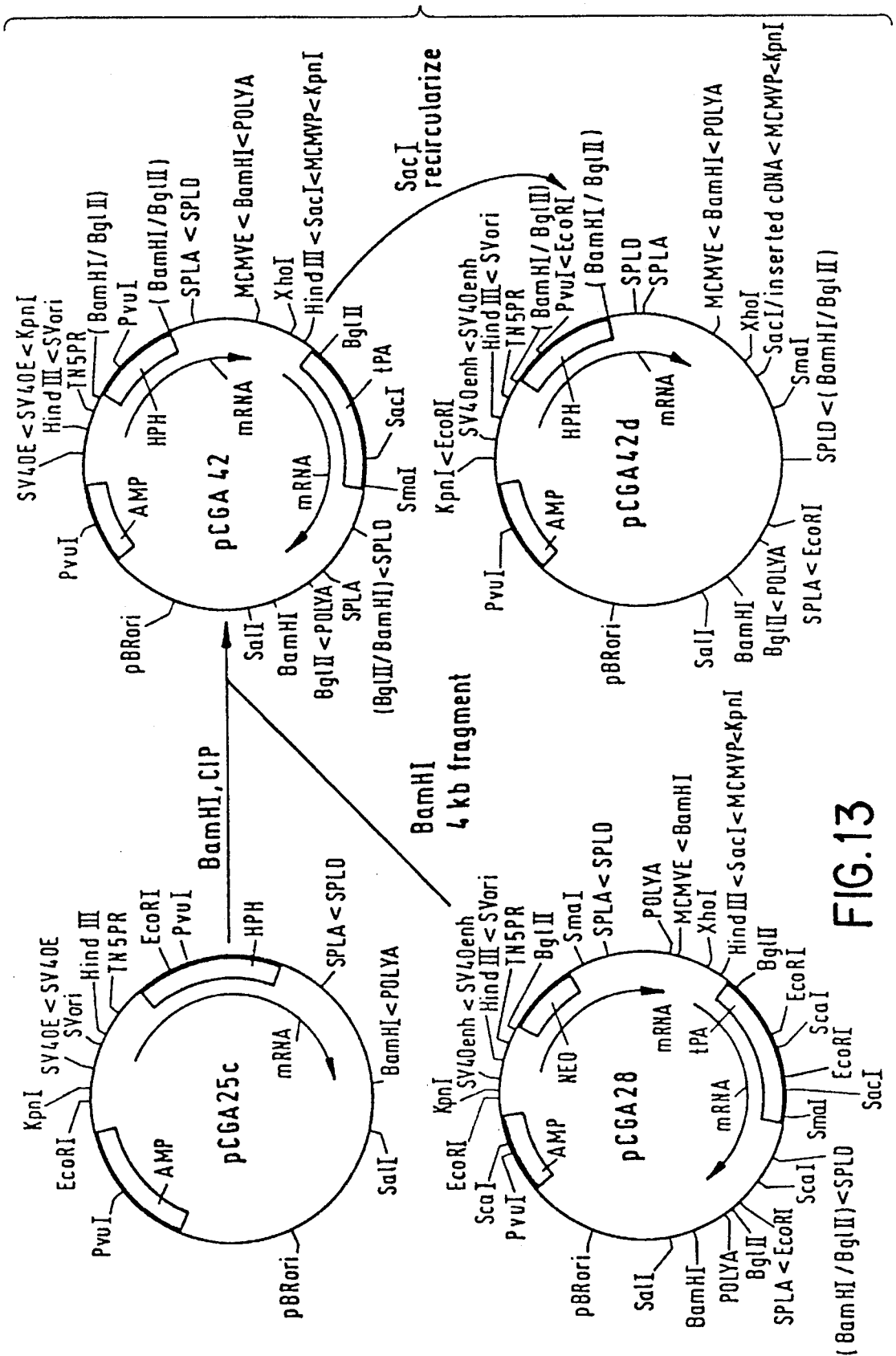
FIG. 13 schematically illustrates the construction of t-PA expression plasmid pCGA42 and of universal expression plasmid pCGA42d, both plasmids including the hygromycin resistance gene.
Figure 14:
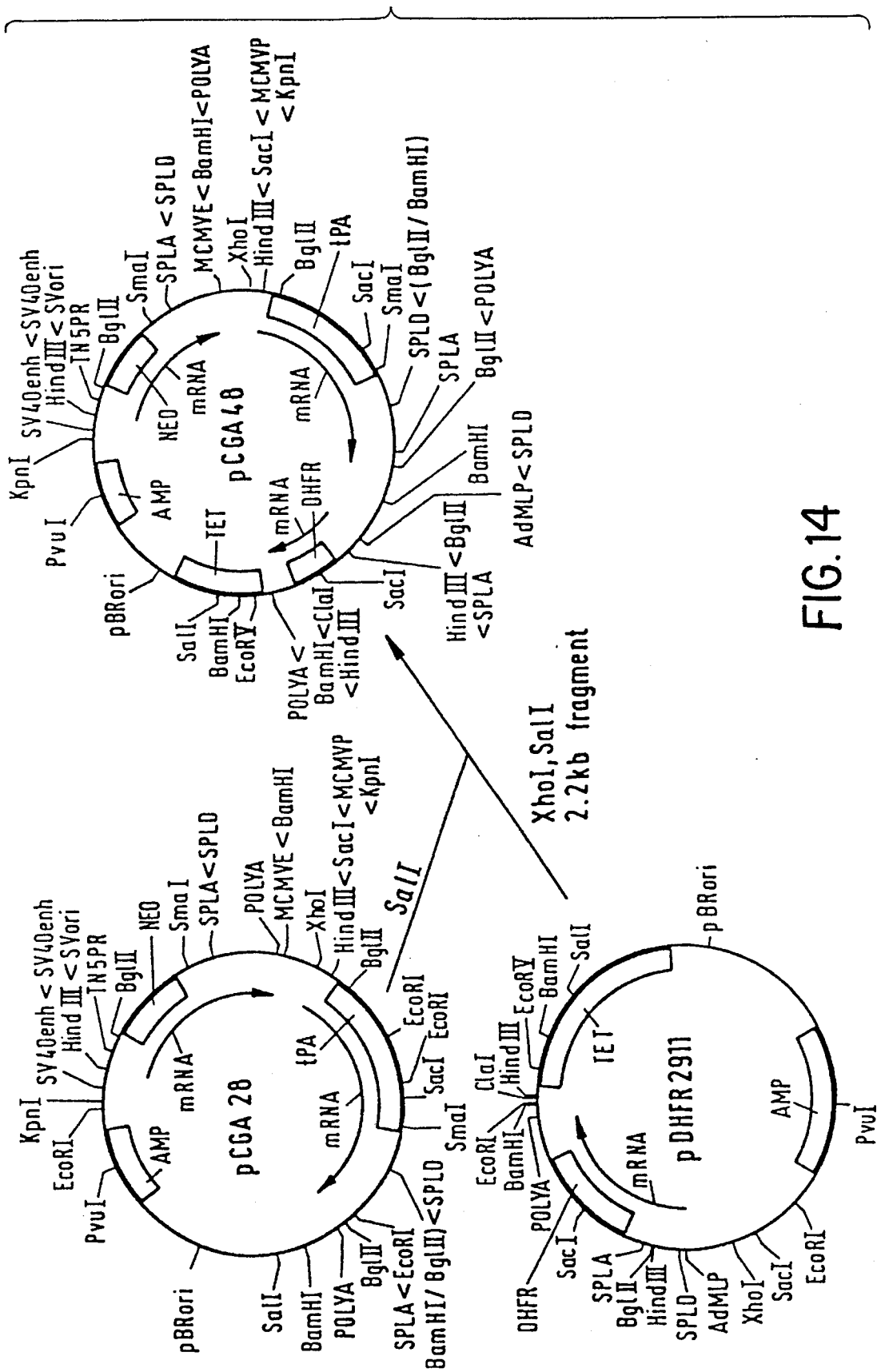
FIG. 14 schematically illustrates the construction of t-PA expression plasmid pCGA48 including the neomycin resistance gene and the DHFR gene.

Plasmid pCGA28 contains two SacI sites, one originally part of a linker just behind the MCMV promoter, the other in the t-PA cDNA. The sequence between the SacI sites is deleted by cutting first with the restriction enzyme, purifying the large fragment via an agarose gel and circularizing this linear DNA using $T_4$ DNA ligase, forming plasmid pCGA44 (see FIG. 12). Any cDNA cloned into the proper orientation into the now unique SacI site of pCGA44 effectively replace the t-PA coding sequence in pCGA28 and is efficiently expressed.

pCGA42d is derived from pCGA42 by deleting the 1.4 kb SacI fragment (see FIG. 13). Into the now unique SacI site cDNAs other than t-PA cDNA can be inserted and expressed at high levels in tissue culture cells.

Example 5: Insertion of u-PA, t-PA and hybrid PA cDNAs into expression vector pCGA28

Figure 15:
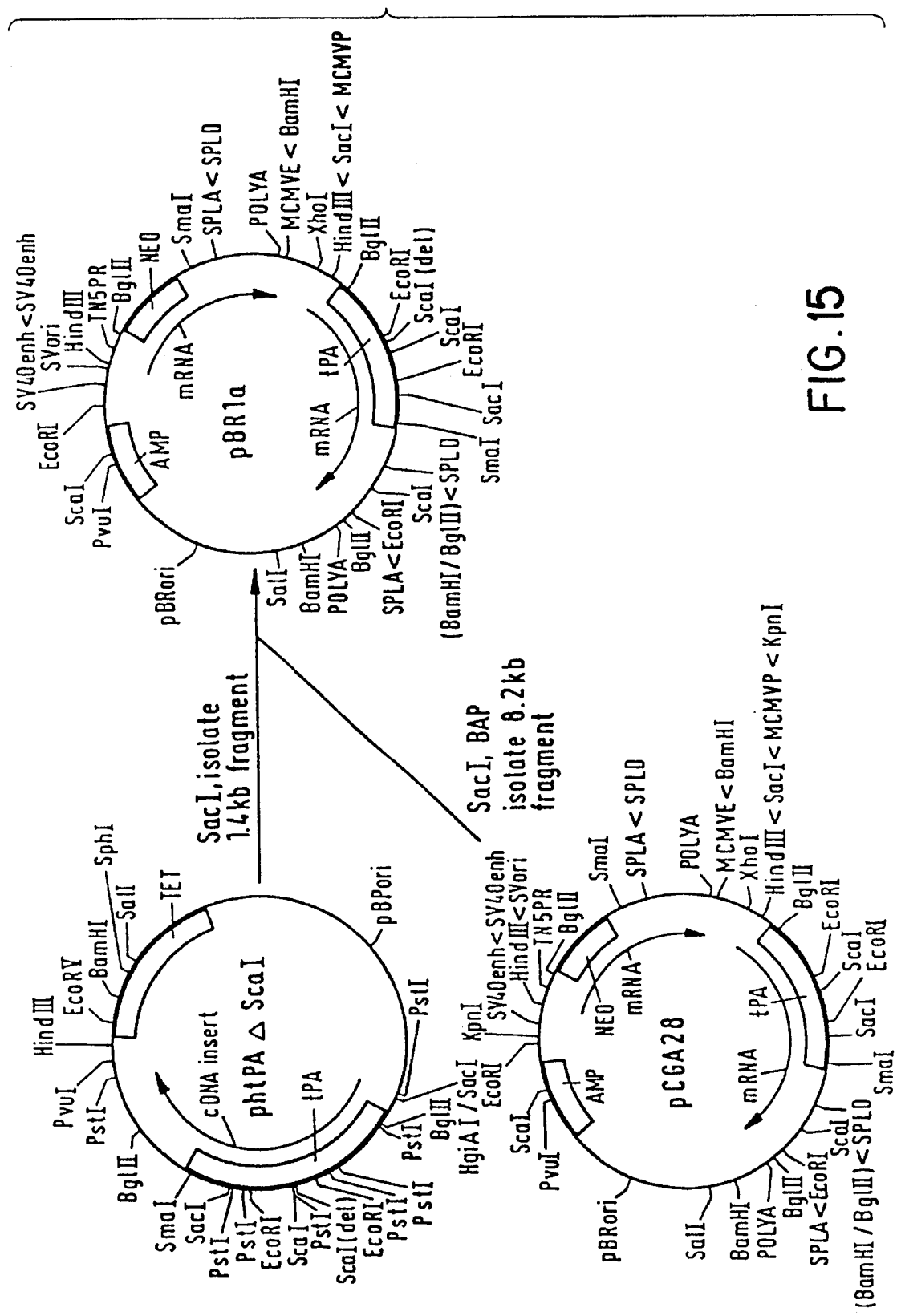
FIG. 15 schematically illustrates the construction of expression plasmid pBRla containing the mutated t-PA cDNA insert of plasmid ph·tPAΔScaI.

A) Insertion of t-PA cDNA (see FIG. 15)

In this construct, the t-PA cDNA fragment from plasmid ph·tPAΔScaI is inserted into pCGA28. This construct is deemed necessary to serve as a control for any changes that might inadvertently have occured during the restructuring of the ScaI site. The 1.4 kb SacI fragment is recovered from plasmid ph·tPA3ScaI after SacI digestion. The expression vector pCGA28 is also cleaved with SacI and the 8.2 kb vector fragment is isolated and dephosphorylated in a 100 μl reaction mixture containing 0.1 mM Tris pH 8.0, 0.1% SDS and 0.02 units bacterial alkaline phosphatase. Following incubation at 60° C. for 30 min, the reaction is phenol and ether extracted twice and then ethanol precipitated. The pellet is dissolved in water and an aliquot of it used for ligation to the 1.4 kb SacI fragment from ph·tPAΔScaI. The ligation mix is used to transform *E. coli* HB101 and minilysate DNA prepared from ampicillin resistant colonies is digested with appropriate restriction enzymes to verify if the SacI insert is in the desired orientation. The plasmid having the desired orientation is called pBR1A. The plasmid with the SacI fragment in the opposite orientation is termed pBR1B.

Figure 16:
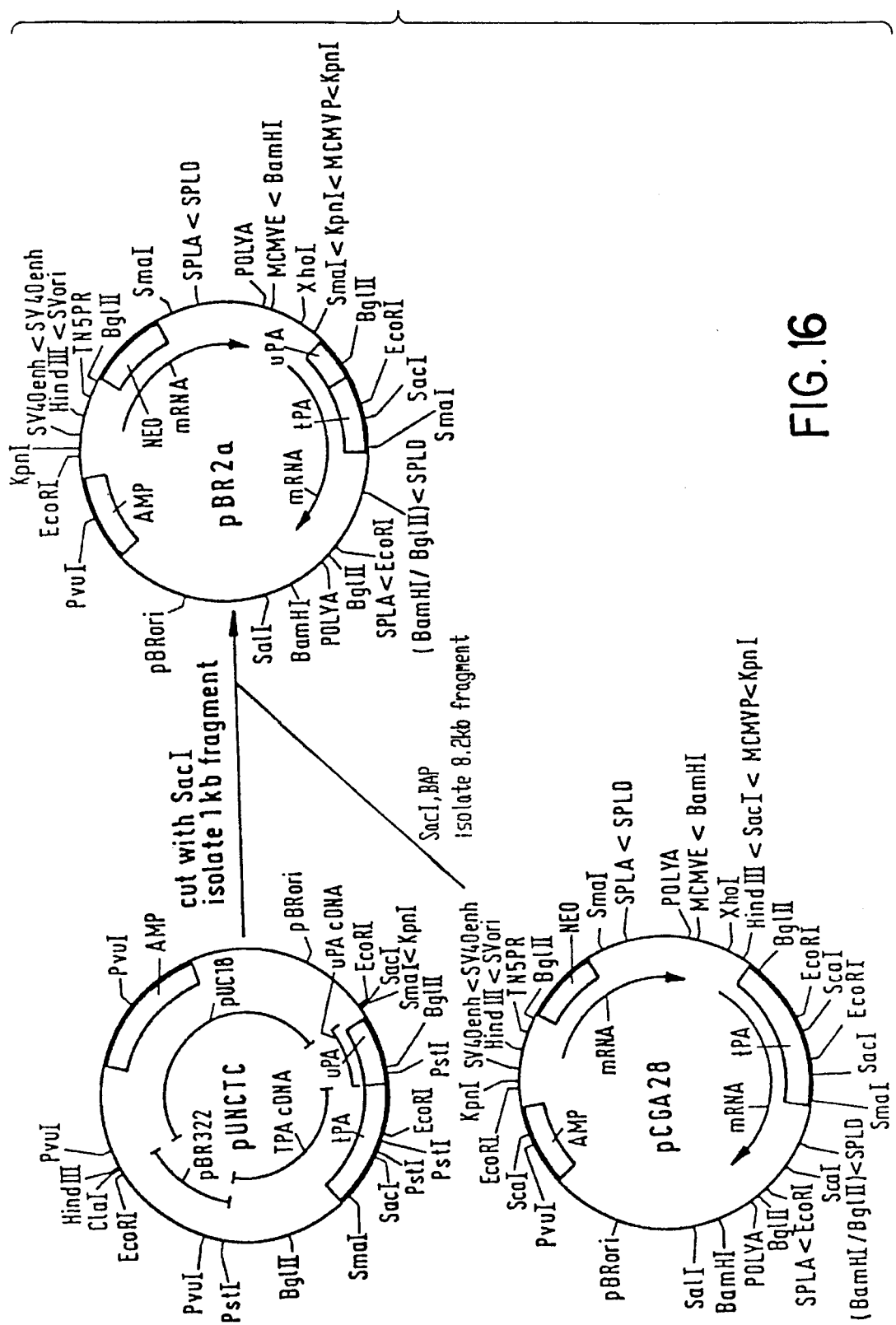
FIG. 16 schematically shows the construction of expression plasmid pBR2a containing a hybrid PA cDNA insert comprising the A-chain domains of u-PA and the B-chain of 't-PA.

B) Insertion of hybrid UPA$^A$TPA$^B$ cDNA (see FIG. 16)

In this construct, the hybrid UPA$^A$TPA$^B$ cDNA fragment from plasmid pUNC·tc is inserted into the expression vector pCGA28. pUNC·tc DNA is digested with SmaI (cf. FIG. 7), the 1.24 kb fragment is isolated and ligated to SacI digested, dephosphorylated 8.2 kb pCGA28 vector DNA. *E. coli* HB101 cells are transformed with the ligation mix and colonies containing the SacI insert in the desired orientation identified by performing restriction digests on minilysate DNA. The plasmid with the pUNC·tc DNA insert in the desired orientation is designated pBR2A and the one with the opposite orientation pBR2B.

Figure 17:
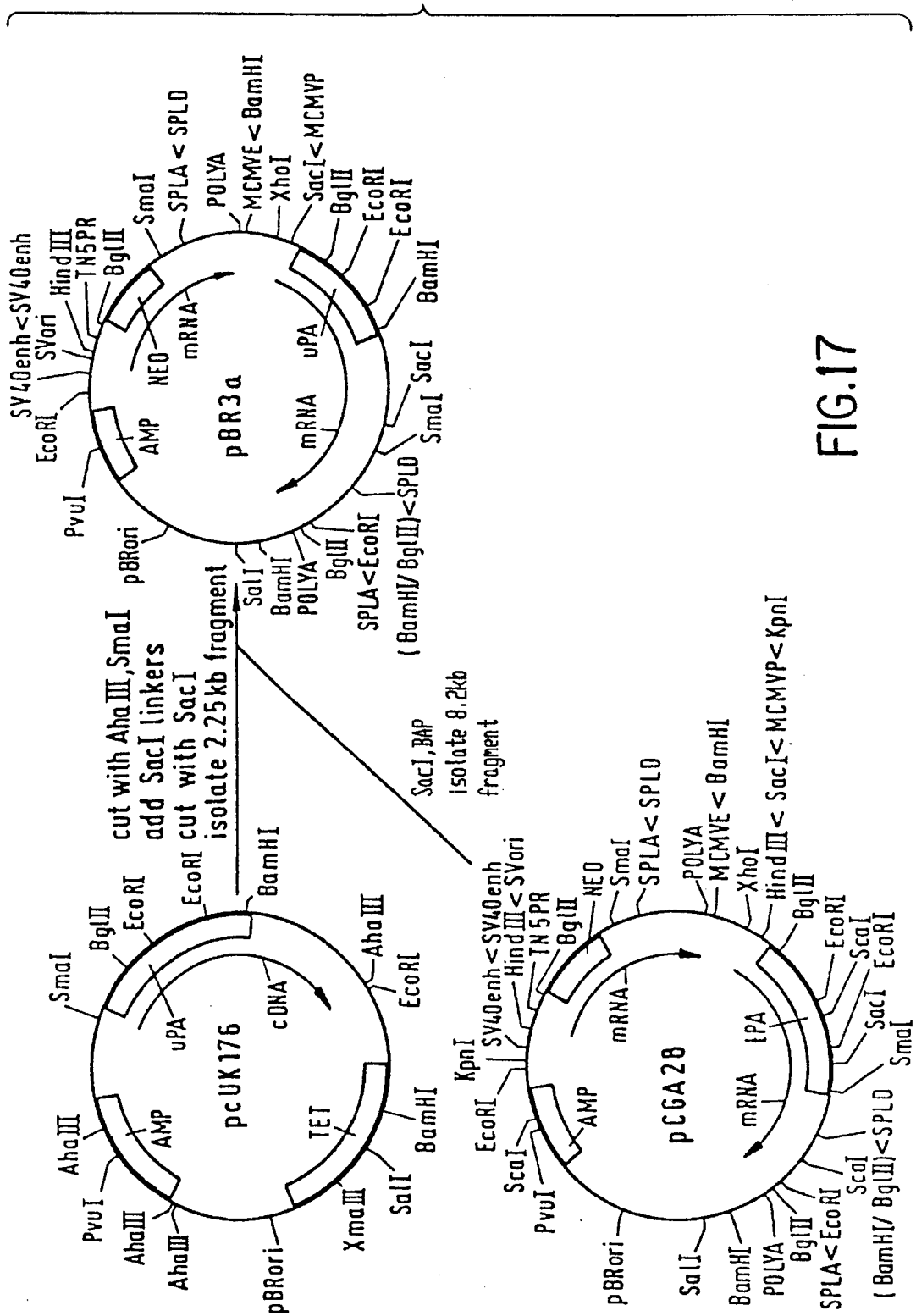
Figure 18:
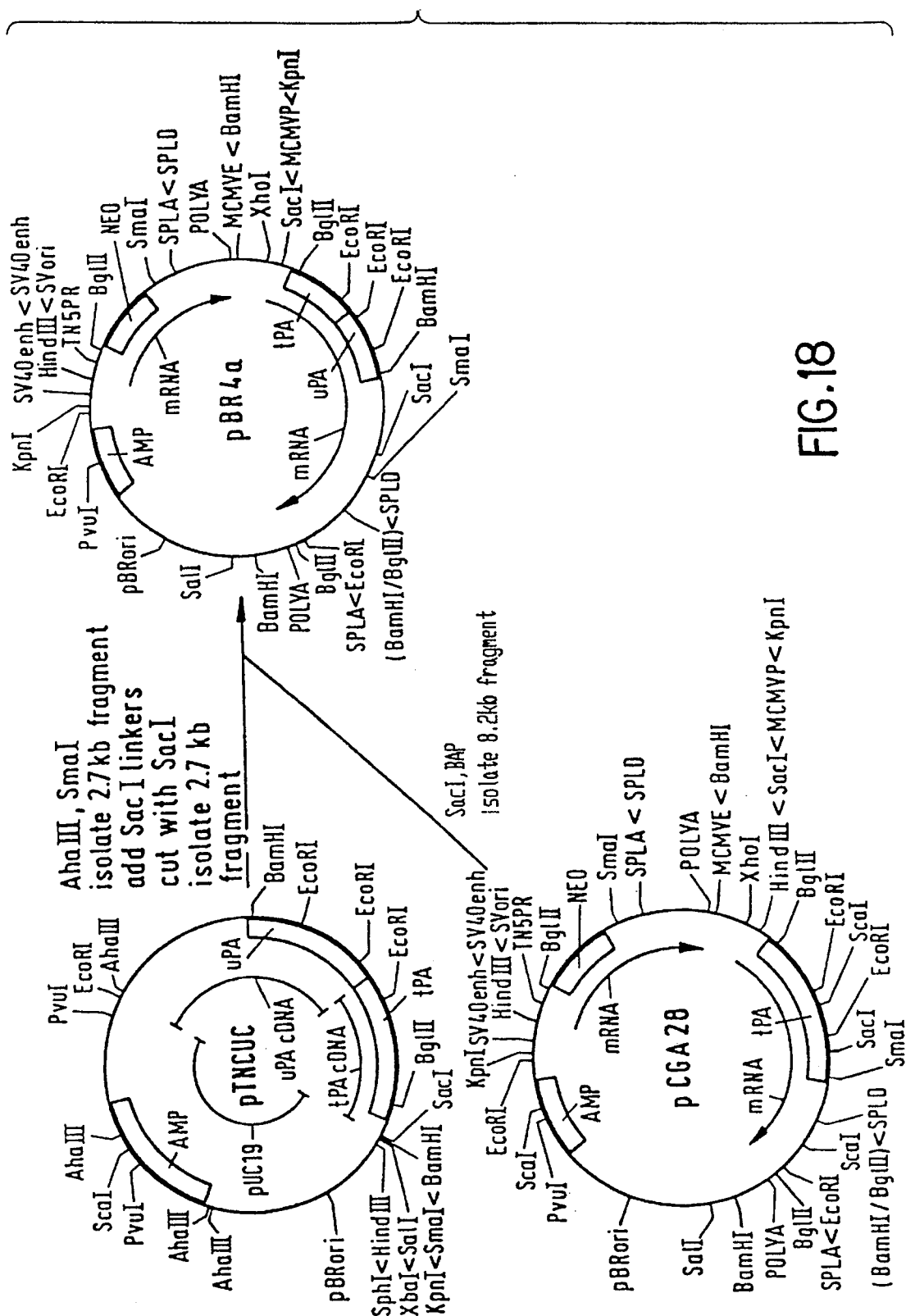
FIG. 18 schematically illustrates the construction of expression plasmid pBR4a containing a hybrid PA cDNA insert comprising the A-chain domains of t-PA and the B-chain of u-PA.

C) Insertion of u-PA cDNA (see FIG. 17)

In this construct, human u-PA DNA is inserted into the expression vector pCGA28 and together with pBR1 this plasmid serves as the parent plasmid control and confirms the usefulness of pCGA28-type vectors. Plasmid pcUK176 is digested with SmaI, AhaIII (cf. FIG. 4), the 2.25 kb fragment isolated, and ligared to phosphorylated SacI linker as described above. Following SacI digestion, the 2.25 kb fragment is recovered and ligated to Sac I digested, dephosphorylated 8.2 kb pCGA28 DNA fragment. *E. coli* HB101 is transformed and colonies harbouring desired plasmid identified by digesting minilysate DNA with restriction enzymes. The plasmid with the human u-PA DNA in the correct orientation is designated pBR3A and that in the opposite orientation pBR3B.

D) Insertion of hybrid TPA$^A$UPA$^B$ cDNA (FIE. 18) Here, the hybrid TPA$^A$UPA$^B$ cDNA from plasmid ptNC·UC is inserted into the expression vector pCGA28. The 2.75 kb SmaI (present in the vector), AhaIII fragment is isolated from the ptNC·UC DNA, ligated to phosphorylated SacI linker, the linker ligated 2.75 kb fragment recovered and ligated to SacI digested, dephosphorylated vector DNA and the desired colonies identified as described above. The plasmid with the ptNC·UC DNA insert in the correct orientation is called pBR4A.

Example 6: Construction of a yeast expression vector containing the PHO5 promoter, the invertase signal sequence and the t-PA coding region A) Synthesis of oligodeoxvribonucleotides for invertase signal sequence:

Four oligodeoxyribonuclotides: I-1, I-2, I-3, I-4 are synthesized by DNA synthesizer (model 380B Applied Biosystems). After deblocking the synthetic fragments are purified on a 12% polyacrylamide gel containing 8 M urea. Salt-free pure oligodeoxyribonucleotides are obtained using Sep. Pak (Waters Associates). These fragments constitute a duplex which encodes the invertase signal sequence with the frequently used yeast codons.

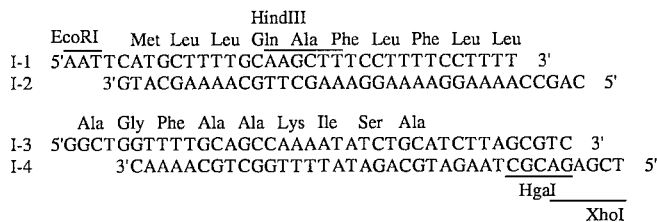

B) Subcloning of the invertase signal sequence in plasmid p31 a) Preparation of vector:

1.5 Bg of p31R/SS-TPAΔ2 (European Patent Application No. 143,081) is digested with 10 U of EcoRI (Boehringer) in 50 μl of 10 mM Tris.HCl pH 7.5, 6 mM MgCl₂, 100 mM NaCl, 6 mM mercaptoethanol for one hour at 37° C. After adding 1 μl of 2.5 M Na/Cl, 10 U of XhoI (Boehringer) are added and incubated at 37° C. for one hour. The 4.2 kb vector is isolated on a 0.8% preparative agarose gel. The gel slice is transferred to a Micro Colloidor tube (Sartorius GmbH), covered with 200 μl of TE and electroeluted (electrophoresed at 90 mA for 50 min). The TE solution is collected and precipitated in 2.5 volumes of absolute ethanol after the addition of 0.1 volume 10×TNE. The DNA pellet is washed with cold 80% ethanol and dried in vacuum. The DNA is resuspended in 6 μl TE (40 μmoles/pl).

b) Annealing oligodeoxvribonucleotides (I-1, I-2, I-3, I-4), kination and ligation with vector A solution containing 10 μmoles of each of the four deoxyribonucleotides in 10 μl of 0.5 M Tris·HCl pH 8 is incubated at 95°·C. for 5 minutes on a water bath. The water bath is slowly cooled to 30° C. over a period of 5 hours. To this annealed mixture is added 2 μl each of 0.1 M MgCl₂, 0.1 M NaCl, 30 mM DTT, 4 mM ATP and 8 U (1 μl) of polynucleotide kinase (Boehringer). Kination is carried out at 37° C. for one hour. The annealed, kinased oligodeoxyribonucleotides and 60 μmoles of p31R/SS-TPAA2 cut vector (1.5 μl) are ligated with 400 U (1 pl) of T4 DNA ligase (Biolabs) at 14° C. for 17 hours. The reaction is stopped by incubation at 65° C. for 10 min. 10 pl of this ligation mixture is used for transformation of E. coli HB101 Ca⁺⁺ cells [M. Dagert and S. D. Ehrlich, Gene 56, 23–28 (1979)]. 20 amp^R colonies are picked. DNA is prepared by the quick isolation procedure (D. S. Holmes and M. Quigley. Anal. Biochem. 114, 193–197 (1981)]. DNA is digested with EcoRI and XhoI, radiolabelled at the EcoRI end and analysed on a 6% polyacryalmide gel containing 8 M urea using radiolabelled pBR322 HaeIII cut DNA as marker. Correct size bands are observed for DNA obtained from all the 20 clones. One clone is grown in 100 ml LB medium containing 100 μg/ml of ampicillin. Plasmid DNA is isolated and is referred to as p31RIT-12.

Figure 19:
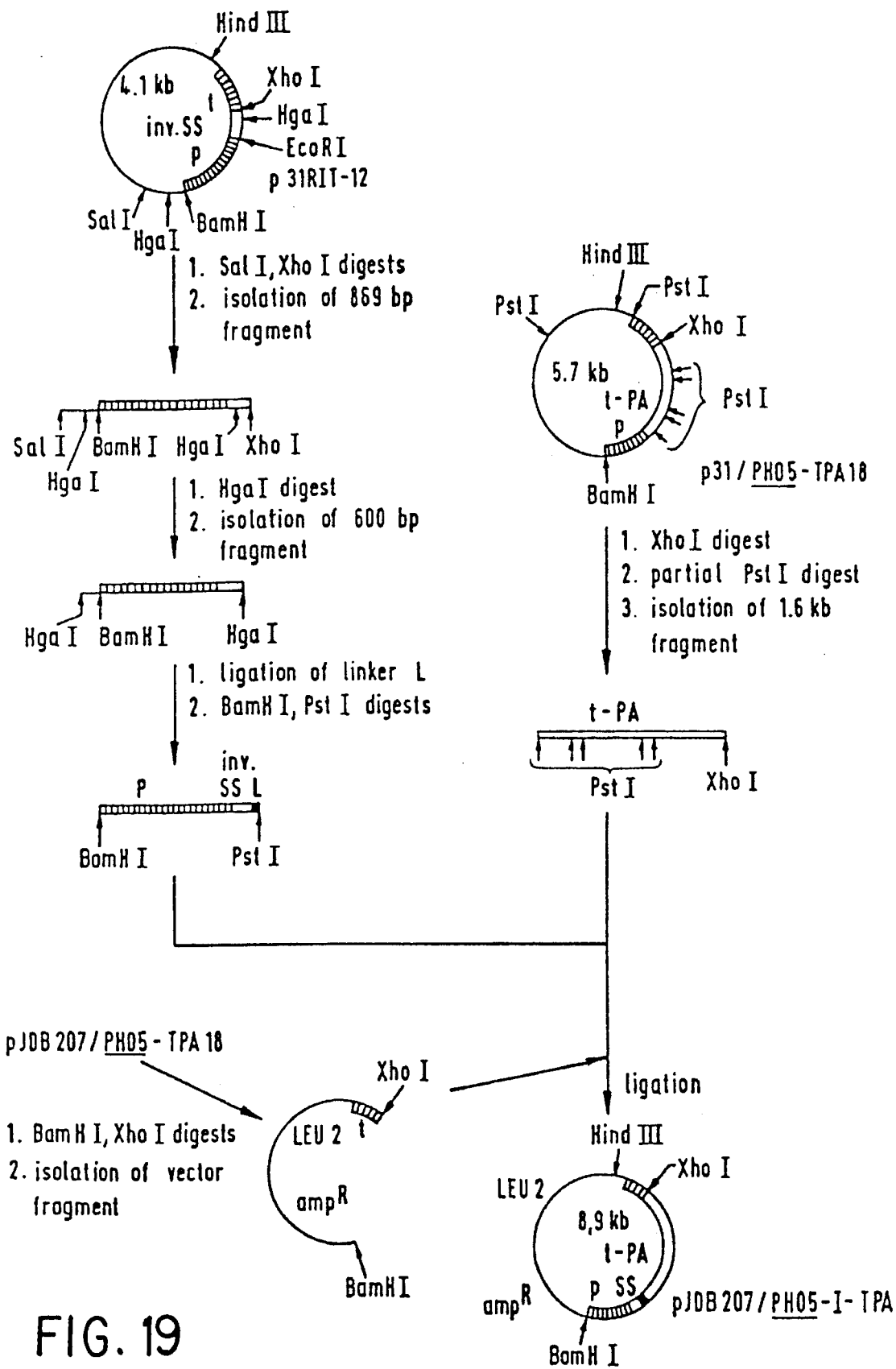
FIG. 19 schematically shows the construction of yeast expression vector pJDB207/PHO5-I-TPA containing the PHO5 promoter, the invertase signal sequence and t-PA cDNA.

C) Construction of pJDB207/PH05-I-TPA (see FIG. 19)

a) Preparation of vector:

Three μg of pJDB207/PHO5-TPA18 (European Patent Application No. 143,081) is incubated at 37° C. for one hour with 10 U of BamHI in 50 μl of 10 mM Tris·HCl pH 7.5, 6 mM MgCl₂, 100 aM NaCl, 6 mM mercaptoethanol. An aliquot is checked on a 1% agarose gel in TBE buffer to confirm complete digestion. The digest is incubated at 65° C. for 10 min. Then 0.5 μl of 5 M NaCl is added folloved by 15 U of XhoI (Boehringer). This is incubated at 37° C. for one hour. The 6.8 kb vector is isolated on a 0.8% prepacative agarose gel. The DNA is extracted by electroelution and after precipitation dissolved in TE.

b) XhoI digest of p31/PHOS-TPA18:

Thirty μg of p31/PHOS-TPA18 (European Patent Application No. 143,081) are incubated at 37° C. for one hour with 60 U of XhoI (15 U/μl) in 200 μl of 10 mM Tris·HCl pH 8, 6 mM MgCl₂, 150 mM NaCl, 6 mM mercaptoethanol, extracted with an equal volume of phenol-chloroform, and precipitated in ethanol.

c) Partial PstI digest of XhoI cut p31/PHO5-TPA18

The precipitated XhoI cut p31/PHO5-TPA18 DNA is resuspended in 250 μl of 10 mM Tris-MC1 pM 7.5, 6 mM MgCl₂, 50 mM NaCl, 6 mM mercaptoethanol, 2,5 mg ethidium bromide, incubated at 37° C. for 35 minutes with 22.5 U of PstI, and extracted with an equal volume of phenol, followed by an equal volume of chloroform-isoamylalcohol (50:1). The 1.6 kb fragment is isolated on a 1%; preparative agarose gel. The DNA is extracted by electroelution and precipitated [insert 1].

d) SalI-XhoI digest of p31RIT-12:

Thirty μg p31RIT-12 are incubated at 37° C. for one hour with 60 U of SalI (Boehringer 12 U/μl) and 60 U of XhoI (15 U/μl)) in 200 μl of 10 mM Tris·HCl pH 8, 6 mM MgCl₂, 150 mM NaCl, 6 mM mercaptoethanol, extracted with an equal volume of phenol-chloroform and precipitated in ethanol. The 869 bp fragment is isolated on a 1.2% preparative agarose gel. The DNA is extracted by electroelution desalted over DE-52, and precipitated in ethanol.

e) HEal diEest of SalI-XhoI cut p31RIT-12

SalI-XhoI cut p31RIT-12 is resuspended in 100 μl of 6 mM Tris·HCl pH 7.5, 10 mM HgCl₂, 50 mM NaCl, 1 mM dithiothreitol, 10 mg bovine serum albumin and is incubated at 37° C. for one hour with 6 U of HgaI (Biolabs, 0.5 U/μl)). The 600 bp fragment is isolated on a 1.2% agarose gel. The DNA is extracted by electroelution and precipitated in ethanol.

f) Annealing of linker oligonucleotides 90 μmoles of two oligodeoxyribonucleotides having the sequences

```
         HgaI              PstI
5'  CTGCATCTTACCAAGTGATCTGCA  3'
       3'AGAATGGTTCACTAG  5'
``` are suspended in 10 pl of 0.5 mM Tris·HCl pH 8 in a siliconized Eppendorf tube. The solution is incubated at 95° C. for 5 min and then slowly cooled to room temperature overnight.

g) Kination of linker

To the above solution is added 2 μl of 0.1 M KCl, 2 μl of 0.1 M MgCl₂, 3 μl of 30 mM DTT, 1 μl of 200 mM ATP, 8 U of polynucleotide (8U/pl). This is incubated at 37° C. for one hour.

h) Ligation of the HEaI fragment from p31RIT-12 with the kinased linker

The kinased linker solution is transferred to a tube containing the dry HgaI fragment, and 400 U of T₄ DNA ligase is then added. The solution is incubated at room temperature (21°–22° C.) for 90 minutes, diluted to 100 µl with TE and extracted with an equal volume of phenol-chloroform. The fragment is precipitated by adding 0.6 volume of isopropanol and 0.1 volume of 3 M sodium acetate at room temperature to the aqueous solution.

i) BamHI-PstI digest of above

The above dry DNA is digested with 10 U of BamHI and 10 U of PstI in 20 µl of 10 mM Tris·HCl pH 7.5, 100 mM HgCl$_2$, 6 mM mercaptoethanol for one hour at 37° C. After dilution to 100 µl the solution is extracted with an equal volume of phenol-chloroform, and the aqueous layer is precipitated in isopropanol [insert 2].

j) Ligation of the three fragments 100 fmoles of pJDB207/PHO5-TPA18 BamHI-XhoI cut vector fragment, 200 fmoles of each of the other two insert fragments [1 and 2]are ligated in 10 µl of 50 mH Tris·HCl pH 7.5, 10 mH HgCl$_2$, 10 mH DTT, 2 mM ATP, 0.5 µg gelatin with 400 U of T$_4$ DNA ligase for 16 hours at 15° C. The reaction is stopped by incubation at 65° C. for 10 min. 5 µl of this ligation mixture is used for transformation of E. coli HB101 Ca$^{++}$ cells. 10 amp$^R$ colonies are picked and DNA is prepared by the quick isolation procedure. On analysis with EcoRI, PstI and BamHI-HindIII correct size fragments are observed. One clone is grown in 100 ml of LB medium containing 100 µg/ml of ampicillin. Plasmid DNA is isolated and is referred to as pJDB 207/PHO5-I-TPA.

Example 7: Construction of plasmid pCS16/UPA comprising the u-PA coding region

Figure 20:
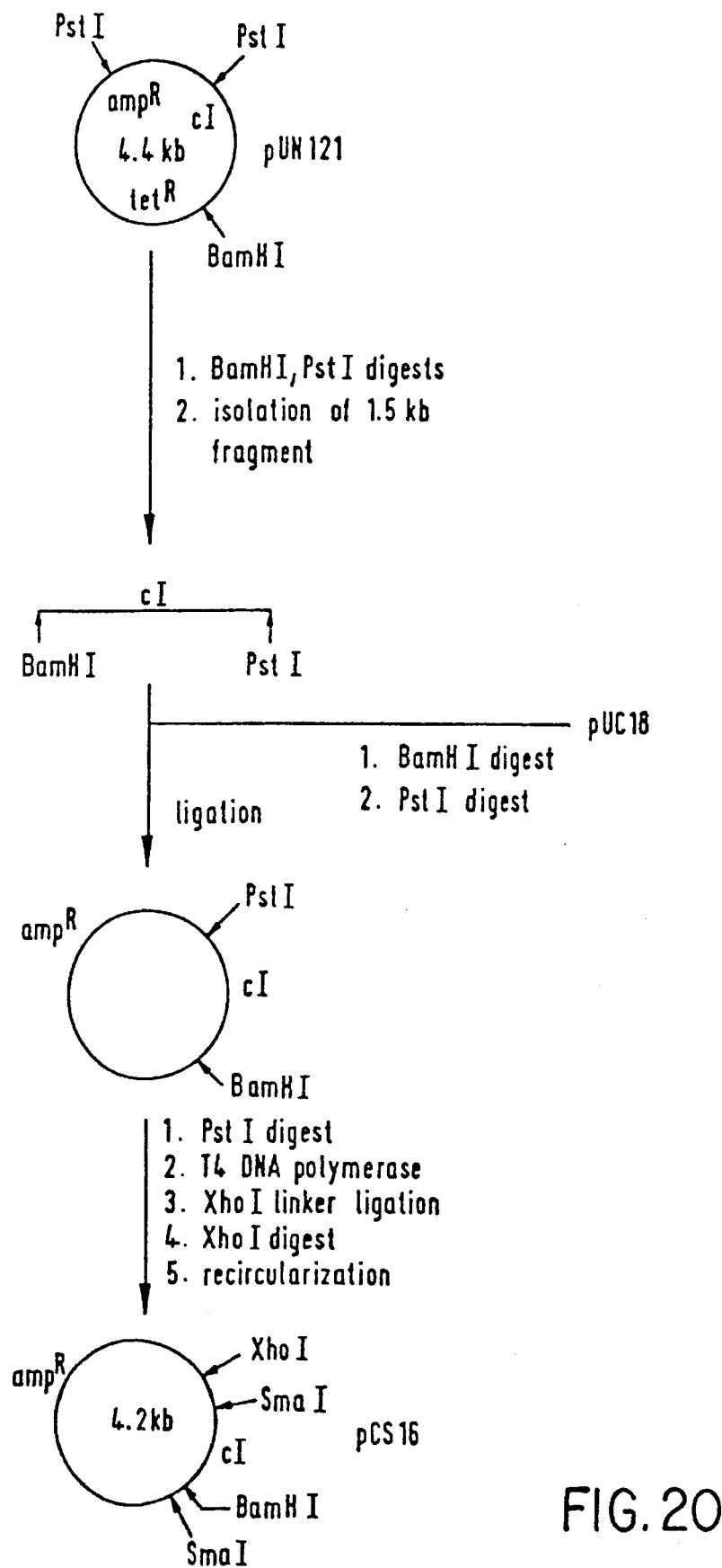
FIG. 20 schematically illustrates the construction of plasmid pCS16.

A) Construction of plasmid pCS16 (see FIG. 20)

A 1.5 kb PstI-BamHI fragment of plasmid pUN121 [B. Nilsson et al. Nucl. Acids Res. 11, 8019–8030 (1983)] comprising the cI gene of phage lambda and part of the tetracyclin resistance gene is cloned into pUC18 [J. Norrander et al Gene 26, 101–106 (1983)] cut with PstI and BamHI The resulting clone is digested with Peri. The 3' overhanging ends are removed in a reaction with T$_4$ DNA polymerage and XhoI linkers are ligated to the blunt ends. After digestion with XhoI the molecule is recircularised by ligation. An aliquot of the ligation mixture is used to transform Ca treated E. coli HB101 cells. The DNA of individual ampicillin resistant, transformed colonies is analysed. One of several correct clones is chosen and referred to as pCS16.

Figure 21:
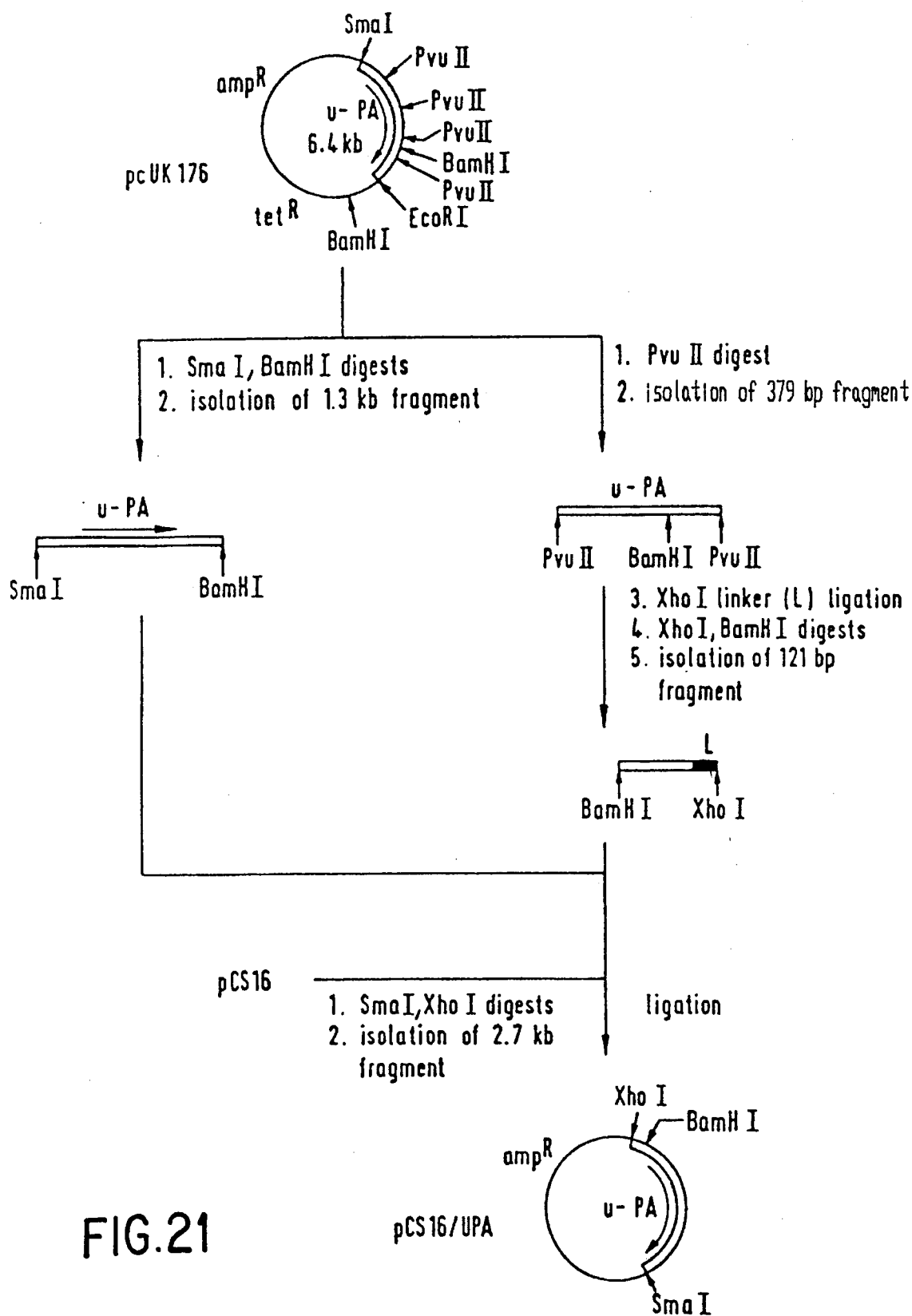
FIG. 21 schematically illustrates the construction of plasmid pCS16/UPA comprising the u-PA cDNA.

B) Construction of plasmid pCS16/UPA (see FIG. 21)

The urokinase cDNA as comprised in plasmid pcUK176 (see Example 2) is subcloned in plasmid pCS16. The subcloned cDNA extends from the SmaI site in the 5' nontranslated region (FIG. 4) to the PvuII site at nucleotide positions 1439–1444 in the 3' nontranslated region (numbering according to FIG. 3).

15 µg of plasmid pcUK176 are digested with PvuII. The 379 bp PvuII fragment is isolated from other fragments on a 1,5% agarose gel in Tris-borate-EDTA buffer pH 8.3. The DNA is electroeluted, purified by DE52 (W harman) ion exchange chromatography and precipitated by ethanol. 1.2 µg of single stranded XhoI linkers (5'-CCTCGAGG-3') are phosphorylated at their 5' ends, heated for 10 min at 75° C., self annealed during cooling to room temperature and stored at −20° C. 0.9 µg of the kinased, double stranded XhoI linkers are ligated at an 80-fold molar excess to the blunt ends of the 379 bp PvuII fragment of pcUK176 (see above) in 20 µl of 60 mM Tris-HCl pH 7.5, 10 mM MgCl$_2$, 5 mM DTT, 3.5 mM ATP and 400 units of T$_4$ DNA ligase (Biolabs) at 15° C. for 16 hours. The mixture is heated for 10 min at 85° C. Excess linker molecules are removed by precipitation with 0.54 volumes of isopropanol in the presence of 10 mM EDTA and 300 mM sodium acetate pH 6.0 for 30 min at room temperature. The DNA is digested with XhoI and BamHI. A 121 bp BamHI-XhoI fragment is isolated on a 1.5% agerose gel in Tris-borate EDTA buffer pH 8.3.

6 µg of plasmid pcUK176 are digested with SmaI and BamHI. A 1.3 kb SmaI-BamHI fragment comprising most of the u-PA coding sequence is isolated. 6 µg of plasmid pCS16 are digested with SmaI and XhoI. The 2.7 kb vector fragment is isolated. The DNA fragments are electroeluted from the gel and ethanol precipitated. 0.2 µmoles of the 1.3 kb SmaI-BamHI fragment, 0.2 µmoles of the 121 bp BamHI-XhoI fragment (both fragments together comprise the full u-PA coding sequence) and 0.1 µmoles of the 2.7 kb vector fragment are ligated in 10 pl of 60 mH Tris·HCl pH 7.5, 10 mH HgCl$_2$, 5 mH DTT, 3.5 mH ATP and 400 units of T$_4$ DNA ligase at 150° C. One and 3 µl aliquots of the ligation mixture are added to 100 µl of Ca$^{++}$ treated E. coli HB101 cells. Transformation is carried out as described [A. Hinnen et. el., Proc. Natl. Aced. Sci. USA 75, 1929 (1978)]. 12 ampicillin resistant colonies are grown in LB medium containing 100 mg/1 ampicillin. DNA is isolated according to Holmes et el. [Anal. Biochem. 114, 193 (1981)] and analysed by EcoRI, PvuII and XhoI restriction digests. One clone with the expected restriction fragments is referred to as pCS16/UPA.

Figure 22:
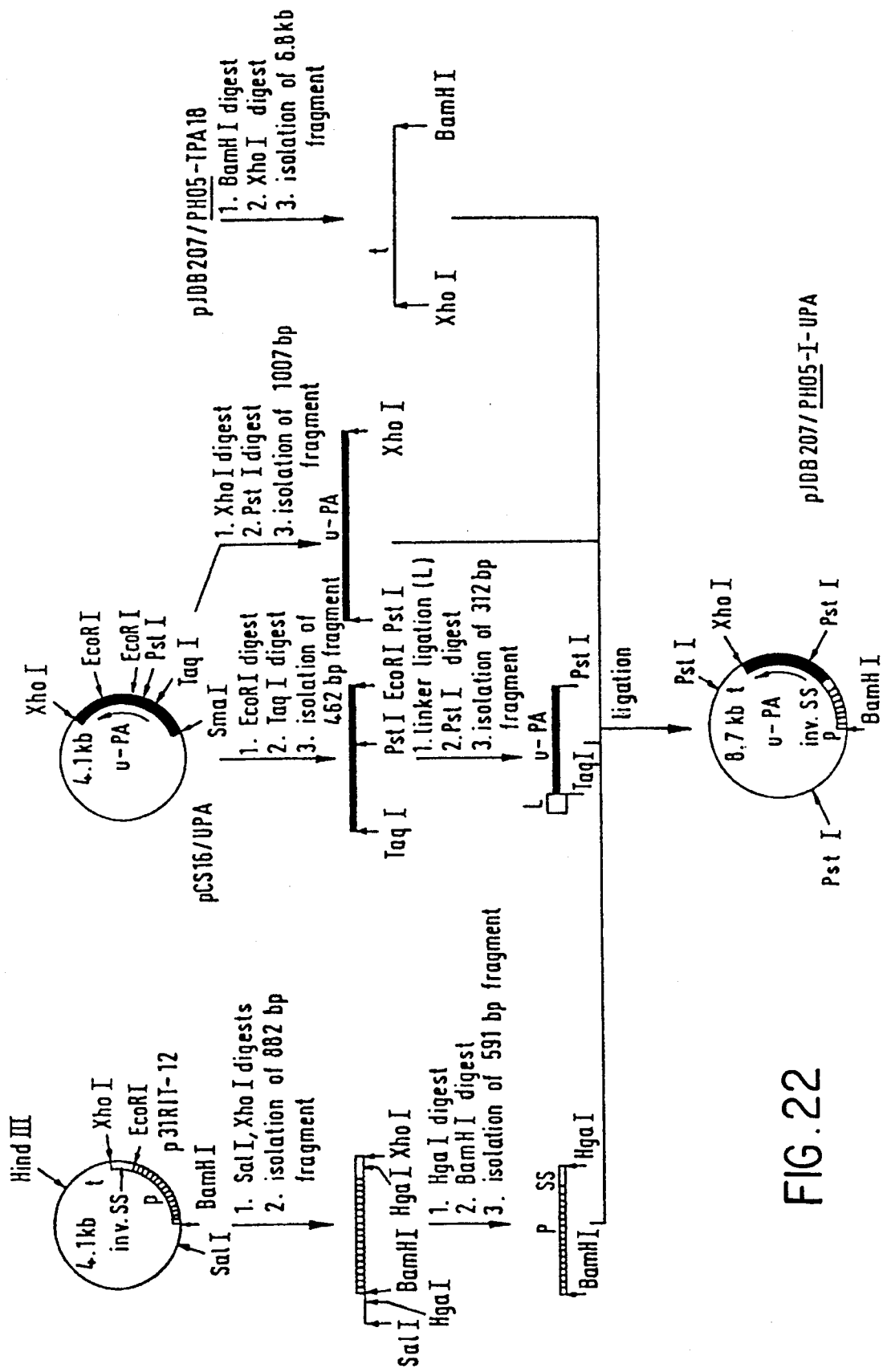
FIG. 22 schematically shows the construction of plasmid pJDB207/PH05-I-UPA.

Example 8: Construction of plasmid pJDB207/PHO5-I-UPA (FIG. 22)

pJDB207/PHO5-I-UPA contains the PHO5 promoter, the invertase signal sequence, the coding sequence of mature urokinase and the PHO5 transcription terminator in a tandem array cloned into the pJDB207 yeast expression vector.

20 µg of plasmid pCS16/UPA are digested to completion with 40 units of EcoRI. After phenol extraction and ethanol precipitation the EcoRI digested DNA is further cut by TaqI at 65° C. The resulting fragments are separated on a preparative 1.2% agarose gel. The 462 bp TaqI-EcoRI fragment is isolated by electroelution from the gel and ethanol precipitation.

An oligodesoxyribonucleotide linker of the formula (I)  5'-CTGCAAGCAATGAACTTCATCAAGTTCCAT-3'

(II)  3'-       TCGTTACTTGAAGTAGTTCAAGGTAGC-5' is ligated to the TaqI site of the DNA fragment. The linker restores the 5' terminus of the coding sequence of mature u-PA (nucleotides 130–154, FIG. 3) and establishes the in frame fusion to the invertase signal sequence. The 5'-CTGCA sequence of the linker fills the corresponding 3' recessed end of the invertase signal sequence created by HgaI cleavage.

300 µmoles each of the oligodesoxynucleotides Z and II are phosphorylated and annealed. 5.25 µg (600 µmoles) of phosphorylated, double-stranded linker DNA are ligated to 1.7 Mg (5.6 µmoles) of the 462 bp TaqI-EcoRI fragment (see above) in 175 pl of 60 mM Tris-HCl pH 7.5, 10 mM MgCl$_2$1 mM ATP, 5 mM DTT and 800 units of T4 DNA ligase at 15° C. for 16 hours. T4 DNA ligase is inactivated foc 10 min at 85° C. The excess of linkers is removed by precipitation in the presence of 10 mM EDTA, 300 mM sodium acetate pH 6.0 and 0.54 volumes of isopcopanol. The DNA is digested with PstI. An unique 312 bp fragment is isolated containing the linker attached to DNA sequences coding foc u-PA up to nucleotide 436 (PstI site, see FIG. 3). The DNA fragment is purified by electroelution and precipitation with ethanol.

Plasmid pCS16/UPA is digested with XhoI and PstI. A 1007 bp PstI-XhoI fragment is isolated and purified. This fragment contains most of the coding sequence for urokinase.

Plasmid p31RIT-12 (see Example 6B) is digested with SalI and XhoI. An 882 bp SalI-XhoI fragment is isolated from the gel by electroelution and ethanol precipitation. The fragment is further digested with BamHI and HgaI. A 591 bp BamHI-HgaI fragment is isolated which contains the PHO5 promoter region and the invertase signal sequence.

Plasmid pJDB207/PH05-TPA18 (see European Patent Application No. 143,081) is digested with BamHI and XhoI. The 6.8 kb vector fragment is isolated on a preparative 0.6% agarose gel in Tris-acetate buffer pH 8.2. The DNA is electroeluted and precipitated with ethanol.

All DNA fragments are resuspended in $H_2O$ at a concentration of 0.1 pmoles/µl. 0.2 µmoles of the 591 bp BamHI-HgaI fragment, 0.2 µmoles of the 312 bp HgaI-PstI fragment, 0.2 µmoles of the 1007 bp PstI-XhoI fragment and 0.1 µmoles of the 6.8 kb BamHI-XhoI vector fragment are ligated for 15 h at 15° C. in 10 µl of 50 mM Tris-HCl pH 7.5, 10 mM $MgCl_2$, 5 mM DTT, 1 mM ATP and 400 units of T4 DNA ligase. One µl of the ligation mixture is used to transform E. coli HB101 $Ca^{++}$ cells. 12 $amp^R$ colonies are picked and grown in LB medium containing 100 mg/l of ampicillin. DNA is prepared by the quick isolation procedure [D. S. Holmes et al., Anal. Biochem. 114, 193 (1981)]. On restriction digests of the plasmid DNA with HindIII and EcoRI the expected restriction fragments are observed. Plasmid DNA of a single clone is selected and referred to as pJDB207/PHO5-I-UPA.

Example 9: A t-PA/u-PA hybrid plasminogen activator with the t-PA A-chain domains and u-PA B-chain (primary DNA Construct)

Another approach for the construction of an in frame fusion of DNA sequences coding for the A-chain of t-PA and the B-chain of u-PA at a predetermined position consists in two steps: Firstly, convenient restriction fragments with the coding sequences are ligated. DNA is prepared in E. coli and subcloned in M13 to obtain single-stranded templates. In a second step excess nucleotide sequences are removed by in vitro mutagenesis. The exact in frame junction between the t-PA A-chain and the u-PA B-chain is at the activation site. The mutant DNA is subcloned in a suitable expression vector for yeast and mammalian cell lines.

a) Isolation of a DNA fragment coding for the t-PA A-chain:

10 µg of plasmid pJDB207/PHO5-I-TPA (see Example 6) are digested with BamHI and PvuII. The 1.7 kb BamHI-PvuII fragment is separated on a 0.8% agarose gel in Tris-borate-EDTA buffer pH 8.3. The DNA fragment contains the PHO5 promoter, the invertase signal sequence and the coding sequence of mature t-PA up to the PvuII restriction site [cf. FIG. 1; nucleotide positions 1305–1310]. The DNA is electroeluted, precipitated with ethanol and resuspended in $H_2O$ at a concentration of 0.1 µmoles/µl.

b) Isolation of a DNA fragment coding for the u-PA B-chain:

Plasmid pCS16/UPA (see Example 7B) is digested with BalI (cf. FIGS. 3 and 4, nucleotide positions 573–578) and XhoI. The 868 bp BalI-XhoI fragment is isolated as above and resuspended in $H_2O$ at a concentration of 0.1 µmole/µl.

c) Ligation of fragments to vector fragment:

Plasmid pJDB207/PHO5-TPA18 (European Patent Application No. 143,081) is digested with BamHI and XhoI. The 6.7 kb vector fragment is isolated on a 0.8% agarose gel in Tris-acetate buffer pH 8.2. The DNA is electroeluted, ethanol precipitated and resuspended in $H_2O$ at a concentration of 0.1 µmole/µl.

0.2 µmoles of the 1.7 kb BamHI-PvuII fragment, 0.2 µmoles of the 868 bp BalI-XhoI fragment and 0.1 µmoles of the 6.7 kb BamHI-XhoI vector fragment are ligated in 10 µl of 60 mM Tris-HCl pH 7.5, 10 mM $MgCl_2$, 5 mM DTT, 3,5 mM ATP and 400 units of $T_4$ DNA ligase (Biolabs) at 15° C. for 16 hours. One and 3 µl aliquots of the ligation mixture are added to 100 µl of Ca treated E. coli HB101 cells. Transformation is carried out as usual.

Six transformed, ampicillin resistant colonies are grown in LB medium containing 100 mg/l ampicillin. Plasmid DNA is prepared according to the method of Holmes et al. [Analyt. Biochem. 114, 193 (1981)] and analysed by restriction digests with BamHI and PstI. One clone with the expected restriction fragments is referred to as pJDB207/PHO5-I-$TPA^A UPA^B$.

Example 10: A u-PA/t-PA hybrid plasminogen activator with the u-PA A-chain domains and t-PA B-chain (primary DNA construct)

The primary hybrid DNA construct comprises the u-PA nucleotide sequences from the SmaI site to the EcoRI site (see FIG. 4) joined to t-PA nucleotide sequences from the ScaI site (positions 940–945) to the XhoI site introduced at position 1800 via an XhoI linker. The resulting hybrid DNA sequence contains excess nucleotides which are removed by in vitro mutagenesis. The exact, in frame junction between the u-PA A-chain and the t-PA B-chain is at the activation site.

a) Isolation of a DNA fragment coding foc the u-PA A-chain:

7 µg of plasmid pCS16/UPA are digested with EcoRI. The sticky ends of the resulting 3 fragments are converted to blunt ends by a fill-in reaction with 7.5 units of Klenow DNA polymerase (BRL) in the presence of 60 mM Tris·HCl pH 7.5, 10 mM $MgCl_2$, 0.1 mM dATP and 0.1 mM dTTP for 30 min at 25° C. The reaction is stopped by the addition of EDTA to a final concentration of 12.5 mM. The DNA is further digested with KpnI. A 619 bp KpnI-blunt [EcoRI] end fragment is isolated on a 1.5% agarose gel in Tris-borate-EDTA buffer pH 8.3, electroeluted and ethanol precipitated.

b) Isolation of a DNA fragment coding for the t-PA B-chain:

6 µg of plasmid pJDB207/PHOS-TPA18 are digested with ScaI and XhoI. A 860 bp fragment is isolated on a 1.2% agarose gel in Tris-borate EDTA buffer pH 8.3, electroeluted and ethanol precipitated.

c) Ligation of the DNA fragments to a pUC18 derived vector:

5 µg of plasmid pCS16/UPA (see Example 7) are digested with KpnI and XhoI. The resulting 2.7 kb fragment is isolated on a 0–8% agarose gel in Tris-borate-EDTA buffer pH 8.3. The DNA is electroeluted and ethanol precipitated. All DNA fragments are resuspended in $H_2O$ at a concentration of 0.1 µmoles/µl.

0.2 µmoles of the 619 bp Kpn-blunt end u-PA fragment, 0.2 µmoles of the 860 bp ScaI-XhoI t-PA fragment and 0.1 µmoles of the 2.7 kb KpnI-XhoI vector fragment are ligated as described above (Example 9). Ca$^{++}$ treated *E. coli* HB101 cells are transformed. 12 transformed, ampicillin resistant colonies are grown in LB medium supplemented with ampicillin (100 mg/l). DNA is prepared according to Holmes et al. (supra) and analysed by restriction digests with EcogI and PstI. A single clone with the expected restriction fragments is referred to as pCS16/UPA$^A$TPA$^B$.

Example 11: A u-PA/t-PA hybrid plasminogen activator with the second kringle and the catalytic B-chain of t-PA (primary construct)

A hybrid plasminogen activator gene comprising the DNA sequences of the urokinase "growth factor like" (U)-domain, the second kringle domain (K$_2$) of t-PA and the catalytic B-chain of c-PA is constructed in the following way: Two DNA restriction fragments coding for the u-PA growth factor domain and the t-PA K$_2$ kringle and B-chain, respectively, are ligated and inserted into plasmid pCS16. The resulting clone is called pCS16/UK$_2$TPA$^B$. A fragment containing the u-PA and t-PA coding sequences in subcloned in M13. In vitro mutagenesis is performed on single strand DNA to remove excess DNA sequences at the junction between u-PA and t-PA sequences.

5 µg of plasmid pCS16/UPA are digested with NcoI (nucleotide positions 326–331, see FIG. 4). The sticky ends of the restriction fragments are filled in a reaction with 5 units of Klenow DNA polymerase I (BRL) in the presence of 0.1 mM each of dATP, dTTP, dCTP, dGTP, 60 mM Tris·HCl pH 7.5, 10 mM MgCl$_2$ in 50 µl for 30 min at room temperature. The reaction is stopped by the addition of EDTA to a final concentration of 12.5 mM. The DNA is ethanol precipitated and further digested with XhoI. The 3 kb XhoI-blunt end [NcoI] fragment is isolated on a 0.8% agarose gel in iris-borate-EDTA pH 8,3, electroeluted and ethanol precipitated. This fragment contains the pCS16 vector and the coding sequence for the u-PA growth factor domain. 10 µg of plasmid pJDB207/PHO5-TPA18 (European patent application No. 143,081) are digested with BstXI [nucleotide positions 577–588]. The linear DNA fragment with 3' overhanging ends is incubated with 10 units of T. DNA polymerase (BRL) in 100 µl of 33 mM Iris-acetate pH 7.9, 66 mM potassium acetate, 10 mM magnesium acetate, 0.5 mM DTT and 0.1 mg/ml of bovine serum albumin for 2.5 min at 37° C. Then incubation is continued for 35 min at 37° C. in the presence of 0.1 mM each of dATP, dCTP, dTTP, dGTP in a total volume of 200 µl. The DNA is ethanol precipitated and further digested with XhoI. The 1.2 kb blunt end [BstXI] -XhoI fragment is separated on a 0.8% agarose gel, electroeluted and ethanol precipitated. This fragment contains the coding sequence for K$_2$ and the B-chain of t-PA. 0.2 µmoles of the 1.2 kb t-PA fragment and 0.1 µmoles of the 3 kb u-PA/vector fragment (see above) are ligated as described. Aliquots of the ligation mixture are used to transform competent *E. coli* HB101 cells. Ampicillin-resistant colonies are selected on LB agar plates containing 100 mg/l ampicillin. DNA is prepared from individual transformants and analysed by ScaI and SmaI restriction digests. A clone containing the 0.5 kb ScaI and the 1.55 kb SmaI junction fragments is selected and referred to as pCS16/Uk$_2$TPA$^B$.

Example 12: A t-PA/u-PA hybrid plasminogen activator with the second kringle of t-PA and the catalytic B-chain of u-PA (primary construct)

A hybrid plasminogen activator gene comprising the DNA sequences of the urokinase "growth factor like" (U) domain, the second kringle (K$_2$) of t-PA and the catalytic B-chain of u-PA is constructed by a method analogous to the one described in Example 11.

Construction of plasmid pCS16/UK$_2$UPA$^B$:

5 µg of plasmid pCS16/UPA are digested with BglII and NcoI (nucleotide positions 391–396 and 326–331, respectively, see FIG. 4). The sticky ends of the restriction fragments are filled in a reaction with Klenow DNA polymerase I (BRL) as described above. The 4.2 kb DNA fragment with Blunt ends is isolated on a 0.8% agarose gel in Tris-acetate buffer pH 8,2. The DNA is electroeluted and ethanol precipitated. This fragment contains the u-PA G-domain and the u-PA B-chain connected to the vector molecule.

10 µg of plasmid p31/PHO5-TPA18 (European patent application No. 143,081) are digested with AluI. A 447 bp AluI fragment containing the whole K$_2$ domain of t-PA, is isolated on a 1.5% agarose gel in Tris-borate-EDTA buffer pH 8.3. The DNA fragment is electroeluted and ethanol precipitated. 0.2 µmoles of the 447 bp fragment and 0.1 µmoles of the 4.2 kb fragment are ligated. Aliquots of the ligation mixture ace used to transform competent *E. coli* HB101 cells. Transformed cells ace selected on LB agar plates with 100 mg/l ampicillin. DNA is prepared from ampicillin resistant cells and analysed by EcoRI and ScaZ digests. A single clone showing a 551 bp EcoRI fragment and a 403 bp ScaI fragment has the AluI fragment inserted in the correct orientation. This clone is referred to as pCS16/UK$_2$UPA$^B$.

Example 13: Cloning of primary hybrid DNA constructs in M13mp18

A) Cloning of a pJDB207/PHOS-I-TPA$^A$UPA$^B$ BamHI fragment in M13mp18

1.5 µg of pJDB207/PHO5-I-TPA$^A$UPA$^B$ (cf. Example 9) obtained from a quick DNA preparation is digested with 9 U of BamHI (Boehringer) in 20 pl of 10 mM Tris·HCl pH 7.5, 6 mM MgCl$_2$, 100 mM NaCl, 6 mM mercaptoethanol at 37° C. for one hour. After adding 1 µl of RNase (Serva, 1 mg/ml), incubating for 15 min at 37° C. and phenolization, the 2.5 kb insert is isolated on a 0.8% preparative agarose gel, The DNA is extracted by electroelution and precipitated.

1 µg of M13mp18 (RF) is cut with BamHI, treated with calf intestinal alkaline phosphatase and the 7.3 kb vector fragment is isolated on a 0.7% preparative agarose gel. The DNA is electroeluted and precipitated.

100 µmoles of M13mp18 BamHI cut vector and 200 µmoles of the BamHI TPA$^A$UPA$^B$ insert are ligated in 10 µl of 50 mM Tris·HCl pH 7.5, 10 mM MgCl$_2$, 10 mM DTT, 2 mM ATP, 0.5 Ug gelatin with 400 U of T$_4$ DNA ligase for 7 hours at 15° C. After incubation at 65° C. for 10 min, 5 µl of this ligation mixture is used for transformation of *E. coli* JM101 competent cells according to the manual "M13 Cloning and sequencing handbook" published by Amersham. 36 colourless plaques are picked, and single-stranded and replicative form (RF) DNA are prepared. On analysis of RF-DNA all clones show the correct size inserts after digestion with BamHI. Correct size fragments after digestion with EcoRI and PstI indicate that the DNA inserts in all clones are in the wrong orientation (single-stranded template DNA is the non-coding strand). One of these clones is referred to as mp18/BamHI/TPA$^A$UPA$^B$ and is used for deletion mutagenesis.

B. Cloning of a pCS16/UPA$^A$TPA$^B$ KpnI-HindIII fragment in M13mp18

1.5 μg of pCS16/UPA^A TPA^B (cf. Example 10) obtained from a quick DNA preparation is digested with 12 U of KpnI in 20 μl of 10 mM Tris·HCl pH 7.5, 6 mM MgCl$_2$, 6 mM mercaptoethanol at 37° C. for one hour. After adding 1 μl of 1 M NaCl, -DNA is digested with 12 U of HindIII at 37° C. for one hour. A 1.5 kb fragment is isolated on a 0.8% preparative agarose gel. The DNA is extracted by electroelution and precipitated. 0.5 μg of M13mp18 (RF) is digested with KpnI and HindIII. The 7.3 kb vector fragment is isolated on a 0.7% preparative agarose gel. The DNA is electroeluted and precipitated.

100 pmoles of M13mp18 KpnI-HindIII cut vector and 200 fmoles of KpnI-HindIII insert are ligated in 10 pl of 50 mM Tris·HCl pH 7.5, 10 mM MgCl$_2$, 10 mM DTT, 2 mM ATP, 0.5 Ug gelatin with 400 U of T$_4$ DNA ligase for 7 hours at 15:° C. The reaction is stopped by incubation at 65° C. for 10 min. 5 pl of this ligation mixture is used for transformation of *E. coli* JM101 competent cells. Ten colourless plaques are picked, and single-stranded and replicatire form (RF) DNA are prepared. On analysis of RF-DNA, all clones show correct size inserts and correct size fragments. One of these clones is referred to as mp18/KpnI-HindIII/UPA^A T-PA^B and is used for deletion mutagenesis.

C. Cloning of a pCS16/UK$_2$TPA^B KpnI-HindIII fragment in M13mp18

1.5 μg of pCS16/UK: (cf. Example 11) obtained from a quick DNA preparation is digested with 12 U of KpnI (Boehringer) in 20 pl of 10 mM Tris-HCl pM 7.5, 6 mM MgCl$_2$, 6 mM mercaptoethanol at 37° C. for one hour.

After adding 1 μl of 1 M NaCl, DNA is digested with 12 U of HindIII at 37° C. for one hour. A 1.5 kb fragment is isolated on a 0.8% preparative agarose gel. The DNA is extracted by electroelution and precipitated.

0.5 μg of M13mp18 (RF) is digested with Kpn I and HindIII. The 7.3 kb vector fragment is isolated on a 0.7% preparative agarose gel. The DNA is electroeluted and precipitated.

100 fmoles of M13mp18 KpnI-HindIII cut vector and 200 fmoles of KpnI-HindIII insert are ligated in 10 μl of 50 mM Tris·HCl pH 7.5, 10 mM MgCl$_2$, 10 mM DTT, 2 mM ATP, 0.5 μg gelatin with 400 U of T$_4$ DNA ligase for 7 hours at 15° C. The reaction is stopped by incubation at 65° C. for 10 min. 5 μl of this ligation mixture is used for transformation of *E. coli* JM101 competent cells. Seven colourless plaques are picked, and single stranded and replicatire form (RF) DNA are prepared. On analysis of RF-DNA, all clones show correct size inserts and correct size fragments. One of these clones is referred to as mp18/KpnI-HindIII/UK$_2$TPA^B and is used for deletion mutagenesis.

D. Cloning of a pCS16/UK$_2$UPA^B KpnI-HindIII fragment in M13mp18

1.5 μg of pCS16/UK$_2$UPA^B (cf. Example 12) obtained from a quick DNA preparation is digested with 12 U of KpnI in 20 μl of 10 mM Tris·HCl pH 7.5, 6 mM MgCl$_2$, 6 mM mercaptoethanol at 37° C. for one hour. After adding 1 μl of 1 M NaCl, the DNA is digested with t$_2$ U of HindIII at 37° C. for one hour. A 1.7 kb fragment is isolated on a 0.8% preparative agarose gel. The DNA is extracted by electroelution and precipitated.

0.5 μg of M13mp18 (RF) is digested with KpnI and HindIII. The 7.3 kb vector fragment is isolated on a 0.7% preparative agarose gel. The DNA is electroeluted and precipitated.

100 fmoles of M1Bmp18 KpnI-MindIII cut vector and 200 fmoles of KpnI-HindIII insert are ligated in 10 μl of 50 mM Tris·HCl pH 7.5, 10 mM MgCl$_2$, 10 mM DTT, 2 mM ATP, 0.5 μg gelatin with 400 U of T$_4$ DNA ligase for 7 hours at 15° C. The reaction is stopped by incubation at 65° C. for 10 min. 5 μl of this ligation mixture is used for transformation of *E. coli* JM101 competent cells. Ten colourless plaques are picked, and single-stranded and replicatire form (RF) DNA are prepared. On analysis of RF-DNA, all clones show correct size inserts and correct size fragments. One of these clones is referred to as mp18/KpnI-HindIII/UK$_2$UPA^B and is used for deletion mutagenesis.

Example 14: Deletion mutagenesis of primary hybrid DNA constructs

A) General protocol for deletion mutagenesis a) Physphorylation of mutagenic primer:

For mutagenesis 200 μmoles of the mutagenic primer are phosphorylated in 20 μl of 50 mM Tris-HCl pH 7.5, 10 mM MgCl$_2$, 5 mM DTT, 0.1 mM spermidine, 0.1 mM EDTA containing 1 μl of 10 mM AIP using 8 U of T$_4$ polynucleotide kinase (Boehringer, 8 U/μl). After incubation at 27° C. for one hour, the reaction is stopped by heating at 65° C. for 10 min. For hybridization screening, 20 μmoles of mutagenic primer are phosphorylated as above using 30 MCi μCi γ$^{32}$P-ATP (3000 Ci/mmole; Amersham International) at the only source of ATP. The primer is diluted with 3.5 ml 6×SSC and used directly as a probe.

b) Annealing of mutagnic primer and universal sequencing primer to single-stranded template 0.2 μmole of single-stranded template is incubated with 20 μmoles of phosphorylated mutagenic oligodeoxyribonucleotide primer (10 μmoles/μl) and 10 μmoles of universal M13 sequencing primer in 10 μl of 20 mM Tris·HCl pH 7.5, 10 mM MgCl$_2$, 50 mM NaCl, 1 mM DTT at 95° C. for 5 min. The solution is allowed slowly to cool to room temperature over a period of 30 min.

c) Extension-ligation reaction

To the above annealed mixture is added 10 μl of enzyme-dNTP (dATP, dGTP, dTTP, dCTP) solution containing 1 μl of buffer [0.2 M Tris·HCl pH 7.5, 0.1 MgCl$_2$, 0.1 M DTT], 4 pl 12.5 mM dNTP mixture, 1 μl 10 mM ATP, 0.5 μl T$_4$ DNA ligase (Biolabs, 400 U/μl), 0.67 μl of Klenow DNA polymerase (BRL, 2.99 U/μl). The mixture is incubated at 15° C. for one hour and then incubated at 8°–9° C. for 16 hours. The reaction is stopped by incubating at 65° C. for 10 min.

d) Transformation of ligation mixture

The ligation mixture is diluted 1:20 and 1:200 with TE, 1 μl and 5 μl of each of these diluted solutions are used to transform 0.2 ml of a repair-minus strain of *E. coli* BMH 71–1Smuts [BMH71–18Δ((lac-proAB), thi, supE, F'laci$^q$, ZΔM15, proA$^+$B$^+$] competent cells. Construction of *E. coli* BMH71–18mutS (BMH71–18, mut S215::Tnio) is described by Kramer et al. [Cell 38, 879–887 (1984)]. After transfection, lawn cells are provided by repair+strain of *E. coli* JM101 in order to minimize the exposure of the phage to the mutator phenotype of the repair-minus strains [P. Carter, H. Bedouelle and G. Winter, Nucl. Acids Res. 13, 4431–4443 (1985)].

e) Screening of phages 100 plaques resulting from the transfected DNA are tooth picked on to YT plates and grown up as colonies of infected bacteria for 15–18 hours. Colony blotting was adapted from Grunstein and Hogness [Proc. Natl. Acad. Sci. USA 72, 3961–3965 (1985)]. A nitrocellulose filter (Millipore S. A., Cat. No. HAWP 090, pore size 0.45 µm) is placed on the colony plate for 10 min at room temperature. Filters are denatured with 0.5 N NaOH, neutralized with 1 M Tris.HCl pH 7.5 and then treated with a high-salt solution (0.5 M Tris·HCl pH 7.5+1.5 M NaCl). The filters are baked in vacuo for 30 minutes at 80° C., prehybridized in 100 ml of 10×Denhardt's solution (D. T. Denhardt, Biochem. Biophys. Res. Commun. 23, 641–646), 6×SSC and 0.2% SDS in a sealable plastic bag for 15 minutes.

For hybridization screening, prehybridized filters are washed in 50 ml of 6×SSC for 1 minute and then hybridized in 3.5 ml of probe containing $^{32}$P-labelled mutagenic primer for 30 minutes. Hybridized filters are washed three times in 100 ml 6×SSC at room temperature for a total of 2 minutes and then autoradiographed. Good discrimination between wild-type and mutant phages are obtained by a brief wash (5 min) at 60° C. in 100 ml 0.1×SSC+0.1% SDS.

f) Confirmation of deletion mutation in positive clones obtained from hybridization The phages from the positive clones are tooth picked into 1 ml 2×YT, heated at 70° C. for 20 minutes to kill the bacteria, and then 100 µl of this phage suspension is inoculated into 1.5 ml of a freshly growing E. coli JM101 culture (OD$_{600}$∝0.45). The cultures are vigorously shaken (300 rpm) at 37° C. for 4 hours. Phage-stock and replicarive form DNA from the positive clones are prepared [J. Messing, Methods in Enzymology, 101, 21–78 (1983)].

DNA from the mutants (after deletion mutagenesis) is analysed with suitable restriction enzymes and compared with the restriction fragments of wild type (before deletion mutagenesis) DNA. After confirmation by restriction analysis, DNA from one correct mutant is plaque purified. Mutations are further verified by restriction analysis and sequencing using the chain-terminator method [F. Sanger, S. Niclen and A. R. Coulson, Proc. Natl. Acad. Sci, USA 7–4, 5463–5467 (1977)].

Figure 23:
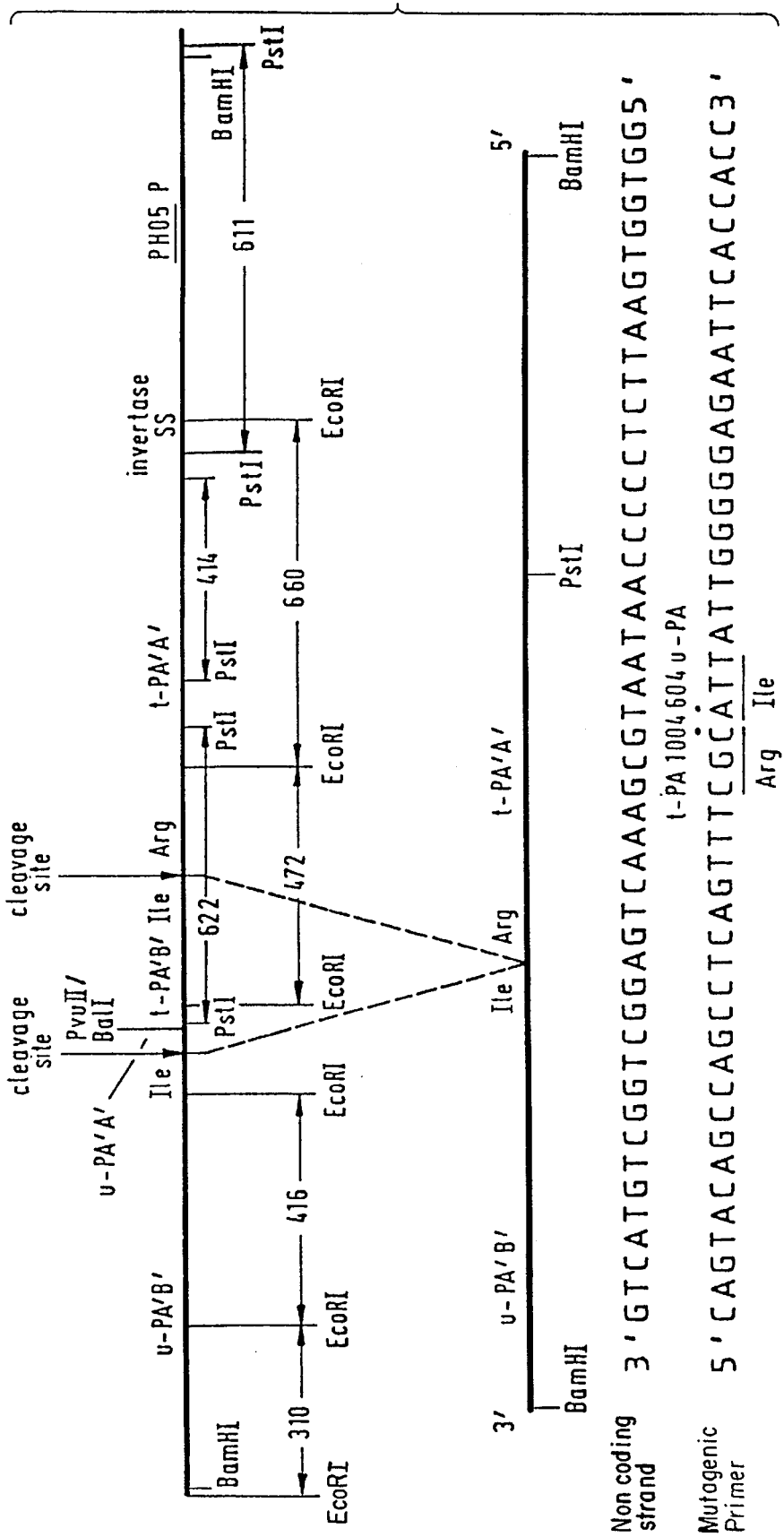
FIGS. 23–26 schematically illustrate the techniques used to convert primary hybrid PA constructs including A-chain domains and the catalytic B-chain region of u-PA or t-PA into the final constructs in which the junction of the domains is at the activation site and/or at the natural exon-intron junction sites.

B) Deletion mutagenesis on mp18/BamHI/TPA$^A$UPA$^B$ (see FIG. 23)

Deletion mutagenesis is carried out as described in the general protocol. Positive clones obtained from hybridization are confirmed by restriction analysis. 333 bp are removed by deletion mutagenesis from the BamHI fragment. Restriction analysis with BamHI confirms the 2150 bp fragment. Further restriction analysis with EcoRI yields 660, 416, 287,230 bp fragments on the mutants instead of 660, 472,416 and 287 fragments seen in the wild type. Analysis with PstI shows two fragments, 611 and 414 bp in size for the mutants. Wild type DffA shows three fragments of 622, 611 and 414 bps. One mutant clone having the correct structure is referred to as mp18/BamHI/HOTPA$^A$UPA$^B$.

The DNA sequence at the junction between the t-PA A chain and u-PA B chain is verified by the chain terminator sequencing method having a sequencing primer of the sequence

5'CAGAGCCCCCCCGGTGC 3'.

This primer is complementary to the coding strand of u-PA (682–666).

Figure 24:
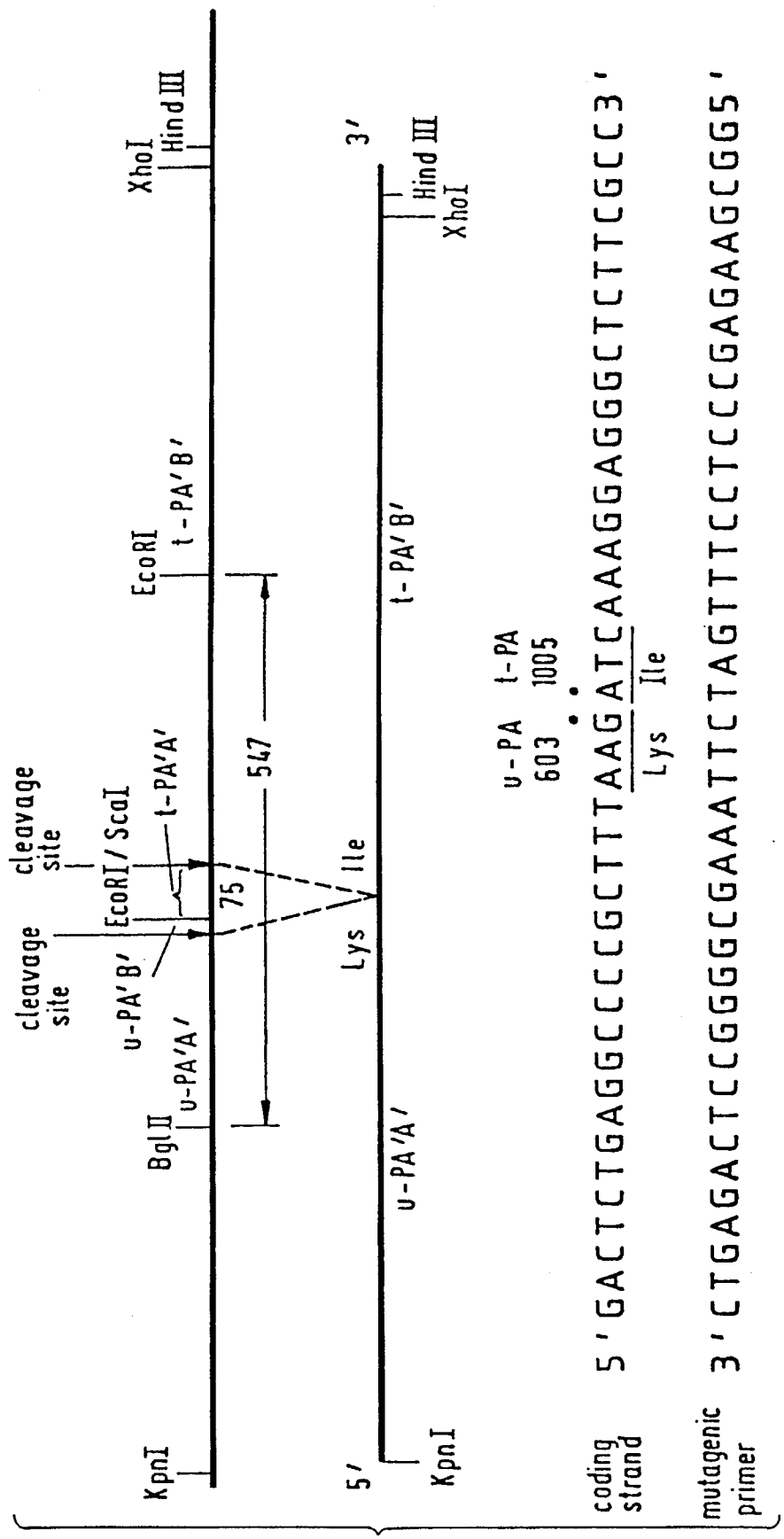

C) Deletion mutagenesis on mp18/KpnITHindIII/UPA$^A$T-PA$^B$ (see FIG. 24)

Deletion mutagenesis is carried out as described in the general protocol. Positive clones obtained from hybridization are confirmed by restriction analysis with PstI. In the mutants a 467 bp band is observed compared to the wild type which yields a 544 bp fragment. One mutant clone having the correct structure is referred to as mp18/KpnI-HindIII/ MOUPA$^A$TPA$^B$. The deletion is verified by the chain-terminator sequencing method using a sequencing primer of the sequence

5'CAAAGATGGCAGCCTGC 3'

This primer is complementary to the coding strand of t-PA (1062–1046).

Figure 25:
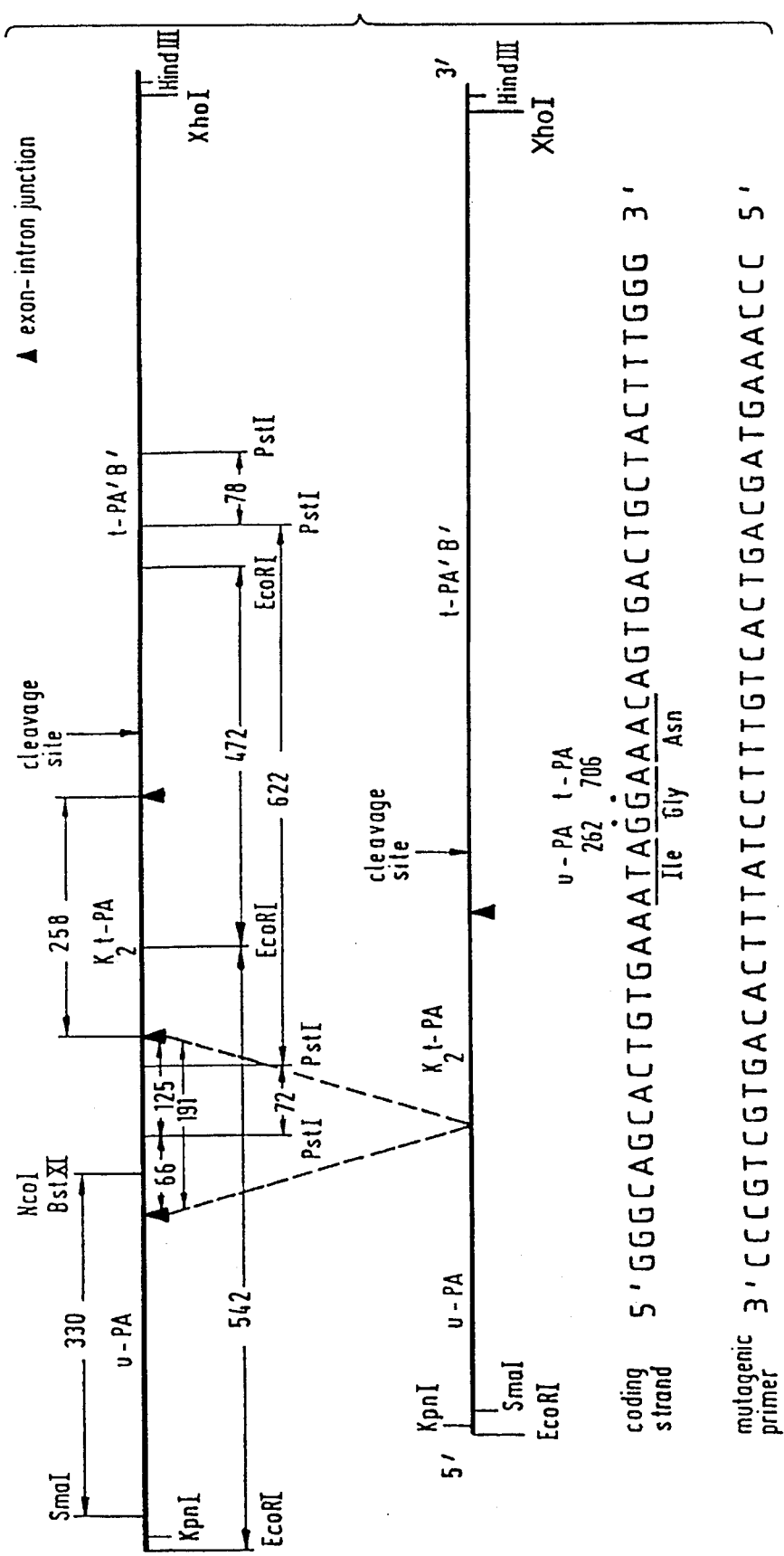

D. Deletion mutagenesis on mp18/KnpI-HindIII/UK$_2$TPA$^B$ (see FIG. 25)

Deletion mutagenesis is carried out as described in the general protocol. Positive clones obtained from hybridization are confirmed by restriction analysis with KpnI-HindIII, Eco RI and PstI. The fragments obtained are

| KpnI-HindIII wild type | mutant | EcoRI wild type | mutant | PstI wild type | mutant |
|---|---|---|---|---|---|
| 1475 bp | 1284 bp | 542 bp 472 bp | 351 bp 472 bp | 622 bp | no 622 bp band |

Correct size insert and correct size fragments are observed for mutants. One mutant clone having the correct structure is referred to as mp18/KpnI-HindIII/MOUK$_2$TPA$^B$. The deletion is verified by the chain-terminator sequencing method using a sequencing primer of the sequence

5' CCCAGTGCCTGGGCACTGGGGTTCTGTGCTGTG 3'.

This primer is complementary to the coding strand of t-PA (853–821).

Figure 26:
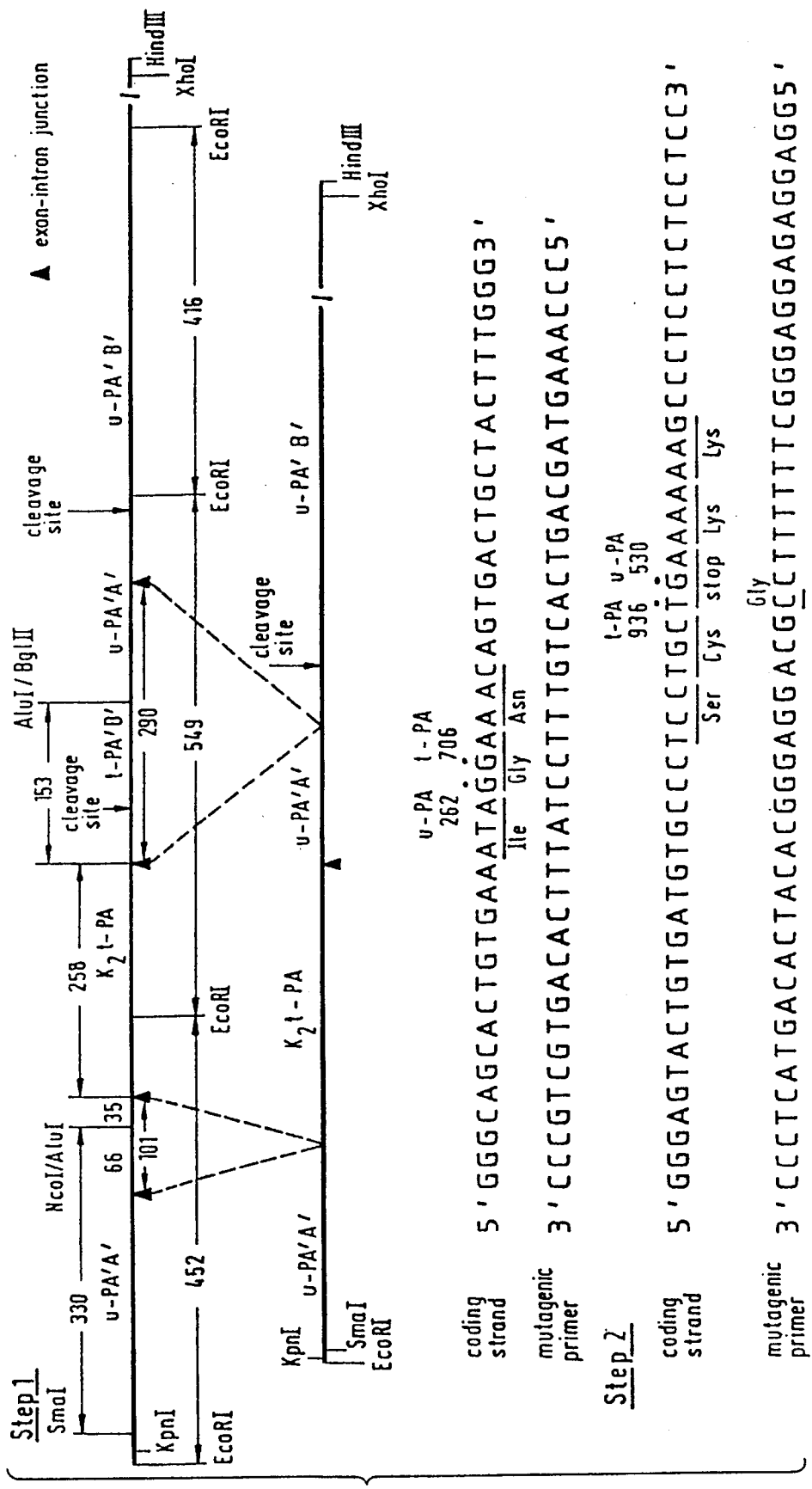
Figure 27A:
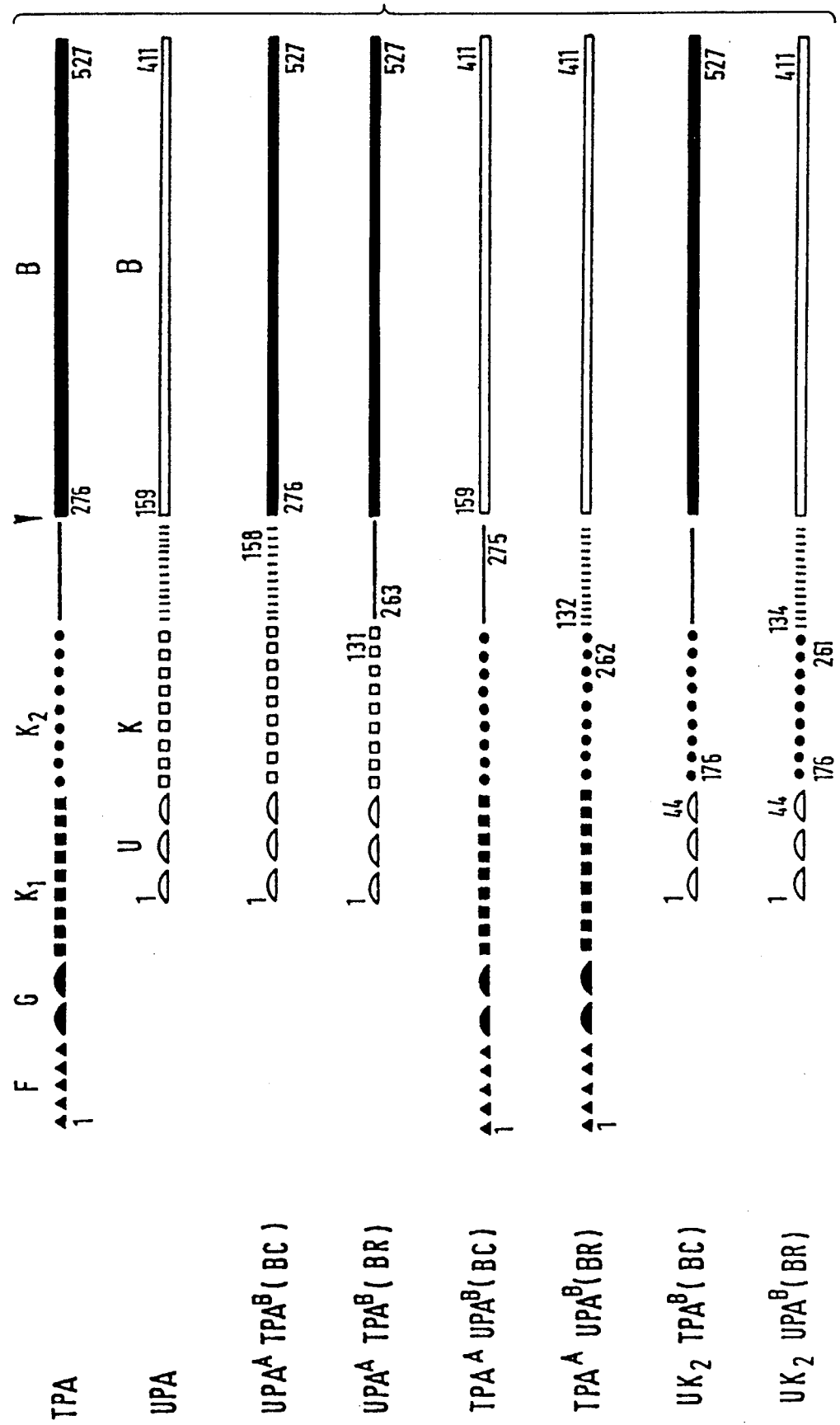
FIGS. 27A–C is a compilation of hybrid PAs and mutant hybrid PAs as exemplified in the Experimental Part.
Figure 27B:
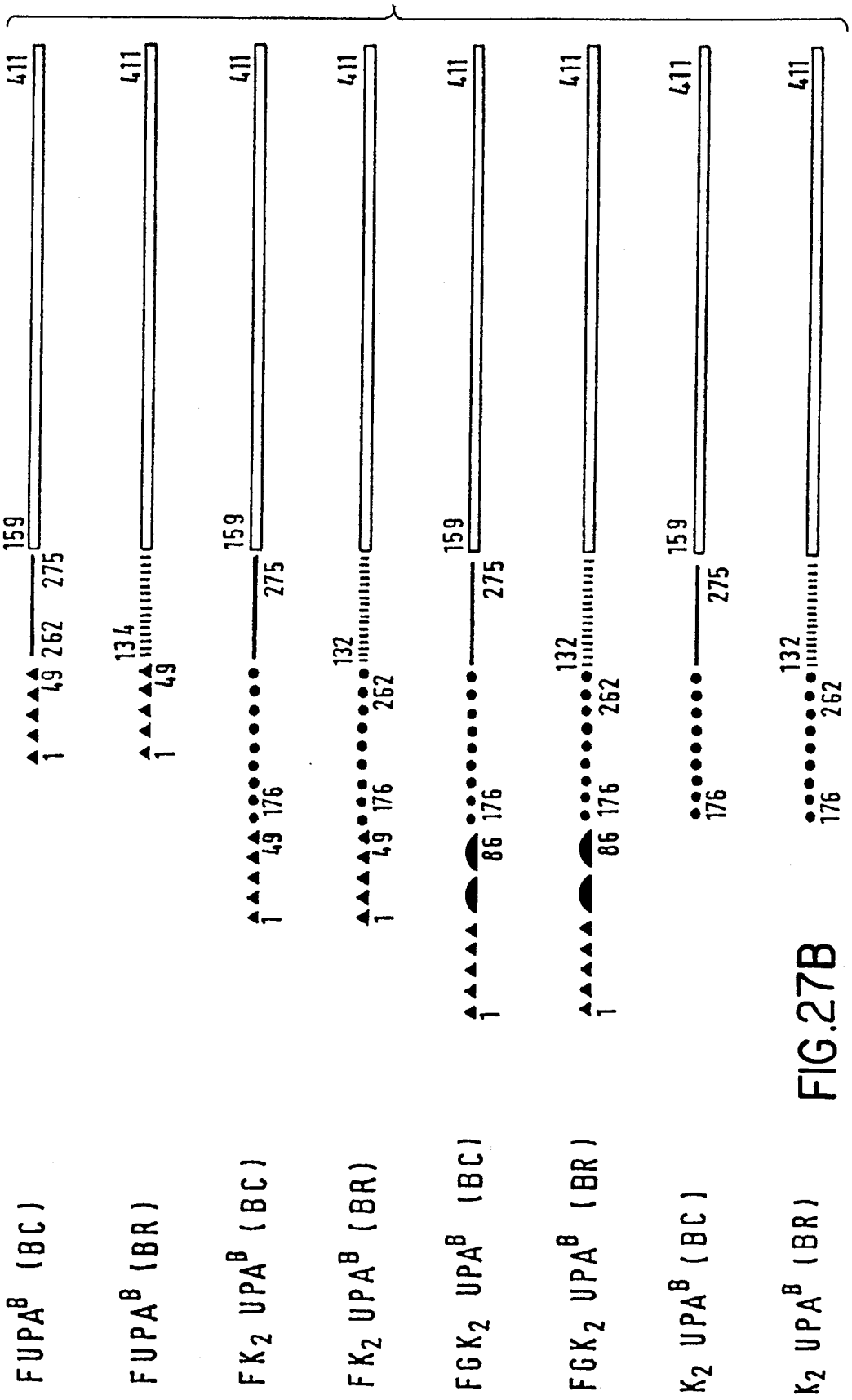
Figure 27C:
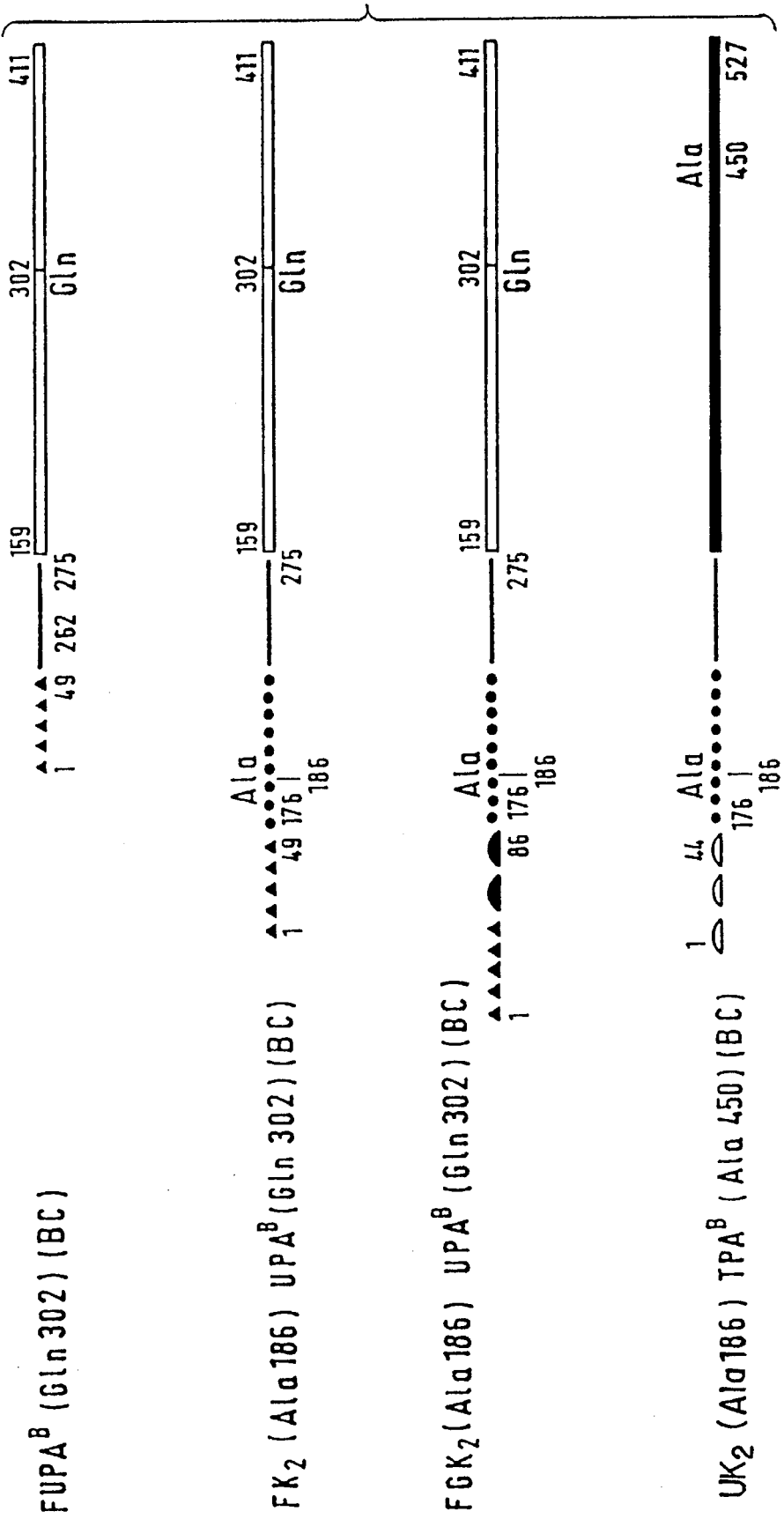

E) Deletion mutagenesis on mp18/KpnI-HindIII/UK$_2$UPA$^B$ (see FIG. 26)

Two separate deletion mutations are involved in the construction of UK$_2$UPA$^B$:

First deletion mutagenesis is carried out as described in the general protocol. Positive clones obtained from hybridization are confirmed by restriction analysis with EcoRI. In the mutants 549, 416, 351 bp bands are observed compared to the wild type which yields 549, 452 and 416 bp fragments. One mutant clone having the correct structure is referred to as mp18/KpnI-HindIII/MOUK$_2$UPA$^B$-1. The deletion is verified by the chain-terminator sequencing method using a sequencing primer of the sequence

5' CCCAGTGCCTGGGCACTGGGGTTCTGTGCTGTG 3'.

The primer is complementary to the coding strand of t-PA (853–882)

In the second step of deletion mutagenesis, a deletion is made simultaneously with the introduction of a point mutation. Deletion mutagenesis is carried out as described in the general protocol. Positive clones obtained from hybridization are confirmed by restriction analysis with EcoRI. In the mutants, 416, 351,259 bp bands are observed compared to the wild type which yields 549,416 and 351 bp fragments. One mutant clone having the correct structure is referred to as mp18/KpnI-HindIII/MOUK$_2$UPA , The deletion is verified by the chain-terminator sequencing method using a sequence primer of the sequence

5' CAGAGCCCCCCCGGTGC 3'.

The primer is complementary to the coding strand of u-PA (682–666).

Example 15: Cloning of the hybrid t-PA/u-PA cDNA constructs into yeast expression vector pJDB207

A) Cloning of the TPA$^A$UPA$^B$ hybrid gene into pJDB207

RF-DNA is prepared for mp18/BamHI/MOTPA$^A$UPA$^B$ by the quick DNA isolation procedure [D. S. Holmes and M. Quingley, Anal. BiocheR. 114, 192–197 (1981)].

RF-DNA ($\propto$1.5 μg) is digested with 9 U of BaRHI in 20 μl of 10 mM Tris·HCl pH 7.5, 6 mM MgCl$_2$, 100 mM NaCl, 6 mM Rercaptoethanol for one hour at 37° C. After adding 1 μl of RNase (1μg/ml) and incubating for 10 minutes at 37° C., the 2.1 kb insert is isolated on a 0.7% preparative agarose gel. The DNA insert is extracted by electroelution and precipitated in ethanol.

1.5 μg of pJDB207/PHO5-I-TPA$^A$APA$^B$ is cut with BaRHI, treated with calf intestinal alkaline phosphatase and the 6.7 kb vector is isolated. After electroelution the vector DNA is precipitated.

100 fmoles of pJDB207/PHOS-I-TPA$^A$UPA$^B$ BamHI cut vector, 200 fmoles of TPA$^A$UPA$^B$ insert are ligated in 10 μl of 50 mM Tris·HCl pH 7.5, 10 mM MgCl$_2$, 10 mM DTT, 2 mM ATP, 0.5 μg gelatin with 400 U of T$_4$ DNA ligase for 8 hours at 15° C. The reaction is stopped by incubation at 65° C. for 10 minutes. 5 μl of this ligation mixture is used for transformation of E. coli HB101 Ca cells [M. Dagert and S. D. Ehrlich, Gene 6, 23–28 (1979)]. 12 amp$^R$ colonies are picked and DNA is prepared by the quick isolation procedure. On analysis of DNA 5 clones show both correct size inserts and correct orientation. One clone is grown in 100 ml LB medium containing 100 mg/ml of ampicillin. Plasmid DNA is isolated and is referred to as pJDB207/PHOS-I-MOTPA$^A$UPA$^B$.

B) Cloning of the MOUPA$^A$TPA$^B$, MOUK$_2$TPA$^B$ and MOUK$_2$UPA$^B$ gene inserts into plasmid pCS16

RF-DNA is prepared for mp18/KpnI-HindIII/MOUPA$^A$TPA$^B$, mp18/KpnI-HindIII/MOUK$_2$TPA$^B$, mp18/KpnI-HindIII/MOUK$_2$UPA$^B$ by the quick DNA isolation procedure.

The three RF-DNAs ($\propto$1.5 μg) are each digested with 12 U of KpnI and 12 U of HindIII in 20 μl of 10 mM Tris·HCl pH 7.5, 6 mM MgCl$_2$, 6 mM mercaptoethanol for one hour at 37° C. 1 μl of 1 M NaCl is added and the DNAs further digested with 12 U of HindIII. After adding 1 μl of RNase (1 mg/ml) and incubating for 10 min at 37° C., the 1.4 kb inserts are each isolated on a 0.8% preparative agarose gel. The DNA inserts are extracted by electroelution and precipitated in ethanol.

Three μg of pCS16/UPA is digested with KpnI and Hind III and the 2.7 kb vector fragment is isolated. After electroelution, the vector DNA is precipitated in ethanol.

100 fmoles of pCS16 KpnI-HindIII cut vector, 200 fmoles of KpnI-HindIII cut insert fragments are ligated in 10 μl of 50 mM Tris·HCl pH 7.5, 10 mM MgCl$_2$, 10 mM DTT, 2 mM ATP, 0.5 Ug gelatin with 400 U of T$_4$ DNA ligase for 8 hours at 15° C. The reaction is stopped by incubation at 65° C. for 10 minutes, 5 μl of this ligation mixture is used for transformation of E. coli HB101 Ca$^{2+}$ cells.

Six amp$^R$ colonies are picked from each of the three ligations. DNA is prepared by the quick isolation procedure. On analysis of DNA with KpnI-HindIII correct size insert bands are observed. One clone from each of the three ligations is grown in 100 ml LB medium containing 100 μg/ml of ampicillin. Plasmid DNAs derived from mp18/KpnI-HindIII/MOUPA$^A$TpA$^B$, mp18/KpnI-HindIII/MOUK$_2$TPA$^B$ and mp18/KpnI-HindIII/MOUK$_2$UpA$^B$ are isolated and are referred to as pCS16/MOUPA$^A$TPA$^B$, pCS16/MOUK$_2$TpA$^B$ and pCS16/MOUK$_2$UPA$^B$, respectively.

C) Cloning of the MOUPA$^A$TPA$^B$, MOUK$_2$TPA$^B$ and MOUK$_2$UPA$^B$ gene inserts into pJDB207

Five μg of pJDB207/PHOS-I-UPA is digested with 15 U of ScaI and 15 U of XhoI (Boehringer) in 50 μl of 10 mM Tris·HCl pH 7.5, 6 mM MgCl$_2$, 150 mM NaCl, 6 mM mercaptoethanol for one hour at 37° C. After adding 1 μl of RNase (1 mg/ml), the 6.7 kb vector fragment is isolated. After electroelution, the vector DNA is precipitated.

Fifteen μg of each of pCS16/MOUPA$^A$TPA$^B$, pCS16/MOUK$_2$TPA$^B$ pCS16/MOUN$_2$UPA$^B$ are incubated at 37° C. for one hour with 30 U of XhoI in 200 of 10 mM Tris·HCl pH 8, 6 mM MgCl$_2$, 150 mM NaCl, 6 mM mercaptoethanol, extracted with an equal volume of phenol-chloroform and precipitated in ethanol. The precipitated XhoI cut pCS16/MOUPA$^A$TPA$^B$ pCS16/MOUK$_2$TPA and B pCS16/MOUK$_2$ DNAs are each resuspended in 150 μl of 10 mM Tris·HCl pH 7.5, 6 mM MgCl$_2$, 150 mM NaCl, 6 mM mercaptoethanol, 1.5 μg ethidium bromide, incubated at 37° C. for 40 minutes with 12 U of ScaI (partial digest), and extracted with an equal volume of phenol, followed by an equal volume of chloroform-isoamyl alcohol (50:1). The 1.2 kb fragments are each isolated on a 1% preparative agarose gel. The DNAs are extracted by electroelution and precipitated.

100 fmoles of pJDB207/PHO5-I-UPA ScaI-XhoI cut vector and 200 fmoles of Xho-ScaI cut pCS16/MOUPA$^A$TPA$^B$ PCS16/MOUK$_2$TPA$^B$ or pCS16/MOUK$_2$UPA$^B$ 1.2 kb inserts, respectively, are ligated in 10 μl of 50 mM Iris.HCl pH 7.5, 10 mM MgCl$_2$, 10 mM DTT, 2 mM ATP, 0.5 μg gelatin with 400 U of T$_4$ DNA ligase for 16 hours at 15° C. The reaction is stopped by incubation at 65° C. for 10 minutes. 5 μl of this ligation mixture is used for transformation of E. coli HB101 Ca$^{2+}$ cells.

Six amp$^R$ colonies are picked from each of the three ligations. DNA is prepared by the quick isolation procedure. Restriction analysis of DNAs show correct size insert bands. One clone from each of the three ligations is grown in 100 ml LB medium containing 100 μg/ml of ampicillin. Plasmid DNAs derived from pCS16/MOUPA$^A$TPA$^B$, pCS16/MOUK$_2$TpA$^B$, pCS16/MOUK$_2$UPA$^B$ are referred to as pJDB207/pHO5-I-MOUpAATpA$^B$, pJDB207/PHO5-I-MOUK$_2$TPA$^B$ and pJDB207/pHO5-I-MOUK$_2$UPA$^B$, respectively.

Example 16: Transformation of *Saccharomyces cerevisiae* GRF18 and preparation of yeast cell extracts The plasmids pJDB207/PHOS-I-MOTPA$^A$UPA$^B$, pJDB207/PHOS-I-MOUPA$^A$TPA$^B$, pJDB207/PHO5-I-MOUK$_2$TPA$^B$ and pJDB207/PHO5-I-MOUK$_2$UPA$^B$ are each introduced into *Saccharomyces cerevisiae* strain GRF18 using the transformation protocol described by Hinnen et al. [Proc. Natl. Acad. Sci. USA 75, 1929 (1978)]. Five μg each of plasmid DNA are added to 100 μl of a spheroplast suspension and the mixture is treated with polyethylene glycol. The spheroplasts are mixed with 10 ml regeneration agar and plated onto yeast minimal medium plates without leucine. After incubation for 3 days at 30° C. about 200 transformed cells are obtained.

One colony from each of the yeast transformations is picked. The different colonies are referred to as

| | |
|---|---|
| *Saccharomyces cerevisiae* | GRF18/pJDB207/PHO5-I-MOTP$^A$UPA$^B$ |
| *Saccharomyces cerevisiae* | GRF18/pJDB207/PHO5-I-MOUP$^A$TPA$^B$ |
| *Saccharomyces cerevisiae* | GRF18/pJDB207/PHO5-I-MOUK$_2$TPA$^B$ |
| *Saccharomyces cerevisiae* | GRF18/pJDB207/PHO5-I-MOUK$_2$UPA$^B$ |

Yeast cells are grown at 30° C. in 20 ml of HE-17 medium (8.4 g Yeast Nitrogen Base (Difco), 10 g L-asparagine (Sigma), 1 g L-histidine (Sigma), 40 ml 50% glucose per 1 liter solution) in a 50 ml Erlenmeyer flask with shaking for 24 hours until a density of 8–10×10⁷ cells/ml is reached. The cells are centrifuged, resuspended in 10 ml 0.9% NaCl. Two ml of the resuspended cells are used to inoculate 50 ml low-P minimal medium (as described in European Patent Application No. 143081) to which 10 g/l L-asparagine (Sigma), and 10 g/l L-histidine (Sigma), are added in 250 ml Erlenmeyer flasks. Incubation is at 30° C. at 250 rpm.

Cells from 10 ml of low $P_i$ minimal medium are collected after 48 hours by centrifugation at 3000 rpm for 10 minutes in Falcon 2070 tubes. The cells are washed once with 10 ml low $P_i$ medium and centrifuged. The cell pellet is suspended in lysis buffer [66 mM potassium phosphate pH 7.4, 4 mM Zwittergent (Calbiochem.)]. To the cell suspension are added 8 g of glass beads (0.5–0.75 mm in diameter) and a small glass rod and the suspension is shaken on a Vortex Hixer (Scientific Instruments Inc., USA) at fullspeed for 4×2 min with intervals of 2 min on ice. More than 90% of the cells are broken by this procedure. Cell debris and glass beads are sedimented by centrifugation for 5 min at 3000 rpm at 4° C. The supernatant is used for the determination of PA activity and for the purification and isolation of PA.

Example 17: Insertion of hybrid PA coding sequences into mammalian cell expression vector A) Insertion of a UPA$^A$TPA$^B$ 'perfect' hybrid coding sequence RF DNA of mp18/KpnI-HindIII/MOUPA$^A$TPA$^B$ is cut at the SmaI site located just upstream of the beginning of the coding sequence and ligated to a SacI linker (CGAGCTCG). Subsequently, the plasmid is cut with SacI, which cuts at the position of the ligated linkers and at the natural SacI site in the t-PA-derived portion of the hybrid PA coding sequence. The smaller of the two resulting fragments is purified via an agarose gel and ligated to SacI-cut pCGA44 (see Example 4), transformed into $E.$ $coli$ HB101 and DNA from candidate clones is tested with EcoRI. A clone with the expected restriction pattern is referred to as pCGC1/UPA$^A$TPA$^B$.

B) Insertion of UK$_2$TPA$^B$ hybrid coding sequence

RF DNA of mp18/KpnI-HindIII/MOUK$_2$TPA$^B$ is cut at the SmaI site located just upstream of the begin of the coding sequence and ligated to SacI as above. After cutting with SacI the resulting small fragment is cloned into SacI-cut pCGA44 as described above and a clone with the expected restriction pattern is referred to as pCGC2/UK$_2$TPA$^B$.

C) Insertion of a UK$_2$UPA$^B$ hybrid coding sequence

RF DNA of mp18/KpnI-HindIII/MOUK$_2$UPA$^B$ is cut at the SmaI site upstream of the u-PA coding sequence and at the XhoI site downstream of the coding sequence (in the vector DNA), The sticky end of the DNA fragment is filled in using $E.$ $coli$ DNA polymerase I (cf. Example 5D). SacI linkers are ligated onto the blunt ends, the DNA is cut with SacI, the smaller of the two resulting fragments is purified via an agarose gel and cloned into SacI-cut pCGA44. A clone with the expected EcoRI restriction pattern is referred to as pCGC3/UK$_2$UPA$^B$.

D) Insertion of a TPA$^A$UPA$^B$ 'perfect' coding sequence

Step 1: RF DNA of mp18/BamHI/MOTPA$^A$UPA$^B$ is cut with BamHI and the smaller (≈2.1 kb) fragment is cloned into BamHI cut pJDB207/PH05-I-TPA$^A$UPA$^B$ (cf. Example 9) vector. Correct orientation is chosen by digestion with HindIII and one correct plasmid is termed pJDB207/PH05-I-MOTPA$^A$UPA$^B$.

Step 2: A ≈600 bp SacI-NarI fragment from ptNC·UC (cf. Example 3) and a ≈1350 bp NarI-XhoI fragment from pJDB207/PH05-I-MOTPA$^A$UPA$^B$ is isolated and cloned into SacI-XhoI cut pCS16 (cf. Example 7) vector. The ≈1.9 kb insert is confirmed by digestion with SacI-XhoI and EcoRI. One correct plasmid Is termed pCS16/MOTPA$^A$U-PA$^B$.

Step 3: Plasmid pCS16/MOTPA$^A$UPA$^B$ is cut at the XhoI site located down-stream of the u-PA coding sequence and the sticky ends filled in using $E.$ $coli$ DNA polymerase I. SacI linkers are ligated onto the blunt ends and the DNA is cut with SacI. The smaller of the two fragments is purified via an agarose gel and cloned into SacI-cut pBR4a (cf. Example 5) vector fragment. Correct orientation and correct size inserts are confirmed by digestion with BamHI and SacI, respectively. One correct plasmid is designated pCGC4a/TPA$^A$APA$^B$.

Example 18: Construction of further hybrid PA coding sequences and insertion thereof into mammalian cell expression vector A) Cloning of a pCGC4a/TPA$^A$UPA$^B$ fragment in M13mpI·8 3 µg of pCGC4a/TPA$^A$UPA$^B$ (cf. Example 17) is digested with 12 U of SacI (Boehringer) in 20 µl of 10 mM Tris-HCl pH 7.5, 6 mM MgCl$_2$, 6 mM mercaptoethanol at 37° C. for one hour. A ≈1.9 kb fragment is isolated on a 0.7% preparative agarose gel. The DNA is extracted by electroelution and precipitated.

0.5 µg of M13mp18 (RF) is digested with SacI. The 7.3 kb vector fragment is isolated on a 0.7% preparative agarose gel. The DNA is electroeluted and precipitated.

100 fmoles of M13mp18 SacI cut vector and 200 fmoles of SacI insert are agitated in 10 µl of 50 mM Tris-HCl pH 7.5, 10 mM MgCl$_2$, 10 mM DTT, 2 mM ATP, 0.5 µg gelatin with 400 U of T$_4$ DNA ligase for 7 hours at 15° C. The reaction is stopped by incubation at 65° C. for 10 min. 5 µl of this ligation mixture is used for transformation of $E.$ $coli$ JM101 competent cells. Six colourless plaques are picked, and single stranded and replicarive form (RF) DNA are prepared. On analysis of RF-DNA, four clones show correct size inserts and correct orientation. One of these clones is referred to as mp18/SacI/TPA$^A$UPA$^B$ (BC).

B) Cloning of a pBR4a SacI fragment in M13MP18

A pBR4a (cf, Example 5) SacI fragment is cloned in M13mp18. One of the clones which has a correct size insert and a correct orientation is referred to as mp18/SacI/TPA$^A$U-PA$^B$(BR)$^B$.

C) Deletion MutaRenesis on TPA-UFA hybrid constructs

1) Construction of FUPA$^B$(BC) [tpA(1–9)-tPA(262–275)-uPA(159–411)]

Deletion mutagenesis is carried out as described in the general protocol (cf. Example 14) on mp18/SacI/TPA$^A$UP-A$^B$(BC). Positive clones obtained from hybridization are confirmed by restriction analysis with SacI. In the mutants a ≈1200 bp band is observed compared to the wild type which yields a ≈1900 bp fragment. Mutants are further confirmed by EcoRI digest. One mutant clone having the correct structure is referred to as mp18/SacI/FGK$_2$UPA$^B$(BC). The deletion is verified by the chain terminator sequencing method using a sequencing primer of the sequence

5' CAGAGCCCCCCCGGTGC 3'.

This primer is complementary to the coding strand of u-PA(666–682).

2) Construction of FGK$_2$ UPA$^B$(BC) [ie. tPA(1–86)-tPA(176–275)-uPA(159–411)]

Deletion mutagenesis is carried out as described in the general protocol [cf. Example 14) on mp18/SacI/TPA$^A$A-PAB(BC). Positive clones obtained from hybridization are confirmed by restriction analysis with SacI. In the mutants a ∝1580 bp band is observed compared to the wild type which yields a ∝1900 bp fragment. Mutants are further confirmed by EcoRI digest. One mutant clone having the

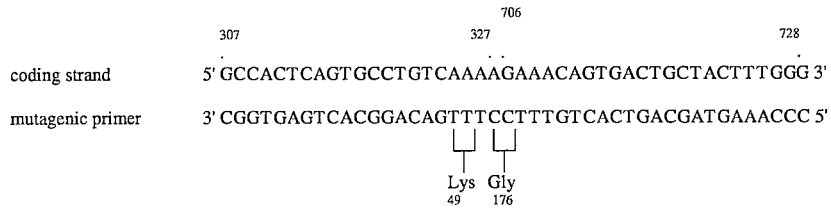

correct structure is referred to as mp18/SacI/FGK$_2$UPA$^B$(BC). The deletion is verified by the chain terminator sequencing method using a sequencing primer of the sequence

5' CCCAGTGCCTGGGCATTGGGGTTCTGTGCTGTG 3'.

This primer is complementary to the coding strand of t-PA(853–821) with a mismatch at position 838 (t-PA).

3) Construction of K$_2$UPA$^B$(BC) [ie. tPA(1–3)-tPA(176–275)-uPA(159–411)]

Step 1: Plasmid pCGC4a/TPA$^A$UPA$^B$ (cf. Example 17 D) is cut with SacI and the smaller (∝1.9 kb) fragment is subcloned into SacI cut, phosphatase treated RF DNA of M13mp18. Correct orientation is chosen by digestion with EcoRI and one correct replicative form is termed mp18/SacI/TPA$^A$UPA$^B$(BC) (cf. Example 18A).

Step 2: Deletion mutagenesis is carried out as described in the general protocol (cf. Example 14) on mp18/SacI/TPA$^A$UPA$^B$(BC) using a mutagenic primer which is complementary to the coding strand of t-PA (728–706) and t-PA (189–171).

Positive clones obtained from hybridization are confirmed by restriction analysis. In the mutants a 1.4 kb band is observed compared to the wild type which yields a 1.9 kb fragment. Mutants are further confirmed by EcoRI digest. One mutant clone having the correct structure is referred to as mp18/SacI/K$_2$UPA$^B$(BC). The deletion is verified by the chain terminator sequencing method using a sequencing primer of the sequence

5' CCCAGTGCCTGGGCATTGGGGTTCTGTGCTGTG 3'

This primer is complementary to the coding strand of t-PA (853–821) with a mismatch at position 838 (t-PA).

4) Construction of FK$_2$UPA$^B$(BC) [ie. tPA(1–49)-tPA(176–275)-uPA(159–411)]

Deletion mutagenesis is carried out as described in the general protocol (cf. Example 14) on mp18/SacI/TPA$^A$UPA$^B$(BC) [cf. Example 18 A] using a mutagenic primer which is complementary to the coding strand of t-PA (728–706) and t-PA (327–307) with a substitution of the nucleotide T at position 327 for the nucleotide C.

Positive clones obtained from hybridization are confirmed by restriction analysis with SacI. In the mutants a 1.5 kb band is observed compared to the wild type which yields a 1.9 kb fragment. Mutants are further confirmed by EcoRI digest. One mutant clone having the correct structure is referred to as mD18/SacI/FK$_2$UPA$^B$(BC). The deletion is verified by the chain terminator sequencing method using a sequencing primer of the sequence

5' CCCAGTGCCTGGGCATTGGGGTTCTGTGCTGTG 3'

This primer is complementary to the coding strand of t-PA (853–821) with a mismatch at position 838 (t-PA)

5) Similar deletion mutagenesis protocols are used to generate

K$_2$UPA$^B$(BR) [tPA(13)-tPA(176–262)-uPA(132–411)]
FUPA$^B$(BR) [tPA(149)-uPA(134–411)]

FK$_2$UPA$^B$(BR)   [tPA(1–49)-tPA(176–262)-uPA(132–411)] and
FGK$_2$UPA$^B$(BR)  [tPA(1–86)-tPA(176–262)-uPA(132–411)].

F) Insertion of hybrid PA coding sequences into mammalian cell expression vector Insertion of FUPA$^B$(BC), K$_2$UPA$^B$(BC), FK$_2$UPA$^B$(BC) and FGK$_2$UPA$^B$(BC). RF DNA from mp18/SacI/K$_2$UPA$^B$(BC), mPlS/SacI/FUPA$^B$(BC), mp18/SacI/FK$_2$UPA$^B$(BC) and mp18/SacI/FGK$_2$UPA$^B$(BC) are each cut with SacI. The smaller of the two resulting fragments is isolated and is ligated to SacI cut pBR4A (of, Example 5) vector fragment, transferred into E. coli HB101 and correct orientation and correct size inserts are confirmed by digestion with BamHI and SacI, respectively. The resulting plasmids are designed pCGC5/K$_2$UPA$^B$, pCGC6/FUPA$^B$, pCGC7/FK$_2$UPA$^B$ and pCGC8/FGK$_2$UPA$^B$, respectively.

2. Similarly K$_2$UPA$^B$(BR), FUPA$^B$(BR), FK$_2$UPA$^B$(BR) and GFK$_2$UPA$^B$(BR) DNSa see above) are each inserted Into pBR4A. The obtained plasmids are designated pBRS/

$K_2UPA^B$, PBR6/FUPA$^B$, pBR7/FK$_2$UPA$^B$ and pBRS/FGK$_2$UPA$^B$, respectively.

Example 19: Mammalian expression vectors comprising the DHFR gene

Plasmid pSV$_2$dhfr (ATCC 37145) is a plasmid allowing selection of transformants of DHFR-containing cells by selection using the antifolate drug methotrexate or selection of DHFR transformants of DHFR CHO cells [DUKX1 cells; G. Urlaub, Proc. Natl. Acad. Sci. U.S.A. 727, 4216–4220 (1980)]. Into the single BamHI site of this plasmid can be cloned the BamHI fragment of pCGA28 containing the modular t-PA gene. Plasmids containing either of the two possible orientations are designated pCGA700a/tPA and pCGA700b/tPA. Both can be used to express t-PA in tissue culture cells but preferred is the pCGA700a/tPA, in which transcription of the t-PA gene is in the same direction as that of the DHFR gene, as this orientation frequently leads to slightly higher expression levels than with plasmids that are convergently transcribed.

In an analogous fashion the modular genes encoding hybrid plasminogen activators (below) from plasmids pBR1A(t-PA), pBR$_2$A(UPA$^A$TPA$^B$), pCGC1/UPAAIPA$^B$, and pCGC2/UK=TPA$^B$ can be combined as BamHI fragments with the DHFR gene of pCGA700a/tPA to form plasmids pCGA701a/tPA, pCGA702a/UPA$^A$TPA$^B$ pCGA705a/UPA$^A$TPA$^B$ and pCGA707a/UK$_2$TPA$^B$ respectively, in which the modular plasminogen activator gene is transcribed in the same direction as the DHFR gene, and pCGA701b/tPA, pCGA702b/UPA$^A$TPA$^B$, pCGA705b/UPA$^A$TPA$^B$, pCGA707b/UK$_2$TPA$^B$ in which both genes are transcribed in opposite directions. Due to the presence of a BamHI sequence in the portion encoding the u-PA B-chain the modular plasminogen activator gene can only be isolated by a partial cut (2 of the 3 BamHI sites) of the neo$^R$ plasmid followed by isolation of the appropriate fragment (cf. figures) by agarose gel electrophoresis. Thus, from pBR3A(u-PA), pBR4a(TPA$^A$UPAB), pBR5/K$_2$UPA$^B$, pBR6/FUPA$^B$, pBR7/FKUPA$^B$, pBRS/FGK$_2$UPA$^B$, pCGCB/UK$_2$UPA$^B$, pCGC4a/TPA$^{AUPAB}$, pCGC5/K$^A$UPA$^B$, pCGC6/FUPA$^B$, pCGC7/FK$^A$UPA$^B$. and pCGCS/FGK$_2$UPA$^B$ can be constructed pCGA70Ba/uPA, pCGA704a/TPA$^A$UPA$^B$, rCGA705a/K=UPA$^B$, pCGA70ga/FUPA$^B$. pCGA706a/FK$_2$UPA$^B$, pCGA707a/FGK$_2$UPA$^B$. pCGA709a/UK$_2$UPA$^B$, pCGA711a/TPA$^A$UPA$^B$, pCGA712a/K$_2$UPA$^B$, pCGA713a/FUPA$^B$, pCGA714a/FK$_2$UPA$^B$ and pCGA715a/FGK=UPA$^B$, respectively, in which the plasminogen activator genes all are transcribed in the same direction as the DHFR gene, and further pCGA703b/uPA, pCGA704b/TPA$^A$UPA$^B$, pCGA708b/[UPA$^B$, pCGA705b/K$_2$UPA$^B$, pCGA706b/FK$_2$UPA$^B$, pCGA707b/FGK$_2$UPA$^B$, pCGA709b/UK$_2$UPA$^B$, pCGA711b/YPAAUPA$^B$, pCGA712b/K$_2$UPA$^B$, pCGA713b/FUPA$^B$, DCGA714b/FK$_2$UPA$^B$ and pCGA715b/FGK$_2$UPA$^B$. in which both genes are transcribed inconvergently.

Example 20: Production of hybrid plasminogen activators by transformed mammalian cells A) Maintenance and DNA transfection of tissue culture cells: general procedure DNA constructs are expressed in DUKXB1, a mutant of Chinese hamster ovary (CHO) cells lacking the enzyme dihydrofolate reductase [G. Urlaub et al., Proc. Nat. Acad. Sci. USA 7-7, 4216–4220 (1980)]. DUKX1 cells are cultured in alpha-MEM medium containing nucleosides (GIBCO) supplemented with 5% fetal calf serum.

Cells are plated at a density of 10 000/ cm in 6-well multiplates (3.4 cm diameter) and transformed with 4 µg DNA: DNA is dissolved at 50 µg/ml in 10 mM Tris/HCl pH 7.0 containing 0.1 mM EDTA, cooled on ice for 5 min., 0.25 volumes 1 M CaCl$_2$ is added and incubated on ice for 10 min. The mixture is then mixed with an equal volume of 2×HBS (50 mM Hepes, 280 mM NaCl, 0.75 mM Na$_2$HPO$_4$, 0.75 mM NaH$_2$PO$_4$. pH 7.12) followed by another 10 min incubation on ice. Finally this DNA-Ca-phosphate coprecipitate is added to the culture medium and cells are incubated with the DNA for 16–18 h, followed by a glycerol shock, i.e. cells are rinsed with TBS (80 g/l NaCl, 3.8 g/l KCl, 1 g/l Na$_2$HPO$_4$·2H$_2$O, 0.114 g/l CaCl$_2$·2H$_2$O, 0.11 g/l MgCl$_2$·6H$_2$O, 25 mM Tris/HCl pH 7.5), incubated 1 min with 20% (v/v) glycerol in TBS, rinsed again with TBS and cultured 24 h in tissue culture medium. Cells are then trypsinizod and the cells are transferred to 8 cm diameter Petri dishes. The next day the initial culture medium without selective agent is replaced by medium with 1 mg/ml geneticin. Medium is replaced every third or fourth day. Colonies can be seen around day 14. Cells from individual colonies are isolated by scraping them off with the tip of a piperman while simultaneously sucking them into the tip filled with trypsin solution and transferring each to a well of a 24 well multiplate supplied with medium containing geneticin. When confluent these cultures are split into the wells of a 6 well multiplate and subsequently into 8 cm diameter Petri dishes.

B. Agarose plate assays for plasminogen activators

These sensitive assays for plasminogen activators use agarose gels to which plasminogen (stock solution prepared by dissolving plasminogen Sigma A-6877 at 1 mg/ml in and dialyzing it twice against 100 volumes 50 mH Tris/HCl pH 8.0) or either casein (added as non-fat milk) or fibrin (added as fibrinogen plus thrombin) is added. The sample containing plasminogen activator is applied into holes punched into a 4 mm thick agarose layer and the gel is subsequently incubated at 37° C. The enzymatic activity is then detected in that the plasminogen activator diffuses radially away from the sample well, converts the plasminogen in the gel to plasmin which in turn digests the casein or fibrin thus producing a clear halo in the opaque gel around the sample well. The radius of the halo measured from the rim of the sample well) is a measure for the amount of plasminogen activated. The assay does not show a linear response to the amount of plasminogen activator added. For assay of low amounts of plasminogen activator the incubation can be prolonged to several days. The procedure and calibration of the casein assay is as described in Tang et al. [Ann. N.Y. Acad. Sci. 434, 536–540 (1984)] except that instead of 2%; (w/v) Carnation non-fat milkpowder 12.5% (v/v) sterilized (UHT) fat-free milk from Migros Corp. (Switzerland) is used. When fibrin [Granelli-Piperno and Reich, J. Exp. Med. 148, 223–234 (1978)] is used as a substrate 0.2 g agarose is dissolved in 15 ml 0.9% NaCl and cooled to 42° C. At this point 5 ml 0.9% NaCl containing 80 mg bovine fibrinogen (Sigma F-8630), 0.1 ml plasminogen solution (above) and 0.1 ml 100 mg/ml sodium azide at 42° C. are added. Finally, 0.2 ml bovine thrombin (Sigma T-6634, dissolved at 16.6 NIH units/ml in 0.9% NaCl) are added and the mixture is quickly poured into a Petri dish (8 cm diameter) and allowed to cool to room temperature for one hour. The resulting gel is about 4 mm thick and can be stored at 4° C. for several days or used immediately in the same manner as the casein containing gel above.

C. Production of hybrid PA proteins in hamster cells

CHO DUKXB1 cells are transformed with DNA of plasmids pBR1A, pBR1B, pBR2A pBR2B pBR3A, pBR3B, pBR4A pBRS/K2UPA$^B$, pBRT/FK$_2$ UPA$^B$, pBRS/FGK$_2$UPA$^B$, pCGC1/UPA$^A$TPA$^B$, pCGC2/UK$_2$UPA$^B$, pCGC3/UK$_2$TPA$^B$, pCGC4a/TPA$^A$UPA$^B$, pCGC5/K$_2$UPA$^B$ pCGC6/FUPA$^B$ pCGC7/FK$_2$ UPA$^B$ and pCGCS/FGK$_2$UPA$^B$ respectively, as described above (Example 20A) Colonies appear around day 10, colonies are picked around day 15 as described above and two weeks later cell number has increased sufficiently to measure PA as described above. Untransformed cells and cell lines transformed with pBR1B, pBR2B, pBR3B, which contain the inserted SacI fragment in the antisense orientation do not produce detectable amounts of PA.

D. Enzyme activity in media conditioned by transformed CHO cells

Conditioned medium from plasmid transformed and control CHO cells are prepared by cultivating 200,000–500,000 cells/ml for 24 hours in Alpha-MEM with nucleosides and 5% fetal calf serum and 0.03 ml is incubated on agarose plates containing casein or fibrin for the time period indicated below. On the fibrin plate a minimal background activity, presumably due to endogenous hamster t-PA, is detected in the DUKXB1 conditioned medium. No halo appears on casein plates if samples of hybrid protein are mixed with 3 microliter of rabbit anti-tPA antibodies (raised against purified Bowes melanoma t-PA) or anti-urokinase anti bodies (raised against Serono urokinase). Anti-tPA antibody does not inhibit u-PA enzyme, nor does anti-urokinase antibody inhibit t-PA to a significant extent. The results are summarized in Table 1.

TABLE 1

Activity of different plasminogen activators

| No. | transforming plasmid | casein plate 18 h | casein plate 36 h | fibrin plate 90 min | fibrin plate 300 min |
|---|---|---|---|---|---|
| 1. | pBR1A(t-PA) | 2 mm | 5 mm | 1 mm | 2 mm |
| 2. | pBR2A(UPA$^A$TPA$^B$) | 0 mm | 0 mm | 0.5 mm | 1.5 mm |
| 3. | pBR3A(u-PA) | 5 mm | 10 mm | 0.5 mm | 2.5 mm |
| 4. | pBR4A(TPA$^A$UPA$^B$) | 6 mm | 11 mm | 2 mm | 3 mm |
| 5. | pBR5/K$_2$UPA$^B$ | 3 mm | 8 mm | not determined | |
| 6. | pBR7/FK$_2$UPA$^B$ | 4 mm | 9 mm | 1 mm | 2 mm |
| 7. | pBR8/FGK$_2$UPA$^B$ | 3.5 mm | 7 mm | 0.8 mm | 2 mm |
| 8. | pCGC1/UPA$^A$TPA$^B$ | 0 Mm | 6 mm | 0.2 mm | 2 mm |
| 9. | pCGC2/UK$_2$UPA$^B$ | 5 mm | 10 mm | 1 mm | 2.5 mm |
| 10. | pCGC3/UK$_2$TPA$^B$ | 3.5 mm | 5 mm | 1.5 mm | 2.5 mm |
| 11. | pCGC4a/TPA$^A$UPA$^B$ | 2.5 mm | 5 mm | 0.5 mm | 1.5 mm |
| 12. | pCGC5/K$_2$UPA$^B$ | 6.5 mm | 12 mm | 6 mm | >10 mm |
| 13. | pCGC6/FUPA$^B$ | 2 mm | 8 mm | 0 mm | 1 mm |
| 14. | pCGC7/FK$_2$UPA$^B$ | 2.5 mm | 5 mm | 1 mm | 2 mm |
| 15. | pCGC8/FGK$_2$UPA$^B$ | 2.5 mm | 6 mm | 1 mm | 2 mm |
| 16. | mtPA 1 µg/ml | 3 mm | 7 mm | 1.5 mm | 3 mm |
| 17. | DUKXB1 control | 0 mm | 0 mm | 0 mm | 0.5 mm |

Example 21: Preparation of hybridoma cells and isolation of monoclonal antibodies a) Source of immunogen: A sample of semi-purified natural human (melanoma t-PA) having an estimated purity of >90%.

b) Immunization protocol: Three groups of BALB/c mice (Tierfarm Sisseln, Switzerland) 10–14 weeks old are immunized by injection into the two hind footpads and subcutaneously of 100 µg of melanoma t-PA emulsified in complete Freund's adjuvant (Difco). Subsequently, first group (Nr. 405) receives 10 µg of t-PA in incomplete adjuvant, every week for six weeks while the second group (406) receives the same amount biweekly. The third group (407) is given twice 50 µg t-PA at three week intervals. All animals are bled at week 4 and week 8. For the last injection 100 µg t-PA in PBS is given j.p. and four days later spleen cells are fused with SP2/o mveloma line according to standard procedure. Only those mice with high anti-t-PA antibody liter are used for fusion.

c) Cell fusion: All fusion experiments are performed according to the procedure of G. Köhler and C. Milsrein [Nature 256, 495 (1975)] using the nonsecreting Sp 2/0-Ag14 myeloma line [M. Shulman, C. D. Wilde and G. Köhler, Nature 276, 269 (1978)]. $10^6$ spleen cells are mixed with 107 myeloma cells in the presence of I ml of 50% polyethylene glycol (PEG 1500, Serra). After washing, the cells are resuspended in 48 ml of standard Dulbecco's minimum essential medium (Gibco No. 0422501). $3 \times 10^6$ normal mouse peritoneal exsudate cells per fusion are added as feeder cells. The cells are distributed into 3×1 ml costar wells and fed 3 times per week with standard HAT selection medium for 3 to 6 weeks. When the growth of hybridoma cells becomes visible, the supernatants are screened by both direct antigen binding (ELISA) and neutralization (casein) assays (see below). Results of 4 fusion experiments are as follows:

Of 192 wells seeded, 192 hybridomas are obtained. Of those, 24 produce anti-t-PA antibody. Of 24 positive hybridomas, 14 are cloned and out of 574 clones ohio:ned. 3] are found to produce anti-t-PA mAb stably. Three (clones 105B.23.7 and 407A.15.27) of these are injected into mice and ascetic fluids are produced for further studies.

d) Isolation and purification of monoclonal antibody:

BALB/c mice 8–10 weeks of age (Tierfarm Sisseln, Switzerland) are pretreated intraperitoneally with 0.3 ml pristane (Aldrich). 2–3 weeks later, $2-5 \times 10^6$ cloned hybridoma cells 405B.33.3, 406A.23.7 and 407A.15.27 and 0.2 ml pristane are inoculated intraperitoneally. After 8–10 days ascites fluid is collected, centrifuged at 800×g and stored at −20° C.

Defrosted ascites fluid is centrifuged at 50000×g for 60 min. A fat layer floating on the surface is carefully removed, and the protein concentration is adjusted to a concentration of 10–12 mg/ml. Crude immunoglobulin is precipitated by dropwise addition of 0.9 volume equivalents of saturated ammonium sulphate at 0° C., then dissolved in 20 mM Tris-HCl/50 mM NaCl (pH 7.9) and dialysed against the same buffer. An immunoglobulin fraction is obtained by DEAE-D52 cellulose (Whatman) chromatography using a buffer gradient system of 20 mM Tris-HCl/25–400 mM NaCl, pH 7.9. The immunoglobulin is again precipitated with ammonium sulphate and dissolved in PBS at a concentra tion of 10 mg/ml.

Sodium dodecyl sulphate polyacryl amide gel electrophoresis (SDS-PAGE) demonstrates a purity grade of more than 95 percent for the monoclonal antibodies.

e) Determination of class and subclass of monoclonal antibodies:

The class and subclass of monoclonal antibodies produced by cloned hybridoma cells is determined by the known immunodiffusion technique of Ouchterlony (agar-gel immunodiffusion method) using class and subclass specific rabbit antibodies (Bionetics).

| 405B.33.3 | $\gamma_1\kappa$ |
| 406A.23.7 | $\gamma_2 b\kappa$ |
| 407A.15.27 | $\gamma_2 a\kappa$ | f) Enzyme immunoassay (ELISA): Microliter plates are coated with 0.5 µg per well of a t-PA preparation (purity >95%) in 100 µl PBS. Free binding capacity of the plate is saturated with a buffer of 0.2% gelatin in PBS containing 0.2% NaN$_3$ (w/v), pH 7.4. 100 µl probes containing monoclonal antibodies 405B.33.3, 406A.23.7 and 407A.15.27, respectively, are incubated in the wells at 37° C. for 2 hours. The plates are washed with PBS containing 0.05% Tween 20, then incubated at 37° C. for 2 hours with a phosphatase conjugated rabbit anti-mouse immunoglobulin preparation. The fixed enzyme is developed by incubating (37° C., 30 to 60 min) with a solution of the enzyme substrate p-nitrophenyl phosphate (1 mg/ml in diethanolamine buffer 10% containing 0.5 mM MgCl$_2$ and 0.02% (w/v) NaN$_3$, pH 9.8) and measuring the optical density at 405 nm.

The same ELISA is also performed by using urokinase. None of the mAb binds to urokinase. All mAbs are t-PA specific.

g) Casein lysis assay (neutralization test):

In order to determine inhibitory action of mAbs, t-PA is first mixed with mAbs 405B.33.3, 406B.23.7 and 407A.15.27, respectively, and incubated for 30–60 min at 4° C. and then the usual casein/plasminogen agar assay is performed (see Example 20B). None of the mAbs inhibits the t-PA activity except that mAb 405B.33.3 causes a delay (more than 6 hours) in casein lysis.

Example 22: Purification of hybrid plasminogen activator, general procedure

Extracts from transformed yeast cells are prepared as described in Example 16. Extracts from plasmid-transformed mammalian cells, such as CHO cells, are prepared as follows:

The cells are first cultured to 70–80% confluency. Then the cell monolayer is rinsed with medium as described above but omitting the serum followed by cultivating the cells for an additional period of 5–7 days. Medium is harvested every 24 h, at the same time supplying fresh medium to the cells. The conditioned medium thus obtained is then centrifuged at 5000×g for 30 min. and filtered through a 0.45 µm filter to remove unwanted cell debris prior to affinity chromatography. As affinity matrix is used either the immobilized protease inhibitor DE-3 from Erythrina latissima or immobilized antibodies to u-PA or t-PA.

Hybrid PAs containing the catalytic B-chain of t-PA are purified from the conditioned medium prepared as described above or from yeast cell extracts using the protocol originally developed for purification of t-PA from melanoma cell-conditioned medium [cf. C. Heussen et el., J. Biol. Chem. 259, 11635–11638 (1984)].

All hybrid PAs are purified using polyclonal antibodies raised in rabbits or goats against the parental u-PA and t-PA enzymes or using monoclonal antibodies (of mouse origin) raised against the parental enzymes provided these recognize an epitope present in the hybrid PA in question (cf. Example 21). The antibody of choice is immobilized on an insoluble matrix such as Affigel or Sepharose-4B. The conditioned medium prepared as described above or the yeast cell extract is then applied to a column of affinity-matrix, unwanted proteins are washed away using an appropriate buffer, for example Dulbecco's PBS [0.1 g/l CaCl$_2$, 0.2 g/l KCl, 0.2 g/l KH$_2$PO$_4$ 0.047 g/l MgCl$_2$, 8.0 g/l NaCl, 1.15 g/l Na$_2$HPO$_4$; J. Exp. Med. 99, 167 (1954)] and then the PA is eluted from the column using the chaotropic agent potassium thiocyanate [cf. M. Einarsson et al., Blochim. Biophys. Acta 830, 1–10 (1985)] or a low pH buffer like 0.1–0.2 M glycin-HCl (pH 2.1).

After purification using monoclonal antibodies the hybrid PAs have a purity of more than 90%.

Example 23: Purification of UK$_2$TPA$^B$(BC)

a. Preparation of a DE-3 Sepharose column

Per ml of cyanogen bromide activated Sepharose 4B® (Pharmacia) are coupled 5 mg of purified inhibitor from Erythrina latissima [F. J. Joubert et al., Moppe-Seyler's Zeitschr. Physiol. Chem. 302, 531 (1981)], according to the manufacturer's instructions. The matrix is equilibrated with 0.2 M ammonium acetate buffer pH 7.0 containing 0.2 M NaCl, 0.1% Synperonic® and 0.02% sodium azide.

b. Chromatographic purification of UK$_2$TPA$^B$(BC) on DE-3 Sepharose 4B®

Conditioned medium Ccf. Example 22) is made 0.1% with respect to Synperonic® and then applied to the DE-3 Sepharose®. After gentle stirring for 1 hour at 4° C., the DE-3 Sepharose 4B® is poured in a column, and washed with 0.2 M NaCl, 0.1% Synperonic until the UV absorbance at 280 nm reaches baseline levels indicating the absence of proteins in the eluate. Washing is then continued with 0.2 M ammonium acetate buffer pH 7.0 containing 0.2 M ammonium thiocyanate and 0.1% Synperonic. After the UV absorbance at 280 nm indicates the absence of protein in the eluate the column is eluted with 0.2 M ammonium acetate buffer pH 7.0 containing 1.6 M ammonium thiocyanate and 0.1% Synperonic®. Fractions containing the highest amidolytic activities, measured using the fluorometric assay with Cbz-Gly-Gly-ArE-AMC as substrate [M. Zimmermann et al., Proc.Natl.Acad. Sci. USA. 7–5, 750 (1978)], are pooled. At least 80% of the activity applied to the DE-3 Sepharose 4B® material is recovered in a single peak.

The pooled active fractions are dialyzed against 0.2 M ammonium acetate buffer pH 7.0 containing 0.1% Synperonic® and applied to a column containing monoclonal antibody 407A.15.27 which is directed against the first kringle domain of t-PA, coupled to Sepharose 4B®, equilibrated in 0.2 M ammonium acetate buffer pH 7.0 containing 0.1% Synperonic®, in order to remove endogenous t-PA. The effluent, containing the UK$_2$TPA$^B$(BC), is collected.

Reverse phase HPLC of the purified UK$_2$TPA$^B$(BC) on a Nucleosil® 300-5-C18 column with dimensions 4×110 mm shows a single peak on elution with a linear gradient over 30 min starting with 70% solution A consisting of water containing 0.1 µl trifluoroacetic acid and 30% solution B consisting of acetonitril containing 0.08% trifluoroacetic acid and ending at 40% A and 60% B. The purified protein showed upon N-terminal sequence analysis of the first ten amino acid residues the sequence SNELHQVPSN, which is identical to the sequence expected from the DNA sequence encoding the molecule.

Example 24: Purification of FK$_2$UPA$^B$(BC) and K$_2$UPA$^B$(BC)

a. Preparation of antibody affinity columns

Rabbit anti-uPA antibodies purified from rabbit anti-uPA serum, mono clonal antibodies 405B.33.3 and 406A.23.7, are coupled to cyanogen bromide activated Sepharose 4B® (Pharmacia) according to the manufacturer's instructions using 6 mg of antibody per ml of activated Sepharose. The gel matrix is equilibrated with PBS containing 0.1% Synperonic® and 0.1% sodium azide.

b. Chromatographic purification of $FK_2UPA^B(BC)$ and $K_2UPA^B(BC)$ on antibody Sepharose 4B.

Conditioned medium (cf. Example 22) is made 0.1% with respect to Synperonic® and applied to the anti-uPA Sepharose-4B or to the 405B.33.3 or to the 406A.23.7 Sepharose 4B. The latter two antibodies are directed against the second kringle domain of t-PA. After gentle stirring for 2 hours at 4° C., the antibody Sepharose is poured in a column and washed with PBS containing 1 M NaCl and 0.1% Synperonic® until the UV absorbance at 280 nm indicates an absence of protein in the eluate. The column is then eluted with 0.2 M glycine-HCl buffer pH 2.5. Fractions are collected in tubes containing a neutralizing amount of 1 M Tris. Fractions containing the highest amidolytic activities, measured using the fluorometric assay with Cbz-Gly-Gly-Arg-AMC as substrate [M. Zimmermann et al., Proc. Natl.Acad. Sci. USA. 7–5, 750 (1978)], are pooled.

Reverse phase HPLC of the purified $FK_2UPA^B(BC)$ and $K_2UPA^B(BC)$ on a Nucleosil® 300-5-C18 column with dimensions 4×110 mm shows a single peak each on elution with a linear gradient over 30 min starting with 70% solution A consisting of water containing 0.1% trifluoroacetic acid and 30% solution B consisting of acetonitril containing 0.08% trifluoroacetic acid and ending at 40% A and 60% B. N-Terminal sequence analysis of the first five residues of the purified proteins results in the sequence SYQGN for $K_2UPA^B(BC)$ and SYQVI for $FK_2UPA^B(BC)$, which is identical to the sequences expected from the DNA sequences encoding each molecule.

Example 25: Activity assay of hybrid plasminogen activators in the presence and absence of fibrinogen fragments The double rate assay as described by Verheyen et al. [Thromb. Haemost. 48, 266 (1982)], based on the conversion of plasminogen into plasmin by the plasminogen activator, followed by the reaction of plasmin with the chromogenic plasmin substrate H-D-valyl-Lleucyl-L-lysine-p-nitroanilide dihydrochloride, is employed. The assay is carried out in a microtiter plate having 96 wells and with a Tiretrek® microtiter plate reader. The wells contain 120-X μl 0.1 mol/l Tris/HCl buffer at pH 7.5 containing 0.1% Tween 80, 20 μl Glu-plasminogen at 1.3 μmol/l in the above mentioned Tris buffer, 100 pl plasmin substrate at 0.7 mmol/l in Tris buffer, X pl sample at known concentration (X corresponds to 10, 20, 40 and 60 pl, respectively), or urokinase standard with defined activity expressed in International Units, and 10 μl stimulator (fibrinogen fragments) at 3 mg/ml in distilled water or 10 μl distilled water if the experiments is to be performed without stimulator. The increased light absorption divided by the square of the incubation time is proportional to the plasminogen activator activity at a known concentration of activator and is expressed in International Units. High molecular weight urokinase with a defined activity expressed in International Units (American Diagnostics) has been used as a standard. Each plasminogen activator has been asseyed under identical condition in the absence and presence of fibrinogen fragments, respectively- Under these conditions the difference in activities obtained are a measure for the stimulation of the plasminogen activators by the fibrinogen fragments. Table 2 contains the results of the analysis, which indicates the absence of stimulation for the urokinase standard in contrast to the stimulation exerted by fibrinogen fragments on the novel plasminogen activator molecules containing the catalytic domain of urokinase. Irrespective of the absence of one or more of the non-catalytic domains F, G, $K_1$ or $K_2$ of tissue plasminogen activator a stimulation by fibrinogen fragments is observed for all hybrid molecules tested.

TABLE 2

| plasminogen activator | I.U. stimulated/I.U. unstimulated |
|---|---|
| u-PA standard | 1.0 |
| $FGK_2UPA^B(BC)$ | 5.0 |
| $FK_2UPA^B(BC)$ | 10.0 |
| $K_2UPA^B$ | 6.0 |
| $FUPA^B$ | 3.6 |

Example 26: Clot lysis activity of mutant plasminogen activators

Clot lysis activities are determined using the assay as described by R. D. Philo and P. J. Gaffney [Thromb. Haemost. 45, 107–109 (1981)]. A logarithmic plot of the lysis time versus plasminogen activator concentration results in a straight line. The specific activity of a plasminogen activator is determined by comparison with the curves obtained from a standard preparation of tissue plasminogen activator or urokinase.

The curves of all activators measured have approximately the same slope which allows a direct relation between the time needed for clot lysis and their specific activity. As the different plasminogen activators do not possess the same molecular mass, the specific activities have to be expressed in a molar concentration, instead of the usual weight concentration, in order to obtain a meaningful criteria for the efficacy of the different molecules. $UK_2TPA^B(BC)$ is found to be at least as active as the standard t-PA, whereas $FGK_2UPA^B(BC)$ and $FK_2UPA^B(BC)$ show activities which are almost equal to t-PA but significantly higher than the u-PA standard. $K_2UPA^B(BC)$ is found to possess an activity almost identical to the u-PA standard. The activities of the assay are summarized in Table 3:

TABLE 3

| plasminogen activator | clot lysis units/pmol* |
|---|---|
| t-PA standard | 23.6 |
| $UK_2TPA(BC)$ | 28.6 |
| u-PA standard | 13.2 |
| $FGK_2UPA^B(BC)$ | 24.3 |
| $FK_2UPA^B(BC)$ | 20.7 |
| $K_2UPA^B(BC)$ | 10.4 |
| $FUPA^B(BC)$ | 2.7 |

*Clot lysis units are expressed in picomol t-PA, using the molecular mass of t-PA based in its amino acid sequence, and a specific activity of 400,000 clot lysis units/mg.

Example 27: Clearance of plasminogen activator mutant molecules from the circulation of rabbits 1. Labelling All mutant molecules are radiolabelled with $^{125}J$ by using the Iodogen method [P. J. Fraker et al., Biochem. Biophys. Res. Commun. 80, 849–857 (1978)].

To remove excess free $^{125}J$ the mutant molecules are affinity-purified either using the method described in Example 23 (PAs having the t-PA B-chain) or the method described in Example 24 (PAs having the u-PA B-chain).

Specific radioactivities of 2–20 μCi/μg protein are usually obtained. Homogeneity of the labelled molecules is assessed by SDS electrophoresis followed by X-ray autoradiography. In all cases the mutant molecules migrate under non-reducing conditions as single bands and with Mr's identical to the non-labelled proteins.

2. Clearance studies

Experiments are performed in New Zealand white rabbits weighing 1.8 to 2.4 kg. The animals are anesthetized with 1750 mg/kg Urethan® (Merck, Darmstadt, Germany) subcutaneously. Tracheotomy is performed and a plastic tubing is inserted in the external jugular vein and the common carotid artery. 0.5 ml phosphate-buffered saline containing about 300–500 ng of the mutant PA are injected into the jugular vein and serial blood samples (2 ml each) are acquired sequentially throughout a 60 min interval via the carotid artery.

The blood samples are collected on citrate, immediately centrifuged at 3000 rpm for 15 min and the plasma decanted. Aliquots are precipitated in 10% trichloroacetic acid and the pellets counted in a γ-counter.

In comparison to t-PA isolated from the Bowes melanoma cell-line the mutant molecules show the following half-life in circulation.

TABLE 4

| hybrid PA | half-life (min) of circulating plasminogen activator |
|---|---|
| t-PA | 2 |
| UK$_2$TPA$^B$(BC) | 20 |
| FGK$_2$UPA$^B$(BC) | 10 |
| FK$_2$UPA$^B$(BC) | 10 |
| K$_2$UPA$^B$(BC) | 30–40 |

The clearance pattern of t-PA is typically bi-exponential with a very rapid g-phase followed by a slower B-phase elimination. Elimination of UK$_2$TPA$^B$(BC) and K$_2$UPA$^B$(BC) is almost monophasic, suggesting that distribution to a second compartment is suppressed.

3. Organ distribution

Rabbits are treated as above. At 20 min after injection of the iodinated mutant molecules the rabbits are sacrificed, the major organs are taken, the weight determined and an aliquot after homogenisation counted in the γ-counter.

TABLE 5

| | percentage of recovered radioactivity | | |
|---|---|---|---|
| | t-PA | UK$_2$TPA$^B$(BC) | K$_2$UPA$^B$(BC) |
| liver | 40 | 10 | 7 |
| heart | <1 | <1 | <1 |
| lung | <1 | <1 | <1 |
| spleen | <1 | <1 | <1 |
| kidney | 1.6 | 2 | 4 |

The mutant PAs show a larger fraction of the radioactive molecules still remaining in circulation (supra), coinciding with a much reduced liver-clearance. Reduced uptake by the liver is therefore the explanation for the extended half-life and the monopbasic elimination pattern of the mutant molecules, especially UK$_2$TPA$^B$(BC) and K$_2$UPA$^B$(BC).

In Examples 28–3, plasmids pCGC5/K$_2$UPA$^B$, pCGC6/FUPA$^B$, pCGC7/FK$_2$UPA$^B$ and pCGC8/FGK$_2$UPA$^B$ (cf. Example 18) are used to construct yeast expression plasmids. The yeast invertase signal sequence is fused in frame to the different coding sequences. They are expressed under the control of the inducible PHO5 promoter. In some constructs glycosylation sites are mutated.

Example 28: Cloning of the phage F1 origin of replication into expression vector pJDB207:

Plasmids of the pEMBL family [Dente et al., Nucl. Acids Res. 11, 1645–55 (1983)] contain a region of the phage F1 genome that provides all cis-acting elements for DNA replication and morphogenesis. Only upon superinfection with phage F1 (helper) large amounts of single-stranded plasmid DNA are excreted into the medium.

Plasmid pEMBL19(+) is digested with ScaI and EcoRI, A 2.2 kb fragment is isolated which contains part of the ampicillin resistance gene of pBR322 (ScaI site), the F1 intergenic region and part of the B-galactosidase gene up to the polylinker region (EcoRI site).

Plasmid pJDB207 is linearized by cutting with HpaI. 10 μg of linearized plasmid are partially digested with 7.5 units of EcoRI in the presence of 0.1 mg/ml of ethidiumbromide for 40 min at 37° C. The reaction is stopped by the addition of 10 mM EDTA. The 1.8 kb EcoRI-HpaI fragment is isolated on a preparative 0.8% agarose gel.

3 μg of HpaI cut pJDB207 are further digested with ScaI. The 4.8 kb large HpaI-ScaI fragment is isolated. DNA fragments are electroeluted from the agarose gel blocks, purified by DE52 chromatography and ethanol precipitation.

0.2 μmoles each of the 2.2 kb ScaI-EcoRI fragment and the 1.8 kb EcoRI-HpaI fragment and 0.1 pmoles of the HpaI-ScaI vector fragment are ligated. The ligation mixture is used to transform competent E. coli HB101 Ca$^{2+}$ cells.

Plasmid DNA of 12 ampicillin-resistant colonies is analysed by EcoRI/PstI double digestion. The DNA of a single clone with the correct restriction fragments is chosen and referred to as pJDB207F1Lac.

Example 29: Construction of plasmid pJDB207/PHO5-I-FK$_2$UPA$^B$:

The coding sequence of FK$_2$UPA$^B$ as present in plasmid pCGC7/FK$_2$UPA$^B$ is adapted for expression in yeast by fusing the yeast invertase signal sequence and expressing the gene under the control of the PHO5 promoter.

Plasmid pCGC7/FK$_2$UPA$^B$ (see Example 18D) is digested with PstI and BamHI. The 1147 bp PstI-BamHI fragment contains the FK$_2$UPA$^B$ coding sequence from the PstI site at nucleotide position 199 of t-PA (FIG. 1) to the BamHI site at position 1322 of u-PA (FIG. 3).

Plasmid pJDB207/PHO5-I-TPA (see Example 6C) is cut with SalI and PstI. The 891 bp fragment is isolated. It contains the PHO5 promoter, invertase signal sequence and 19 bases of t-PA (PstI site).

Plasmid pJDB207/PHO5-I-UPA (see Example 8) is digested with SalI and BamHI. The 6.6 kb vector fragment contains the 3' part of the u-PA gene from the BamHI site at nucleotide position 1323 (FIG. 3) to the position 1441 (PvuII site with XhoI linker added) and the PHO5 transcription termination signals.

0.2 pmoles each of the 891 bp SalI-PstI fragment and the 1147 bp PstI-BamHI fragment and 0.1 μmoles of the 6.6 kb SalI-BamHI vector fragment are ligated and used to transform E. coli HB101 Ca$^{2+}$ cells.

8 ampicillin resistant colonies are grown in LB medium containing ampicillin (100 mg/l). Plasmid DNA is isolated and analysed by EcoRI and HindIII restriction digests. One plasmid with the expected restriction fragments is chosen and referred to as pJDB207/PHO5-I-FK$_2$UPA$^B$.

Plasmids pCGC6/FUPA$^B$ and pCGCa/FGK$_2$UPA$^B$ can be used in the same way as pCGC7/FK$_2$UPA$^B$. The resulting yeast expression plasmids are designated pJDB207/PHOS-I-FUPA$^B$ and pJDB207/PHO5-I-FGK$_2$UPA$^B$ respectively.

Example 30: Mutation of the glycosylation site at [Asn 302] of the urokinase B-chain:

a) Cloning of a PstI-BamHI fragment of u-PA into M13mp18: The plasmid pJDB207/PHO5-I-UPA (see Example 8) contains the complete coding region of urokinase. The DNA is cut with PstI and BamHI. The 886 bp PstI-BamHI fragment from the urokinase gene contains the glycosylation site (Ash 302) at nucleotide positions 1033–1041. Another fragment of similar size is further cut by BstEII. The 886 bp PstI-BamHI fragment is isolated on a preparative 0.8% agarose gel.

M13mp18 RF-DNA is cut with PstI and BamHI. The 7.3 kb fragment is isolated on a preparative 0.8% agarose gel. The DNA fragments are electroeluted from the agarose gel and purified by DE52 chromatography and ethanol precipitation.

0.1 pmoles of the 7.3 kb PstI-BamHI cut vector and 0.2 μmoles of the 886 bp PstI-BamHi u-PA fragment are ligated. 1 μl and 3 μl of the ligation mixture are used for transformation of E. coli JM109 Ca$^{2+}$ cells according to the manual "M13 cloning and sequencing handbook" published by Amersham. 12 colourless plaques are picked and single-strand DNA is prepared [J. Messing, Methods in Enzymology 101, 21–78 (1983)]. The single-stranded DNA is used to prepare partially double-stranded DNA by annealing and extending the M13 universal primer with Klenow polymerase. The reaction product is extracted with phenol/chloroform and the DNA is precipitated with ethanol. The DNA is cut with PstI and BamHI. A 886 bp fragment indicates that the u-PA fragment has been cloned in the M13mp18 vector. One clone is further analysed and the correct insert is confirmed by sequencing. The clone is referred to as M13mp18/UPA.

b) Mutation of the glycosylation site at Ash302:

stranded template DNA is produced by one cycle of growth on the E. coli strain RZ1032 (dut$^-$, ung$^-$).

100 pmoles of the mutagenic oligonucleotide primer W are phosphorylated in 20 μl of 50 mM Tris-HCl pH 7.5, 10 mM MgCl$_2$, 5 mM DTT, 0.5 mM ATP and 20 units of T4 polynucleotide kinase (Boehringer). After 30 min at 37° C. the reaction is stopped by heating to 70° C. for 10 min.

0.3 pmoles of uracil containing M13mp18/UPA template DNA is incubated with 10 μmoles of phosphorylated mutagenic oligodesoxyribonucleotide primer W and 10 μmoles of M13 universal sequencing primer in 30 μl of 10 mM Tris-HCl pH 8.0, 10 mM MgCl$_2$. The sample is heated to 80° C. and allowed to cool to room temperature in a small water-bath.

c) Extension-ligation reaction:

To the above annealed sample 10 μl of an enzyme-dNTP mixture is added containing 1 mM dNTPs, 10 mM Tris-HCl pH 8.0, 10 mM mgCl$_2$, 20 mM DTT, 1 mM ATP, 400 units of T4 DNA ligase (Biolabs, 400 U/μl) and 6 units of Klenow DNA polymerase (Boehringer, 6 U/μl). Incubation is at 15° C. overnight.

d) Transformation of E. coli BMH71 cells:

The ligation mixture is diluted to 200 μl with TE. 0.1 μl, 1 μl and 10 μl of the extension-ligation mixture are added to competent E. coli BMH71 Ca$^{2+}$ cells (Kunkel, supra). After 30 min on ice the cells are heat-shocked for 3 min at 42° C. and then kept on ice. Cells are plated with top agar and E. coli JM101 indicator cells.

6 plaques are picked and used to infect E. coli JM109. Phages are isolated from the supernatant by PEG precipitation. Single-stranded DNA is prepared by extraction with phenol and precipitation with ethanol. Template DNAs are resuspended in TE.

Mutation of the AAT codon (Asn302) to the CAA codon (Gln302) is confirmed for one clone by DNA sequence determination with the above mentioned sequencing primer using the chain termination method [F. Sanger et al., Proc. Nat. Acad. Sci. USA 74, 5463–67 (1977)]. The mutation results in an Asn→Gln change in amino acid position 302 of u-PA and thereby eliminates the single glycosylation site in urokinase. W designates the mutation of the glycosylation

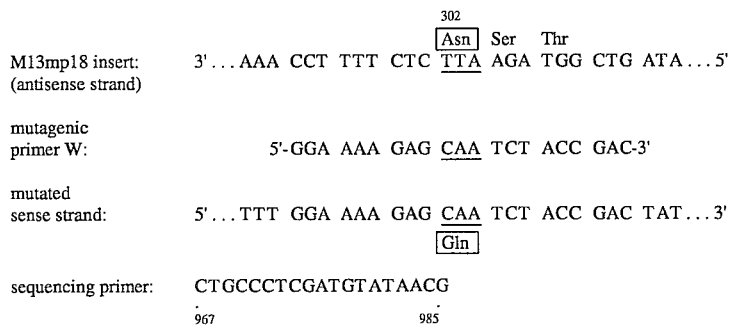

The mutagenic and sequencing primers are synthesized using the phosphoramidite method [M. H. Caruthers, in: Chemical and Enzymatic Synthesis of Gene Fragments, (,ed. H. G. Gassen and A. Lang) Verlag Chemie, Weinheim, Federal Republic of Germany] on an Applied Biosystem Model 380B synthesizer.

In vitro mutagenesis on single-stranded template DNA is performed as described by T. A. Kunkel [Proc. Nat. Acad. Sci. USA 82, 488–492 (1985)]. Uracil containing single-site in the u-PA B-chain (Asn302→Gln302). The positive clone is referred to as M13mp18/UPA-W.

Example 31: Transfer of the mutation [Gln302] in the urokinase B-chain to the FK$_2$UPA$^B$ hybrid:

Plasmid pJDB207/PHOS-I-FK$_2$UPA$^B$ is digested with SalI and XhoI. The 2.2 kb SalI-XhoI fragment is isolated, electroeluted from the agarose gel, purified by DE52 chromatography and precipitated in ethanol. This DNA fragment contains two MstI sites in the PH05 promoter and the u-PA sequence. 3 µg of the 2.2 kb SalI-XhoI fragment are partially digested with 3 units of MstI for 10 min at 370° C. The reaction products are separated on a preparative 0.8% agarose gel and the 1651 bp SalI-MstI fragment is isolated and electroeluted from the gel. The DNA fragment contains the SalI-BamHI sequence of pBR322, the PHO5 promoter, the invertase signal sequence and the $FK_2UPA^B$ coding sequence up to the MstI site in the u-PA part at nucleotide position 935.

RF-DNA is prepared for M13mp18/UPA-W (see Example 30) by the quick DNA isolation procedure [D. S. Holmes et al., Analyt. Biochem. 114, 193–97 (1981)]. 5 µg of DNA are digested with BamHI and MstI. After adding 2 µg of RNase (Serva) and incubating 5 min at 37° C. the 387 bp MstI-BamHI fragment is isolated on a preparative 0.8% agarose gel. The DNA fragment is electroeluted and precipitated in ethanol. The fragment contains the mutation AAT→CAA at nucleotide positions 1033–1035 (Asn302→Gln) in the urokinase B-chain.

Plasmid pJDB207/PHO5-I-UPA is cut with SalI and BamHI. The 6.6 kb vector fragment (see Example 29) is isolated. 0.2 µmoles of the 1651 bp SalI-MstI fragment, 0.2 µmoles of the 387 bp MstI-BamHI fragment and 0.1 µmoles of the 6.6 kb SalI-BamHI vector fragment are ligated. Competent *E. coli* HB101 $Ca^{2+}$ cells are transformed.

12 ampicillin resistant transformants are grown. Plasmid DNA is isolated and analysed by EcoRI and HindIII restriction cuts. The mutation (W) at the glycosylation site destroys the EcoRI site at nucleotide positions 1032–1037. The presence of the mutation is confirmed by DNA sequencing. One plasmid DNA with the mutation in the u-PA B-chain is referred to as pJDB207/PHO5-I-$FK_2UPA^B$-W. This plasmid has an intact glycosylation site in the kringle $K_2$, but the mutant site W(Asn302→Gln) in the u-PA B-chain.

Plasmids pJDB207/PHO5-I-FUPA$^B$-W and
pJDB207/PHO5-I-FGK$_2$UPA$^B$-W are constructed in the same way starting from the corresponding unmutated plasmids (see Example 29).

The 4.8 kb SalI-MpaI vector part of pJDB207/PHO5-I-$FK_2UPA^B$-W is replaced by the 6.2 kb SalI-HpaI vector fragment of pJDB207F1Lac (see Example 28). The 6.2 kb fragment has a 1.4 kb F1Lac insert of pEMBL19 cloned into the 4.8 kb fragment of pJDB207. Upon ligation, transformation and analysis of the new construct one correct plasmid with the F1Lac insert is referred to as pJDB207F1Lac/PHO5-I-$FK_2UPA^B$-W.

Plasmid pJDB207F1Lac/PHO5-I-FGK$_2$UPA$^B$-W is obtained the same way.

In the same way the 4.8 kb SalI-HpaI vector part of pJDB207/PHO5-I-MOU-$K_2TPA^B$ (see Example 15C) is replaced by the 6.2 kb SalI-HpaI vector fragment of pJDB207F1Lac. The resulting plasmid is referred to as pJDB207F1Lac/PHO5-I-UK$_2$TPA$^B$. Plasmids pJDB207F1Lac/PHO5-I-UK$_2$UPA$^B$, pJDB207F1Lac/PHO5-I-TPA$^A$UPA$^B$ and pJDB207F1Lac/PHOS-I-UPA$^A$TPA$^B$ are obtained in the same way from the plasmids without the F1Lac vector fragment.

Example 32: Mutation of the glycosylation site [Asn184GlySer] in the kringle $K_2$ of $FK_2UPA^B$-W:

a) Preparation of single-stranded template:

Plasmid pJDB207F1Lac/PHO5-I-$FK_2UPA^B$-W is used to transform competent *E. coli* RZ1032 $Ca^{2+}$ cells [T. A. Kunkel, supra]. One ampicillin resistant colony is grown in LB medium supplemented with 100 µg/ml of ampicillin, 20 µg/ml of thymidine and 20 µg/ml of desoxyadenosin. At a cell density of $1.10^8$/ml the cells are collected, washed in LB medium and resuspended in LB medium containing 100 µg/ml of ampicillin and 0.25 µg/ml of uridine. At an $OD_{600}$ of 0.3 helper phage R408 (Pharmacia-PL Biochemicals, Inc.) is added at a m.o.i. of 20. The culture is vigorously shaken for 5 hours at 37° C. The uracil-containing single-stranded DNA in the medium is isolated as described by T. A. Kunkel (supra). Starting from pEMBL19(+) (see Example 28) the F1 region is cloned in pJDB207 in an anti-clockwise orientation. The isolated single-stranded DNA is the sense strand of the $FK_2UPA^B$ insert in the expression plasmid.

b) Mutation of the glycosylation site at Asn184 of kringle $K_2$ of t-PA:

The mutation concerns the third position of the consensus amino acid recognition sequence for glycosylation. Ser186 is replaced by Ala.

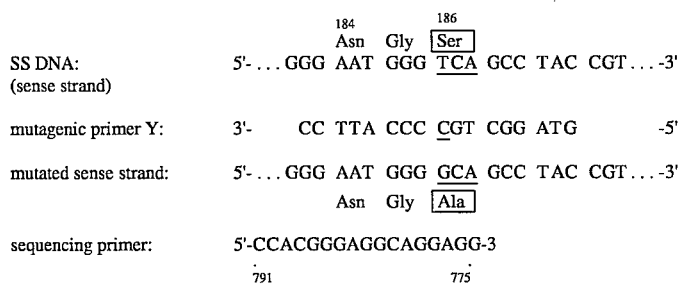

The mutation protocol is as described in Example 30. Instead of the M13 universal sequencing primer a PHO5 oligonucleotide primer of the formula 5'-AGTCGAGGT-TAGTATGGC-3' is used which hybridises to nucleotides −60 to −77 from the ATG in the PHO5 promoter. After the extension and ligation reaction, competent *E. coli* BMH71 $Ca^{2+}$ cells [Kunkel. supra] are transformed. Ampicillin resistant colonies are picked and grown in LB medium containing 100 mg/l of ampicillin. Plasmid DNA is prepared and analysed for the presence of the mutation by DNA sequencing. Mutation of the TCA codon to GCA results in a Ser→Ala change in amino acid position 186 of t-PA. The mutation in the third position of the consensus sequence eliminates the glycosylation site. One clone with the mutated DNA is referred to as pJDB207F1Lac/PHO5-I-$FK_2UPA^B$-WY.

Y designates the mutation of the glycosylation site at Asn184 in the $K_2$ of t-PA and W the mutation at Ash302 in the u-PA B-chain. The resulting unglycosylated $FK_2UPA^B$ hybrid protein has two amino acid changes: Ser186→Ala in the t-PA kringle $K_2$ and Ash302→Gln in the u-PA B-chain.

The analogous mutation of plasmid pJDB207F₁Lac/PHO5-I-FGK₂UPA^B-W (see Example 31) leads to plasmid pJDB207F1Lac/PHOS-I-FK₂UPA^B-WY, which codes for an unglycosylated FGK₂UPA^B hybrid protein.

Example 33: Construction of plasmid pJDB207/PHO5-I-K₂UPA^B-WY:

The nucleotide sequence coding for the hybrid $K_2UPA^B$ protein as defined by the amino acid sequence tPA(Serl-Gln3)(Gly176-Arg275)-uPA(Ile159-Leu411) is contained in plasmid pCGC5/K₂UPA^B. For expression in yeast the inducible PHO5 promoter is used and the invertase signal sequence is fused in frame to the $K_2UPA^B$ coding region. Plasmid pCGC5/K₂UPA^B is cut with BglII and AccI. The 487 bp BglII-AccI fragment is isolated. It contains the coding sequence from the BglII site of t-PA (nucleotide position 178) to the AccI site in u-PA (nucleotide position 779). The fragment is cut with HphI which results in 4 fragments.

Two oligodesoxyribonucleotides of the formula (I)  5'-CTGCATCTTACCAAGGAAACAGTGACTGCTACTTTGGGAATGGGGGCAGCCTACCGTGGCACG-3'
                                                    Asn   Ala (II) 3'-    AGAATGGTTCCTTTGTCACTGACGATGAAACCCTTACCCCGTCGGATGGCACCGTG -5' are synthesized using the phosphoramidite method on an Applied Biosystem Model 380B synthesizer. Oligonucleotides I and II form a double-stranded DNA linker. The 5 nucleotides at the staggered 5'end are part of the yeast invertase signal sequence, followed by the t-PA coding sequence (Serl-Gln3)(Gly1176-Thr191) to the first HphI cut site at nucleotide position 752 (see FIG. 1). The glycosylation site at position 729–737 (AsnGlySer) is mutated in the synthetic sequence from TCA (Set) to GCA (Ala), thus eliminating the glycosylation recognition sequence. The mutation of the glycosylation site at amino acid positions 184–186 of t-PA (e.g. the second glycosylation site in genuine t-PA) is designated Y.

Oligonucleotides I and II are phosphorylated at their 5'ends, heated for 10 min at 85° C. and annealed during cooling to room temperature. 10.5 μg (270 μmoles) of kinased, double-stranded linker DNA are listed at an 30-fold molar excess to the HphI cut DNA fragments (see above) as described in Example 8B. Excess linker molecules are removed by precipitation with isopropanol. The DNA is further digested with Scsi. The 252 bp fragment is isolated on a preparative 1.5% agarose gel, electroeluted and precipitated in ethanol.

Plasmid p31RII-12 (see Example 6B) is digested with SalI and XhoI. The isolated fragment is further digested with HgaI (see Example 6C) and BamMI. The resulting 591 bp BamHI-HgaI fragment is isolated. It contains the PHO5 promoter and the invertase signal sequence.

Plasmid pJDB207/PHO5-I-FK₂UPA^B-W is digested with BamHI. 5 μg of the linear DNA are partially digested with 10 units of Scsi for 10 min. The reaction is stopped by addition of 10 mM EDTA. The 7.7 kb BamHI-ScaI vector fragment is xsolated, electroeluted and precipitated in ethanol. It contains the 3' part of the coding sequence from the Scsi site in t-PA (position 953) to the end of the u-PA B-chain (PvuII site at position 1441 with XhoI linker added), the $PHO_5$ terminator and pJDB207 vector sequences. 0.2 μmoles each of the 591 bp BamHI-HgaI fragment and the 252 bp sticky ends (linker)-ScaI fragment and 0.1 μmoles of the 7.7 kb vector fragment are ligated. After transformation of E. coli HB101 $Ca^{2+}$ cells, 12 ampicillin resistant colonies are grown. Plasmid DNA is isolated and analysed by EcoRI and MindIll digests. The presence of the mutations is verified by DNA sequencing. One correct clone is chosen and referred to as pJDB207/PHOS-I-K₂UPAB-WY. The glycosylation sites in the kringle $K_2$ of t-PA and in the u-PA B-chain are both mutated (Y and W, respectively).

The resulting unglycosylated $K_2UPA^B$ hybrid protein has two amino acid changes: Ser186→Ala in the t-PA $K_2$ domain and Asn302→Gln in the u-PA B-chain.

Example 34: Mutation of the glycosylation sites [Asn184GlySer] and [Asn448ArgThr] in the $UK_2TPA^B$ hybrid Uracil containing single-stranded template [T. A. Kunkel, supra] of plasmid pJDB207F1Lac/PHOS-I-UK₂TPA^B (see Example 31) is prepared as described in Example 30. The mutation scheme for the glycosylation site at Asn184 is as described in Example 32. The mutation of the glycosylation site at Asn448 results in a Thr450→Ala amino acid change.

|  |  |
|---|---|
|  | 448       450<br>Asn Arg Thr |
| single stranded DNA<br>(sense strand) | 5'-...CTT AAC AGA ACA GTC ACC GAC A...-3' |
| mutagenic primer Z: | 3'-...GAA TTG TCT CGT CAG TGG CTG T...-5' |
| mutated sense strand: | 5'-...CTT AAC AGA GCA GTC ACC GAC A...-3'<br>Asn Arg Ala |
| sequencing primer: | 5'-TGGCAGGCGTCGTGCAA-3'<br>1603           1587 |

The mutation protocol is described in Example 30. The phosphorylated mutagenic primers Y and Z are both annealed to the uracil-containing single-stranded template of pJDB207F1Lac/PHO5-I-UK₂IPA^B. Additional use of the PHO5 oligonucleotide primer (see Example 32) is optional. After the extension and ligation reaction competent E. coli BMH71 $Ca^{2+}$ cells are transformed. Plasmid DNA of ampicillin resistant transformants is prepared and analysed for the presence of both mutations by DNA sequencing with the indicated sequencing primers.

Plasmid DNA of one clone with both mutations is referred to as pJDB207F1Lac/PHO5-I-UK$_2$TPA$^B$-YZ, Y designates the mutation of the glycosylation site at Asn184 and Z the mutation at Asn448. The unglycosylated UK$_2$TPA$^B$ hybrid protein has two amino acid changes: Ser186→Ala in the K$_2$ kringle of t-PA and Thr450→Ala in the t-PA B-chain.

The mutation protocol is also applicable for templates of pJDB207F1Lac/PHO5-I-UK$_2$UPA$^B$, pJDB207F1Lac/PHO5-I-TPA$^A$UPA$^B$ and pJDB207F1Lac/PHO5-I-UPA$^A$T-PA$^B$ (see Example 31) with mutagenic primer W for mutation of the glycosylation site in the u-PA B-chain and/or mutagenic primers Y and Z and others published in European Patent Application No. 225286 for the mutation of the glycosylation sites in t-PA.

Example 35: Transformation of Saccharomyces cerevisiae GRF18 and preparation of yeast cell extracts pJDB207/PHO5-I-FK$_2$UPA$^B$,
pJDB207F1Lac/PHO5-I-FK$_2$UPA$^B$-W,
pJDB207F1Lac/PHO5-I-FK$_2$UPA$^B$-WY,
pJDB207F1Lac/PHO5-I-UK$_2$TPA$^B$,
pJDB207F1Lac/PHO5-I-UK$_2$TPA$^B$-YZ,
pJDB207/PHO5-I-K$_2$UPA$^B$-WY,
pJDB207/PHO5-I-FUPA$^B$,
pJDB207/PHO5-I-FUPA$^B$-W,
pJDB207/PHO5-I-FGK$_2$UPA$^B$,
pJDB207/PHO5-I-FGK$_2$UPA$^B$-W,
pJDB207F1Lac/PHO5-I-FGK$_2$UPA$^B$-W and
pJDB207F1Lac/PHO5-I-FGK$_2$UPA$^{BG}$-WY are transformed into Saccharomyces cerevisiae strain GRF18 (DSM 3665). The transformation, cell growth and preparation of cell extracts are described in Example 16.

The resulting hybrid plasminogen activators can be purified in a manner analogous to that described in Examples 22 to 24.

Example 36: Preparation of lyophilised hybrid plasminogen activators

The solution obtained in any one of Examples 22 to 24 are further purified and lyophilised as follows:

The solution is diluted with 10 volumes of 0.1 M ammonium acetate pH 5.0 (total volume 80 ml) and applied to a column containing 5 ml CM-Sepharose Fast Flow (Pharmacia) at a flow rate of 25 ml/h at room temperature. (The column has been pre-equilibrated with 0.1 M ammonium acetate). The product-free percolate is discarded. The column is washed with 15 ml of 0.1 M ammonium acetate pH 5.0 and with 10 ml of 0.1 M ammonium acetate pH 7.0. Elution of the adsorbed hybrid PA is then effected by 1 M ammonium acetate pH 8.6 at room temperature (flow rate 5 ml/h). In order to prevent gas formation on the column, elution is performed at an excess pressure of 1 to 1.5 bar. The hybrid PA content of the eluate is measured by an UV monitor (280 nm). A fraction containing about 90% of the eluted hybrid PA is gathered and subjected to lyophilisation. The purity of the solid hybrid PA lyophilisate is about or more than 95% as judged by HPLC. The product is free of detergents.

Example 37: First pharmaceutical composition for parenteral administration

A solution containing pure uPA(1–44)-tPA(176–527) obtained as described above is dialysed against 0.3 molar sodium chloride containing 0.01% Tween 80® and stored at −80° C. Prior to administration the concentration is adjusted to 75 µg/µml of total PA and 0.3 M NaCl. The solution is sterilised by filtration through a 0.22 µm membrane filter.

Instead of the above-mentioned PA it is also possible to use the same amount of a different PA described in the preceding Examples, such as, for example, uPA(1–158')-tPA(276–52T), uPA(1–131)-tPA(263–527), tPA(1–275)-uPA(I59–411), tPA(1–262)-uPA(132–411), gPA(1–44)-tPA(176–261)-uPA(134–411), tpA(1–49)-tPA(262–275)-uPA(159–411), tPA(1–49)-uPA(134–411), tpA(1–49)-tPA(176–275)-uPA(159–411), tPA(1–49)-tPA(176–262)-uPA(132–411), tpA(1–3)-tPA(176–275)-uPA(159–411), tPA(1–86)-tPA(1 76–275)-uPA(159–411) or tPA(1–86)-tPA(1 76–262)-uPA(132–411), or a mutant hybrid PA, such as, for example, tPA(1–49)-tPA(262–275)-uPA(159–301, Gln, 303–411), tPA(1–49)-tPA(176–185, Ala, 187–275)-uPA(159–301, Gln, 303–411), uPA(1–44)-tPA(176–185, Ala, 187–449, Ala, 451–527), tPA(1–3)-tPA(176–185, Ala, 187–275)-uPA(159–301, Gln, 303–411) or tPA(1–86)-tPA(176–185, Ala, 187–275)-uPA(159–301, Gln, 303–411).

Example 38: Second pharmaceutical composition for parenteral administration (dispersion for injection)

169.3 mg soybean lecithin (soybean phosphatide NC 95, manufacturer: Nattermann, Cologne, Germany; purity 90–96%; composition of fatty acids: linoleic acid 61–71%, linolenic acid 4–7%, oleic acid 6–13%, palmitic acid 10–15%, stearic acid 1.5–3.5%) and 92.7 mg pure sodium glycocholate are dissolved in 752.5 ml of sterilized water. The solution is adjusted to pH 7.4 with 1N NaOH. 10 mg of lyophilized uPA(1–44)-tPA(176–527) is added. The mixture is stirred until a clear solution has been obtained. The solution is sterilized by filtration through a 0.22 µm membrane filter and filled into ampoules.

Instead of the above-mentioned PA it is also possible to use the same amount of a different PA described in the preceding Examples, such as. for example, uPA(1–158)-tPA(276–527), uPA(1–131)-tPA(263–527), tPA(1–275)-uPA(159–411), tPA(1–262)-uPA(132–411), uPA(1–44)-tPA(176–261)-uPA(134–411), tPA(1–49)-tPA(262–275)-uPA( 159–411), tPA(1–49)-uPA(134–411), tPA(1–49)-tPA(176–275)-uPA(159–411), tPA(1–49)-tPA(176–262)-uPA(1 32–411), tPA(1–3)-tPA(176–275)-uPA(159–411), tPA(1–86)-tPA(176–275)-uPA(159–411) or tPA(1–86)-tPA(176–262) -uPA(132–411), or a mutant hybrid PA, such as, for example, tPA(1 –49)-tPA(262–275)-uPA(159–301, Gln, 303–411), tPA(1–49)-tPA(176–185, Ala, 187–275)-uPA(159–301, Gln, 303–411), uPA(1–44)-tPA(176–185, Ala, 187–449, Ala, 451–527), tPA(1–3)-tPA(176–185, Ala, 187–275)-uPA(159–301, Gln, 303–411) or tPA(1–86)-tPA(176–185, Ala, 87–275)-uPA(159–301. Gln, 303–411).

Example 39 Third pharmaceutical composition for parenteral administration (including bolus injection)

100 mg of the hybrid plasminogen activator or mutant hybrid plasminogen activator such as one of those mentioned in Examples 37 and 38, is dissolved in 1000 ml of 50 mM glutamic acid/sodium glutamate containing 0.7% NaCl, pH 4.5. The solution is filled into ampoules and can be used for intravenous (bolus) infusion.

Deposition of microorganisms

The following strains were deposited on October 23, 1987 at the "Deutsche Sammlung yon Mikroorganismen" (DSM), Grisebachstrasse 8, D-3000 Göttingen (accession numbers given):

|  | accession no. |
|---|---|
| E. coli HB101/pW349F | DSM 4291 |
| E. coli HB101/pCS16 | DSM 4294 |
| E. coli HB101/pcUK176 | DSM 4290 |
| E. coli HB101/pCGA26 | DSM 4296 |
| E. coli HB101/pSV2911neo. | DSM 4292 |

The following hybridoma cell lines were deposited on November 20, 1987 at the "Collection Nationale de Cultures de Microorganismes", Institut Pasteur, Paris (CNCM) under the accession numbers given:

| hybridoma | accession no. |
|---|---|
| 405B.33.3 | I-715 |
| 406A.23.7 | I-716 |
| 407A.15.27 | I-717 |

We claim:

1. A hybrid plasminogen activator selected from the group consisting of a) a hybrid plasminogen activator consisting of, in the order of N-terminus to C-terminus, the human t-PA kringle 2 domain, a first junction sequence, and the human u-PA catalytic domain, said first junction sequence linking the human t-PA kringle 2 domain to the human u-PA catalytic domain, said first junction sequence including a processing site capable of being cleaved by plasmin and, N-terminal thereto, a cysteine residue capable of forming a sulphur-sulphur bridge to the human u-PA catalytic domain, wherein said first junction sequence is selected from the group consisting of the junction sequence linking the A-chain to the B-chain in human t-PA, the junction sequence linking the A-chain to the B-chain in human u-PA, and a hybrid junction sequence composed of amino acids 262 to 275 of human t-PA and amino acids 159 to 188 of human u-PA and optionally additionally one or more sequences selected from the group consisting of (i) a second junction sequence consisting of the junction sequence N-terminally flanking the kringle 2 domain in human bPA or a fragment thereof, said fragment consisting of amino acids 176 to 179 of human t-PA, wherein said second junction sequence is positioned in the hybrid plasminogen activator N-terminally to the human t-PA kringle 2 domain; and (ii) the T-region of human t-PA or a N-terminal fragment thereof, said fragment consisting of amino acids 1 to 3 of human t-PA, which T-region or fragment thereof is positioned at the N-terminus of the hybrid plasminogen activator;

b) a hybrid plasminogen activator consisting of, in the order of N-terminus to C-terminus, the human t-PA finger domain, the human t-PA kringle 2 domain, a third junction sequence, and the human u-PA catalytic domain, said third junction sequence linking the human t-PA kringle 2 domain to the human u-PA catalytic domain, said third junction sequence including a processing site capable of being cleaved by plasmin and, N-terminal thereto, a cysteine residue capable of forming a sulphur-sulphur bridge to the human u-PA catalytic domain, wherein said third junction sequence is selected from the group consisting of the junction sequence linking the A-chain to the B-chain in human tPA, the junction sequence linking the A-chain to the B-chain in human u-PA, and a hybrid junction sequence composed of amino acids 262 to 275 of human t-PA and amino acids 159 to 188 of human u-PA;

and optionally additionally one or more sequences selected from the group consisting of (i) a fourth junction sequence consisting of the junction sequence C-terminally flanking the finger domain in human t-PA, the junction sequence N-terminally flanking the kringle 2 domain in human t-PA, or a fused junction sequence composed of both said junction sequences or of amino acids 44 to 49 and amino acids 176 to 179 of human t-PA, wherein said fourth junction sequence is positioned between the t-PA finger domain and the t-PA kringle 2 domain in the hybrid plasminogen activator; and (ii) the T-region of human t-PA or a N-terminal fragment thereof, said fragment consisting of amino acids 1 to 3 of human t-PA, which T-region or fragment thereof is positioned at the N-terminus of the hybrid plasminogen activator; and c) a hybrid plasminogen activator consisting of, in the order of N-terminus to C-terminus, the human t-PA finger domain, the human t-PA growth factor domain, the human t-PA kringle 2 domain, a fifth junction sequence, and the human u-PA catalytic domain, said fifth junction sequence linking the human t-PA kringle 2 domain to the human u-PA catalytic domain, said fifth junction sequence including a processing site capable of being cleaved by plasmin and, N-terminal thereto, a cysteine residue capable of forming a sulphur-sulphur bridge to the human u-PA catalytic domain, wherein said fifth junction sequence is selected from the group consisting of the junction sequence linking the A-chain to the B-chain in human t-PA, the junction sequence linking the A-chain to the B-chain in human u-PA, and a hybrid junction sequence composed of amino acids 262 to 275 of human t-PA and amino acids 159 to 188 of human u-PA;

and optionally additionally one or more sequences selected from the group consisting of (i) a sixth junction sequence consisting of the junction sequence C-terminally flanking the finger domain in human t-PA or a fragment thereof, said fragment consisting of amino acids 44 to 49 of human t-PA, wherein said sixth junction sequence is positioned between the finger and growth factor domain in the hybrid plasminogen activator;

(ii) a seventh junction sequence consisting of the junction sequence C-terminally flanking the growth factor domain in human t-PA the junction sequence N-terminally flanking the kringle 2 domain in human t-PA, or a fused junction sequence composed of said both junction sequences or of amino acids 85 to 86 and amino acids 174 to 176 of human t-PA, wherein said seventh junction sequence is positioned between the growth factor and kringle 2 domain in the hybrid plasminogen activator; and (iii) the T-region of human t-PA or a N-terminal fragment thereof, said fragment consisting of amino acids 1 to 3 of human t-PA, which T-region or fragment thereof is positioned at the N-terminus of the hybrid plasminogen activator.

2. A hybrid plasminogen activator according to claim 1 selected from the group consisting of tPA(1–3)-tPA(176–275)-uPA(159–411), tPA(1–49)-tPA(176–275)-uPA(159–411), and tPA(1–86)-tPA(176–275)-uPA(159–411).

3. A hybrid plasminogen activator according to claim 1 which is tPA(1–3)-tPA(176–275)-uPA(159–411).

4. A pharmaceutical composition comprising a hybrid plasminogen activator according to claim 1 together with a pharmaceutically acceptable carder.

5. A method for the treatment of thrombosis or other conditions where it is desired to locally activate in a mammal the fibrinolytic or proteolytic activity of plasmin by cleavage of plasminogen with a compound according to claim 1, said method comprising administering to said mammal a therapeutically effective amount of a compound according to claim 1.

* * * * *